US008431572B2

(12) United States Patent
Schadt et al.

(10) Patent No.: US 8,431,572 B2
(45) Date of Patent: Apr. 30, 2013

(54) 2-OXO-3-BENZYLBENZOXAZOL-2-ONE DERIVATIVES AND RELATED COMPOUNDS AS MET KINASE INHIBITORS FOR THE TREATMENT OF TUMOURS

(75) Inventors: Oliver Schadt, Rodenbach (DE); Dieter Dorsch, Ober-Ramstadt (DE); Frank Stieber, Heidelberg (DE); Andree Blaukat, Muehltal (DE)

(73) Assignee: Merck Patent Gesellschaft mit beschrankter Haftung, Darmstadt (DE)

( * ) Notice: Subject to any disclaimer, the term of this patent is extended or adjusted under 35 U.S.C. 154(b) by 0 days.

(21) Appl. No.: 13/177,261

(22) Filed: Jul. 6, 2011

(65) Prior Publication Data

US 2011/0263596 A1    Oct. 27, 2011

Related U.S. Application Data

(62) Division of application No. 12/663,206, filed as application No. PCT/EP2008/003696 on May 8, 2008, now Pat. No. 8,071,593.

(30) Foreign Application Priority Data

Jun. 6, 2007   (DE) .......................... 10 2007 026 341

(51) Int. Cl.
*A61K 31/5355* (2006.01)
*A61K 31/496* (2006.01)
*A61K 31/501* (2006.01)
*A61K 31/506* (2006.01)
*A61K 31/443* (2006.01)
*A61K 31/4355* (2006.01)
*A61K 31/421* (2006.01)

(52) U.S. Cl.
USPC ................ 514/232.8; 514/234.2; 514/252.02; 514/252.03; 514/252.04; 514/252.18; 514/252.19; 514/253.01; 514/254.02; 514/254.03; 514/256; 514/269; 514/302; 514/318; 514/338; 514/375

(58) Field of Classification Search ........................ None
See application file for complete search history.

(56) References Cited

U.S. PATENT DOCUMENTS

| 6,242,461 | B1 | 6/2001 | Goldstein |
| 6,403,586 | B1 | 6/2002 | Ohkuchi et al. |
| 8,071,593 | B2 | 12/2011 | Schadt et al. |
| 8,173,653 | B2 | 5/2012 | Dorsch et al. |
| 8,321,692 | B2 | 12/2012 | Schadt et al. |
| 2004/0152739 | A1 | 8/2004 | Hanau |
| 2004/0259863 | A1 | 12/2004 | Eggenweiler et al. |
| 2005/0107391 | A1 | 5/2005 | Cui et al. |
| 2007/0015771 | A1 | 1/2007 | Matteucci et al. |
| 2007/0043057 | A1 | 2/2007 | Matteucci et al. |
| 2007/0203136 | A1 | 8/2007 | Lu et al. |
| 2007/0265272 | A1 | 11/2007 | Cheng et al. |
| 2008/0293719 | A1 | 11/2008 | Dorsch et al. |
| 2009/0098181 | A1 | 4/2009 | Lu et al. |
| 2009/0124612 | A1 | 5/2009 | Albrecht et al. |
| 2010/0197309 | A1 | 8/2010 | Schadt et al. |
| 2010/0234354 | A1 | 9/2010 | Dorsch et al. |
| 2010/0273796 | A1 | 10/2010 | Dorsch et al. |
| 2010/0280030 | A1 | 11/2010 | Schadt et al. |
| 2010/0286390 | A1 | 11/2010 | Shigeta et al. |
| 2011/0034474 | A1 | 2/2011 | Dorsch et al. |
| 2011/0092498 | A1 | 4/2011 | Dorsch et al. |
| 2011/0098269 | A1 | 4/2011 | Becknell et al. |
| 2011/0112061 | A1 | 5/2011 | Hu et al. |
| 2011/0263596 | A1 | 10/2011 | Schadt et al. |
| 2011/0269957 | A1 | 11/2011 | Fandrick et al. |
| 2012/0028988 | A1 | 2/2012 | Sakamoto et al. |
| 2012/0040949 | A1 | 2/2012 | Berthel et al. |

FOREIGN PATENT DOCUMENTS

| DE | 196 04 388 | 8/1997 |
| DE | 10 2005 057 | 6/2007 |
| EP | 1 061 077 | 12/2000 |
| JP | 10-259176 | 9/1998 |
| JP | 2001 192384 | 7/2001 |
| WO | WO-03 037349 | 5/2003 |
| WO | WO 2004/058762 A | 7/2004 |
| WO | WO-2005 004607 | 1/2005 |
| WO | WO-2006 015263 | 2/2006 |
| WO | WO-2007 044796 | 4/2007 |
| WO | WO 2007/057093 A | 5/2007 |
| WO | WO-2007 064797 | 6/2007 |
| WO | WO-2007 065518 | 6/2007 |

(Continued)

OTHER PUBLICATIONS http://www.uspto.gov/web/offices/pac/dapp/1pecba.htm#7; last accessed on Nov. 22, 2011.*
International Search Report "International Application No. PCT/EP2008/003696," Date of Completion Sep. 18, 2008, Date of Mailing Oct. 1, 2008, 4 pages.
Flouzat, Christine Et Al. "Synthesis and N-substitution of an uncommon heterocyclic system: oxazolo[5,4-b]pyridin-2(1H)-one," Tetrahedron Letters, Bd. 33, Nr. 32, 1992 Seiten 4571-4574, XP00249354.
Ucar, Huseyin et al., "Fries Like" Rearragement: a novel and efficient metod for the sythesis of 6-acyl-2(3H)-benzoxazolones and 6-acyl-2(3H)-benzothiazolones Tetrahedron, Bd. 54, Nr. 9, 1998, Seiten 1763-1772 XP002496355.
Database CA (Online) Chemical Abstracts Service, Columbus, Ohio US:2002, Dushamov, D.A.et al., Acylation of 6-halobenzoxazolin-2-ones by acid chlorides in the presence of a small quantity of iron(III) chloride hexahydrate, XP002496356.

(Continued)

*Primary Examiner* — Joseph K. McKane
*Assistant Examiner* — Alicia L Otton
(74) *Attorney, Agent, or Firm* — Millen, White, Zelano & Branigan, P.C.

(57) ABSTRACT

Described are compounds which inhibit, regulate and/or modulate kinase signal transduction, for example of Met kinase. The compounds are of the formulae A1 to A148 and B1 described herein, including 2-oxobenzoxazol-3-ylmethyl]phenyl}carbamate and 2-oxooxazolo[4,5-b]pyridin-3-ylmethyl)phenyl]carbamate compounds, and pharmaceutically usable salts, tautomers and stereoisomers thereof, including mixtures thereof in all ratios. Also described are compositions containing these compounds. Also described are methods for the treatment of diseases in which the inhibition, regulation and/or modulation of kinase signal transduction plays a role by administering these compounds.

5 Claims, No Drawings

FOREIGN PATENT DOCUMENTS

| | | |
|---|---|---|
| WO | WO-2007 075567 | 7/2007 |
| WO | WO-2007 130383 | 11/2007 |
| WO | WO-2007 132308 | 11/2007 |
| WO | WO-2008 008539 | 1/2008 |
| WO | WO-2008 075068 | 6/2008 |
| WO | WO-2009 006959 | 1/2009 |
| WO | WO-2009 007074 | 1/2009 |
| WO | WO-2009 050197 | 4/2009 |
| WO | WO-2009 053737 | 4/2009 |
| WO | WO-2009 063061 | 5/2009 |
| WO | WO-2009 080314 | 7/2009 |
| WO | WO-2009 080364 | 7/2009 |
| WO | WO-2009 080533 | 7/2009 |
| WO | WO-2009 080534 | 7/2009 |
| WO | WO-2009 080555 | 7/2009 |
| WO | WO-2009 080721 | 7/2009 |
| WO | WO-2009 080725 | 7/2009 |
| WO | WO-2009 081197 | 7/2009 |
| WO | WO-2009 083076 | 7/2009 |
| WO | WO-2009 083105 | 7/2009 |
| WO | WO-2009 085659 | 7/2009 |
| WO | WO-2009 086041 | 7/2009 |
| WO | WO-2009 086264 | 7/2009 |

OTHER PUBLICATIONS

Database CA (Online) Chemical Abstracts Service, Columbus, Ohio US:1979, Domagalina, Eugenia et al, "Acylation of benzoxazolin-2-ones and 3-hydroxyl-1, 2 benzisoxazoles," XP002496357 Polish Journal of Pharmacology and Pharmacy.

Database CA (Online) Chemical Abstracts Service, Columbus, Ohio US; 1967, Nitta, yoshihiro et al: "Benzoxazolone derivatives," XP002496358.

Lala et al. "Role of nitric oxide in tumor progression: Lessons from experimental tumors." Cancer and Metastasis Review (1998), 17(1), 91-106.

Morissette et al. "High-throughput crystallization: polymorphs, salts, co-crystals and solvates of pharmaceutical solids." Advanced Drug Deliver Reviews 2004, 56 275-300.

Sausville et al. "Contributions of Human Tumor Xenografts to Anti-cancer Drug Development" Cancer Res. 2006, 66(7), Apr. 1, 2006.

Souillac et al. Characterization of Delivery Systems, Differential Scanning Calorimetry, pp. 217-218 (in Encyclopedia of Controlled Drug Delivery, 1999, John Wiley & Sons, pp. 212-227).

Stella, V. "Prodrugs as therapeutics" Expert Opin. Ther. Patents (2004), 14(3):277-280.

Testa, B. "Prodrug research: futile or fertile?" Biochemical Pharmacology, 68 (2004): 2097-2106.

Vippagunta, S.R. "Crystalline Solids" Advanced Drug Delivery Reviews 48(2001):3-26.

Wolff et al. Burger's Medicinal Chemistry and Drug Discovery. 5$^{th}$ Ed. vol. 1: Principles and Practice. pp. 975-977, (1995).

"Cancer" MedLine Plus (2009). Accessed Mar. 17, 2009. http://www.nlm.nih.gov/medlineplus/cancer.html.

Ettmayer et al. "Lessons Learned from Marketed and Investigational Prodrugs" J. Med. Chem., (2004), 47(10):2393-2404.

Golub et al. "Molecular Classification of Cancer: Class Discovery and Class Prediction by Gene Expression Monitoring" Science (1999), 286:521-537.

Johnson et al. "Relationships between drug activity in NCI preclinical in vitro and in vivo models and early clinical trials." British Journal of Cancer (2001) 84(10):1424-1431.

Zou, Helen Y. et al. "Sensitivity of Selected Human tumor Models to PF-04217903, a Novel Selective c-Met Kinase Inhibitor", Molecular Cancer Therapeutics, American Association for Cancer Research. 32 pages. Published: Mar. 2, 2012.

Zou, Helen Y. et al. "An Orally Available Small-Molecule Inhibitor of c-Met, PF-2341066, Exhibits Cytoreductive Antitumor Efficacy through Antiproliferative and Antiangiogenic Mechanisms", Cancer Res 2007; 67:(9)4408-4417. Dated: May 1, 2007. www.aacrjournals.org.

Knowles, Lynn M. et al. "HGF and c-Met Participate in Paracrine Tumorigenic Pathways in Head and Neck Squamous Cell Cancer", Clin Cancer Res, Jun. 1, 2009; 15(11):3740-3750. www.aacrjournals.org.

Sampson, Erik R. et al. "The Orally Bioavailable Met Inhibitor PF-2341066 Inhibits Osteosarcoma Growth and Osteolysis/Matrix Production in a Xenograft Model", Journal of Bone and Mineral Research, 26(6):1283-1294; Dated: Jun. 2011.

Jin, Hongkui et al. "MetMAb, the One-Armed 5D5 Anti-c-Met Antibody, Inhibits Orthotopic Pancreatic Tumor Growth and Improves Survival", Cancer Res 2008;68(11):4360-4368; Jun. 1, 2008. www.aacrjournals.org.

Zillhardt, Marion et al. "Foretinib (GSK1363089), an Orally Available Multikinase Inhibitor of c-Met and VEGFR-2, Blocks Proliferation, Induces Anoikis, and Impairs Ovarian Cancer Metastasis", Clin Cancer Res 2011;17:4042-4051. Published: May 6, 2011. www.aacrjournals.org.

Qian, Fawn et al. "Inhibition of Tumor Cell Growth, Invasion, and Metastasis by EXEL-2880 (XL880, GSK1363089), a Novel Inhibitor of HGF and VEGF Receptor Tyrosine Kinases", Cancer Res 2009;69(20):8009-8016. Dated: Oct. 15, 2009. www.aacrjournals.org.

Liu, Xiangdong et al. "A novel kinase inhibitor INCB28060 blocks c-MET-dependent signaling, neoplastic activities, and crosstalk with EGFR and HER-3", Clin Cancer Res (45 pages); Published: Sep. 14, 2011.

Guessous, Fadila et al. "An orally Bioavailable c-Met Kinase Inhibitor Potently Inhibits Brain Tumor Malignancy and Growth", Anti-Cancer in Medicinal Chemistry, 2010, 10(1):28-35.

Buchanan, Sean G. "SGX523 is an exquisitely selectively, ATP-competitive inhibitor of the MET receptor tyrosine kinase with antitumor activity in vivo" Molecular Cancer Therapeutics, Dec. 2009;8(12): 3181-3190.

Berthou, S. et al., "The Met kinase inhibitor SU11274 exhibits a selective inhibition pattern toward different receptor mutated variants," Oncogene, 2004, vol. 23, pp. 5387-5393.

Cancer Drug Design and Discovery, Neidle, Stephen, ed. (Elsevier/Academic Press), pp. 427-431, 2008.

Chen et al., Circulation, 2008, vol. 118, pp. 84-95.

Database Beilstein, Beilstein Institute for Organic Chemistry, Frankfurt, DE, XP002506064M 1991.

Databse Beilstein, Beilstein Institute for Organic Chemistry, Frankfurt, DE, XP002506065, Need Date, 2008.

Fujisawa Pharmaceut Co Ltd., "Pyrazolopyridine compound and pharmaceutical use thereof," Patent Abstracts of Japan, Publication Date: Jul. 17, 2001, English Abstract of JP-2001 192384.

Glen, H. et al., "E7080, a multi-targeted tyrosin kinase inhibitor suppresses tumor cell migration and invasion," BMC Cancer, 2011, vol. 11, No. 309.

H. Refaat et al., "Synthesis and Anti-Inflammatory Activity of Certain Piperazinylthienylpyridazine Derivatives," Arch Pharm Res., vol. 30, No. 7 (2007) pp. 803-811.

Hackh's Chem Dict., 3$^{rd}$. Ed., 1944, p. 18.

Hawley's Condensed Chem Dict., 14$^{th}$ Ed., 2002.

Hill, K. S. et al., "Met Receptor Tyrosine Kinase Signaling Induces Secretion of the Angiogenic Chemokine Interleukin-8/CXCL8 in Pancreatic Cancer," PLoS ONE, Jul. 1, 2012, vol. 7, No. 7, e40420.

http://www.iupac.org/goldbook/A00123.pdf, downloaded Oct. 29, 2010.

International Search Report for PCT/EP2008/003473 dated Jul. 28, 2008.

International Search Report for PCT/EP2008/005928 dated Dec. 11, 2008.

International Search Report of PCT/EP2008/009970 dated Jan. 28, 2009.

International Search Report of PCT/EP2009/002137 (Jun. 4, 2009).

International Search Report of PCT/EP2009/003675 (Aug. 26, 2009).

Jin et al., Mol. Cancer Ther., Jul. 2006, vol. 5, pp. 1754-1763.

Lima, L. M. et al., "Bioisosterism: a useful strategy for molecular modification and drug design," Current Medicinal Chemistry, 2005, vol. 12, No. 1, pp. 23-49.

Locatelli et al., J. Biol. Chem., Jun. 17, 2011, vol. 286, No. 24, pp. 21062-21072.

M. Goekce et al., "Synthesis of New Mannich Bases of Arylpyridazinones as Analgesic and Anti-Inflammatory Agents," Drug Research, vol. 55, No. 6 (2005) pp. 318-325.

Merck Patent GmbH, New Aryl-alkyl diazinone derivatives, Espacenet, Publication Date: Aug. 14, 1997; English Abstract of DE-196 04 388.

Office Action for Related Columbian Patent Application No. 09-138245 dated Sep. 21, 2012.

Samlowski et al., BJU Int., 2008, vol. 102, No. 2, pp. 162-165, Abstract.

Search Report for Chilean Patent Application No. 3854-08 filed Dec. 19, 2008.

Singapore Written Opinion for Application No. 201007486-2 (Sep. 26, 2011).

Smolen et al., Proc. Natl Acad Sci USA, Feb. 2006, vol. 103, No. 7, pp. 2316-2321.

Tuynman et al., Br. J. Cancer, 2008, vol. 98, No. 6, pp. 1102-1108, Abstract.

Underiner et al., Anti-Cancer Agents in Medicinal Chemistry, 2010, vol. 10, pp. 7-27.

Wang et al., Clin Cancer Res., Mar. 15, 2012, vol. 18, No. 6, pp. 1663-1671.

Ziegler, D. S. et al., "Resistance of human glioblastoma multiforme cells to growth factor inhibitors is overcome by blockade of inhibitors of apoptosis proteins," Journal of Clinical Investigation, Sep. 9, 2008, vol. 118 pp. 3109-3122.

International Search Report of PCT/EP2009/005172 dated Jan. 26, 2010.

Berge et al., "Pharmaceutical salts," Journal of Pharmaceutical Science, 1977, vol. 66, No. 1, pp. 1-19.

Gould et al., "Salt selection for basic drugs," International Journal of Pharmaceutics, 1986, vol. 33, p. 201.

International Search Report of PCT/EP2009/008358 dated Feb. 5, 2010.

* cited by examiner

2-OXO-3-BENZYLBENZOXAZOL-2-ONE DERIVATIVES AND RELATED COMPOUNDS AS MET KINASE INHIBITORS FOR THE TREATMENT OF TUMOURS

This application is a divisional of U.S. Ser. No. 12/663,206, filed Jul. 26, 2010, now U.S. Pat. No. 8,071,593, issued Dec. 6, 2011. U.S. Ser. No. 12/663,206 is a 371 US National phase application of PCT thternational Application No. PCT/EP2008/003696, filed May 8, 2008. This application claims priority to German Application No. DE 102007026341.6 filed Jun. 6, 2007.

BACKGROUND OF THE INVENTION

The invention had the object of finding novel compounds having valuable properties, in particular those which can be used for the preparation of medicaments.

The present invention relates to compounds and to the use of compounds in which the inhibition, regulation and/or modulation of signal transduction by kinases, in particular tyrosine kinases and/or serine/threonine kinases, plays a role, furthermore to pharmaceutical compositions which comprise these compounds, and to the use of the compounds for the treatment of kinase-induced diseases.

In particular, the present invention relates to compounds and to the use of compounds in which the inhibition, regulation and/or modulation of signal transduction by Met kinase plays a role.

One of the principal mechanisms by which cellular regulation is effected is through the transduction of extracellular signals across the membrane that in turn modulate biochemical pathways within the cell. Protein phosphorylation represents one course by which intracellular signals are propagated from molecule to molecule resulting finally in a cellular response. These signal transduction cascades are highly regulated and often overlap, as is evident from the existence of many protein kinases as well as phosphatases. Phosphorylation of proteins occurs predominantly at serine, threonine or tyrosine residues, and protein kinases have therefore been classified by their specificity of phosphorylation site, i.e. serine/threonine kinases and tyrosine kinases. Since phosphorylation is such a ubiquitous process within cells and since cellular phenotypes are largely influenced by the activity of these pathways, it is currently believed that a number of disease states and/or diseases are attributable to either aberrant activation or functional mutations in the molecular components of kinase cascades. Consequently, considerable attention has been devoted to the characterisation of these proteins and compounds that are able to modulate their activity (for a review see: Weinstein-Oppenheimer et al. Pharma. &. Therap., 2000, 88, 229-279).

The role of the receptor tyrosine kinase Met in human oncogenesis and the possibility of inhibition of HGF (hepatocyte growth factor) dependent Met activation are described by S. Berthou et al. in Oncogene, Vol. 23, No. 31, pages 5387-5393 (2004). The inhibitor SU11274 described therein, a pyrrole-indoline compound, is potentially suitable for combating cancer. Another Met kinase inhibitor for cancer therapy is described by J. G. Christensen et al. in Cancer Res. 2003, 63(21), 7345-55.

A further tyrosine kinase inhibitor for combating cancer is reported by H. Hov et al. in Clinical Cancer Research Vol. 10, 6686-6694 (2004). The compound PHA-665752, an indole derivative, is directed against the HGF receptor c-Met. It is furthermore reported therein that HGF and Met make a considerable contribution to the malignant process of various forms of cancer, such as, for example, multiple myeloma.

The synthesis of small compounds which specifically inhibit, regulate and/or modulate signal transduction by tyrosine kinases and/or serine/threonine kinases, in particular Met kinase, is therefore desirable and an aim of the present invention.

It has been found that the compounds according to the invention and salts thereof have very valuable pharmacological properties while being well tolerated.

The present invention specifically relates to compounds of the formula I which inhibit, regulate and/or modulate signal transduction by Met kinase, to compositions which comprise these compounds, and to processes for the use thereof for the treatment of Met kinase-induced diseases and complaints, such as angiogenesis, cancer, tumour formation, growth and propagation, arteriosclerosis, ocular diseases, such as age-induced macular degeneration, choroidal neovascularisation and diabetic retinopathy, inflammatory diseases, arthritis, thrombosis, fibrosis, glomerulonephritis, neurodegeneration, psoriasis, restenosis, wound healing, transplant rejection, metabolic diseases and diseases of the immune system, also autoimmune diseases, cirrhosis, diabetes and diseases of the blood vessels, also instability and permeability and the like in mammals.

Solid tumours, in particular fast-growing tumours, can be treated with Met kinase inhibitors. These solid tumours include monocytic leukaemia, brain, urogenital, lymphatic system, stomach, laryngeal and lung carcinoma, including lung adenocarcinoma and small-cell lung carcinoma.

The present invention is directed to processes for the regulation, modulation or inhibition of Met kinase for the prevention and/or treatment of diseases in connection with unregulated or disturbed Met kinase activity. In particular, the compounds of the formula I can also be employed in the treatment of certain forms of cancer. The compounds of the formula I can furthermore be used to provide additive or synergistic effects in certain existing cancer chemotherapies, and/or can be used to restore the efficacy of certain existing cancer chemotherapies and radiotherapies.

The compounds of the formula I can furthermore be used for the isolation and investigation of the activity or expression of Met kinase. In addition, they are particularly suitable for use in diagnostic methods for diseases in connection with unregulated or disturbed Met kinase activity.

It can be shown that the compounds according to the invention have an antiproliferative action in vivo in a xenotransplant tumour model. The compounds according to the invention are administered to a patient having a hyperproliferative disease, for example to inhibit tumour growth, to reduce inflammation associated with a lymphoproliferative disease, to inhibit transplant rejection or neurological damage due to tissue repair, etc. The present compounds are suitable for prophylactic or therapeutic purposes. As used herein, the term "treatment" is used to refer to both prevention of diseases and treatment of pre-existing conditions. The prevention of proliferation is achieved by administration of the compounds according to the invention prior to the development of overt disease, for example to prevent the growth of tumours, prevent metastatic growth, diminish restenosis associated with cardiovascular surgery, etc. Alternatively, the compounds are used for the treatment of ongoing diseases by stabilising or improving the clinical symptoms of the patient.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

The susceptibility of a particular cell to treatment with the compounds according to the invention can be determined by in vitro tests. Typically, a culture of the cell is combined with a compound according to the invention at various concentrations for a period of time which is sufficient to allow the active agents to induce cell death or to inhibit migration, usually between about one hour and one week. In vitro testing can be carried out using cultivated cells from a biopsy sample. The viable cells remaining after the treatment are then counted.

The dose varies depending on the specific compound used, the specific disease, the patient status, etc. A therapeutic dose is typically sufficient considerably to reduce the undesired cell population in the target tissue while the viability of the patient is maintained. The treatment is generally continued until a considerable reduction has occurred, for example an at least about 50% reduction in the cell burden, and may be continued until essentially no more undesired cells are detected in the body.

For identification of a signal transduction pathway and for detection of interactions between various signal transduction pathways, various scientists have developed suitable models or model systems, for example cell culture models (for example Khwaja et al., EMBO, 1997, 16, 2783-93) and models of transgenic animals (for example White et al., Oncogene, 2001, 20, 7064-7072). For the determination of certain stages in the signal transduction cascade, interacting compounds can be utilised in order to modulate the signal (for example Stephens et al., Biochemical J., 2000, 351, 95-105). The compounds according to the invention can also be used as reagents for testing kinase-dependent signal transduction pathways in animals and/or cell culture models or in the clinical diseases mentioned in this application.

Measurement of the kinase activity is a technique which is well known to the person skilled in the art. Generic test systems for the determination of the kinase activity using substrates, for example histone (for example Alessi et al., FEBS Lett. 1996, 399, 3, pages 333-338) or the basic myelin protein, are described in the literature (for example Campos-Gonzalez, R. and Glenney, Jr., J. R. 1992, J. Biol. Chem. 267, page 14535).

For the identification of kinase inhibitors, various assay systems are available. In scintillation proximity assay (Sorg et al., J. of. Biomolecular Screening, 2002, 7, 11-19) and flashplate assay, the radioactive phosphorylation of a protein or peptide as substrate with γATP is measured. In the presence of an inhibitory compound, a decreased radioactive signal, or none at all, is detectable. Furthermore, homogeneous time-resolved fluorescence resonance energy transfer (HTR-FRET) and fluorescence polarisation (FP) technologies are suitable as assay methods (Sills et al., J. of Biomolecular Screening, 2002, 191-214).

Other non-radioactive ELISA assay methods use specific phospho-antibodies (phospho-ABs). The phospho-AB binds only the phosphorylated substrate. This binding can be detected by chemiluminescence using a second peroxidase-conjugated anti-sheep antibody (Ross et al., 2002, Biochem. J.).

There are many diseases associated with deregulation of cellular proliferation and cell death (apoptosis). The conditions of interest include, but are not limited to, the following. The compounds according to the invention are suitable for the treatment of various conditions where there is proliferation and/or migration of smooth muscle cells and/or inflammatory cells into the intimal layer of a vessel, resulting in restricted blood flow through that vessel, for example in the case of neointimal occlusive lesions. Occlusive graft vascular diseases of interest include atherosclerosis, coronary vascular disease after grafting, vein graft stenosis, peri-anastomatic prosthetic restenosis, restenosis after angioplasty or stent placement, and the like.

PRIOR ART REGARDING MET KINASE INHIBITORS

Thiadiazinones are disclosed in WO 03/037349.
4,5-Dihydropyrazoles for combating cancer are described in WO 03/079973 A2.
Quinoline derivatives are described in EP 1 411 046 A1.
Pyrrole-indoline derivatives are disclosed in WO 02/096361 A2.
1-Acyldihydropyrazole derivatives are known from WO 2007/019933.
Pyridazinone derivatives are described in WO 2006/010668.
Substituted 5-phenyl-3,6-dihydro-2-oxo-6H-1,3,4-thiadiazines are known from WO 2006/010285.
3,6-Dihydro-2-oxo-6H-1,3,4-thiadiazine derivatives are described in WO 2006/010286.
In addition, other Met kinase inhibitors are known from WO 2005/004607, WO 2005/030140, WO 2006/014325, WO 2006/021881 and WO 2006/021881.

SUMMARY OF THE INVENTION

The invention relates to compounds of the formula I in which
E, E', E'', E''' each, independently of one another, denote C or N,
$R^1$, $R^2$ each, independently of one another, denote H or A,
$R^1$ and $R^2$ together also denote $(CH_2)_p$, in which 1 or 2 $CH_2$ group(s) may be replaced by O and/or NH,
$R^3$ denotes H, $(CH_2)_n CONH_2$, $(CH_2)_n CONHA$, $(CH_2)_n CONAA'$, A, COA, OH, OA, $CONH(CH_2)_m NH_2$, $CONH(CH_2)_m NHA$, $CONH(CH_2)_m NAA'$, $CO(CH_2)_m NH_2$, $CO(CH_2)_m NHA$, $CO(CH_2)_m NAA'$, $CO(CH_2)_m Het$, CH(OH)A, CN, Het, Hal, $CONH(CH_2)_m NA\text{-}COOA$, $SO_2 A$, $NH(CH_2)_m NH_2$, $NH(CH_2)_m NHA$, $NH(CH_2)_m NAA'$, $(CH_2)_n COOH$, $(CH_2)_n COOA$, $O(CH_2)_m NH_2$, $O(CH_2)_m NHA$, $O(CH_2)_m NAA'$, OHet, N=CH—NAA', N=CH—NHA, N=CH—NH$_2$, $O(CH_2)_m Het$, $O(CH_2)_m OH$, $O(CH_2)_m OA$, $SO_2(CH_2)_m OH$, $OCH(A)CH_2 Het$, $OCH_2 CH(OH)CH_2 NHA$, $OCH_2 C(AA')CH_2 NAA'$, $OCH_2 CH(A)CH_2 NAA'$, $OCH_2 CH(OH)CH_2 OH$, $O(CH_2)_m CONAA'$ or $O(CH_2)_m COHet$,
$R^{3'}$ denotes H or Hal,
$R^4$ denotes $Het^1$, $NHCOOR^5$, $NHCONHR^5$, $NHCONHR^5$, $NO_2$ or NHCOA,
$R^{4'}$ denotes H or Hal,
$R^4$ and $R^{4'}$ together also denote NHCONH,
$R^5$ denotes A, $(CH_2)_m NH_2$, $(CH_2)_m NHA$, $(CH_2)_m NAA'$ or $(CH_2)_m Het$, Het denotes a mono- or bicyclic saturated, unsaturated or aromatic heterocycle having 1 to 4 N, O and/or S atoms, which is unsubstituted or may be mono-, di- or trisubstituted by Hal, A, $OR^6$, $N(R^6)_2$, $NO_2$, CN, $COOR^6$, $CON(R^6)_2$, $NR^3COA$, $NR^6SO_2A$, $SO_2N(R^6)_2$, pyridyl, $S(O)_mA$, NHCOOA, $NHCON(R^6)_2$, CHO, COA, =S, =NH, =NA and/or =O (carbonyl oxygen), $Het^1$ denotes a monocyclic aromatic heterocycle having 1 to 4 N, O and/or S atoms, which is unsubstituted or may be mono-, di- or trisubstituted, in each case independently of one another, by $R^3$, $R^6$ denotes H or A, A, A' each, independently of one another, denote unbranched or branched alkyl having 1-10 C atoms,
  in which 1-7 H atoms may be replaced by OH, F, Cl and/or Br,
  and/or in which one or two $CH_2$ groups may be replaced by O, S, SO, $SO_2$ and/or CH=CH groups, or
  cyclic alkyl having 3-7 C atoms, Hal denotes F, Cl, Br or m denotes 1, 2, 3 or 4, n denotes 0, 1, 2, 3 or 4, p denotes 1, 2, 3, 4 or 5, and, if $R^3$ is bonded to E' and $R^{3'}$ is bonded to E'', $R^3$ and $R^{3'}$ together also denote CH=CH—CH=CH, and pharmaceutically usable derivatives, solvates, salts, tautomers and stereoisomers thereof, including mixtures thereof in all ratios.

The invention also relates to the optically active forms (stereoisomers), the enantiomers, the racemates, the diastereomers and the hydrates and solvates of these compounds. The term solvates of the compounds is taken to mean adductions of inert solvent molecules onto the compounds which form owing to their mutual attractive force. solvates are, for example, mono- or dihydrates or alkoxides.

The term pharmaceutically usable derivatives is taken to mean, for example, the salts of the compounds according to the invention and also so-called prodrug compounds.

The term prodrug derivatives is taken to mean compounds of the formula I which have been modified by means of, for example, alkyl or acyl groups, sugars or oligopeptides and which are rapidly cleaved in the organism to form the effective compounds according to the invention.

These also include biodegradable polymer derivatives of the compounds according to the invention, as described, for example, in Int. J. Pharm. 115, 61-67 (1995).

The expression "effective amount" denotes the amount of a medicament or of a pharmaceutical active ingredient which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence:
improved treatment, healing, prevention or elimination of a disease, syndrome, condition, complaint, disorder or side-effects or also the reduction in the advance of a disease, complaint or disorder.

The expression "therapeutically effective amount" also encompasses the amounts which are effective for increasing normal physiological function.

The invention also relates to the use of mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

The invention relates to the compounds of the formula I and salts thereof and to a process for the preparation of compounds of the formula I according to Claims 1-11 and pharmaceutically usable derivatives, salts, solvates, tautomers and stereoisomers thereof, characterised in that a) a compound of the formula II

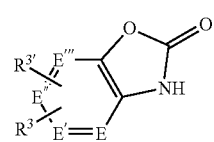

in which E, E', E'', E''', $R^3$ and $R^{3'}$ have the meanings indicated in Claim 1,
is reacted with a compound of the formula III

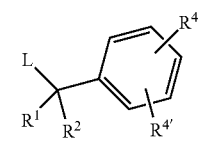

in which $R^1$, $R^2$, $R^4$ and $R^{4'}$ have the meanings indicated in Claim 1 and L denotes Cl, Br, I or a free or reactively functionally modified OH group,
or
b) a radical $R^3$ and/or $R^4$ is converted into another radical $R^3$ and/or $R^4$ by
  i) acylating an amino group,
  ii) converting a carboxyl group into an amide,
and/or
a base or acid of the formula I is converted into one of its salts.

Above and below, the radicals $R^1$, $R^2$, $R^3$, $R^{3'}$, $R^4$, $R^{4'}$, E, E', E'' and E''' have the meanings indicated for the formula I, unless expressly stated otherwise.

Abbreviations:
TEA trifluoroacetic acid
DCM dichloromethane

A, A' denote, in each case independently of one another, alkyl, is unbranched (linear) or branched, and has 1, 2, 3, 4, 5, 6, 7, 8, 9 or 10 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl. A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

Cyclic alkyl (cycloalkyl) preferably denotes cyclopropyl, cyclobutyl, cyclopentyl, cyclohexyl or cycloheptyl.

Irrespective of further substitutions, Het denotes, for example, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-iso-indolyl, indazolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4-, -5-yl or 2,1,3-benzoxadiazol-5-yl or dibenzofuranyl.

The heterocyclic radicals may also be partially or fully hydrogenated. Irrespective of further substitutions, Het can thus also denote, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)phenyl or also 3,4-dihydro-2H-1,5-benzodioxepin-6- or -7-yl, furthermore preferably 2,3-dihydrobenzofuranyl, 2,3-dihydro-2-oxofuranyl, 3,4-dihydro-2-oxo-1H-quinazolinyl, 2,3-dihydrobenzoxazolyl, 2-oxo-2,3-dihydrobenzoxazolyl, 2,3-dihydrobenzimidazolyl, 1,3-dihydroindole, 2-oxo-1,3-dihydroindole or 2-oxo-2,3-dihydrobenzimidazolyl.

In a further embodiment, Het preferably denotes a mono- or bicyclic saturated, unsaturated or aromatic heterocycle having 1 to 3 N, O and/or S atoms, which is unsubstituted or may be mono-, di- or disubstituted by A, pyridyl and/or $=$O (carbonyl oxygen).

Het particularly preferably denotes piperidinyl, pyrrolidinyl, morpholin-4-yl, piperazinyl, 1,3-oxazolidin-3-yl, imidazolidinyl, oxazolyl, oxadiazolyl, thiazolyl, thienyl, furanyl, pyridyl, 1-azabicyclo[2.2.2]oct-3-yl, pyridazinyl, dihydropyridazinyl or pyrazolyl, where the radicals may also be mono- or disubstituted by A, pyridyl and/or $=$O (carbonyl oxygen).

Irrespective of further substitutions, $Het^1$ denotes, for example, 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or -5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl or pyrazinyl.

$Het^1$ particularly preferably denotes 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl or pyrazinyl, each of which is unsubstituted or mono- or disubstituted by A, $O(CH_2)_mNH_2$, $O(CH_2)_mNHA$, $O(CH_2)_mNAA'$, Het, OHet, $N=CH-NAA'$, $N=CH-NHA$, $N=CH-NH_2$, $O(CH_2)_mHet$, $OCH(A)CH_2Het$, $OCH_2CH(OH)CH_2NHA$, $O(CH_2)_mCOHet$, $O(CH_2)_mCONAA'$, $OCH_2C(AA')CH_2NAA'$, $OCH_2CH(A)CH_2NAA'$, $OCH_2CH(OH)CH_2OH$ and/or $CONH(CH_2)_mNAA'$.

E denotes C or N; E', E'', E''' preferably denote C.

$R^6$ preferably denotes H, methyl, ethyl, propyl, isopropyl, butyl or tert-butyl.

Hal preferably denotes F, Cl or Br, but also I, particularly preferably F or Cl.

Throughout the invention, all radicals which occur more than once may be identical or different, i.e. are independent of one another.

The compounds of the formula I may have one or more chiral centres and can therefore occur in various stereoisomeric forms. The formula I encompasses all these forms.

Accordingly, the invention relates, in particular, to the compounds of the formula I in which at least one of the said radicals has one of the preferred meanings indicated above. Some preferred groups of compounds may be expressed by the following sub-formulae Ia to Ig, which conform to the formula I and in which the radicals not designated in greater detail have the meaning indicated for the formula I, but in which in Ia A, A' each, independently of one another, denote unbranched or branched alkyl having 1-10 C atoms,
in which 1-7 H atoms may be replaced by OH, F and/or Cl,
in Ib Het denotes a mono- or bicyclic saturated, unsaturated or aromatic heterocycle having 1 to 3 N, O and/or S atoms, which is unsubstituted or may be mono-, di- or trisubstituted by A, pyridyl and/or $=$O (carbonyl oxygen);
in Ic $Het^1$ denotes 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, 1,2,3-triazol-1-, -4- or -5-yl. 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl or pyrazinyl, each of which is unsubstituted or mono- or disubstituted by A, $O(CH_2)_mNH_2$, $O(CH_2)_mNHA$, $O(CH_2)_mNAA'$, Het, OHet, $N=CH-NAA'$, $N=CH-NHA$, $N=CH-NH_2$, $O(CH_2)_mHet$, $OCH(A)CH_2Het$, $OCH_2CH(OH)CH_2NHA$, $O(CH_2)_mCOHet$, $O(CH_2)_mCONAA'$, $OCH_2C(AA')CH_2NAA'$, $OCH_2CH(A)CH_2NAA'$, $OCH_2CH(OH)CH_2OH$ and/or $CONH(CH_2)_mNAA'$;
in Id Het denotes piperidinyl, pyrrolidinyl, morpholin-4-yl, piperazinyl, 1,3-oxazolidin-3-yl, imidazolidinyl, oxazolyl, oxadiazolyl, thiazolyl, thienyl, furanyl, pyridyl, 1-azabicyclo[2.2.2]oct-3-yl, pyridazinyl, dihydropyridazinyl or pyrazolyl,
where the radicals may also be mono- or disubstituted by A, pyridyl and/or $=$O (carbonyl oxygen);
in Ie E denotes C or N,
E', E'', E''' denote C;

in If $R^6$ denotes H, methyl, ethyl, propyl, isopropyl, butyl or tertbutyl;

in Ig E denotes C or N,

E', E''', E''' denote C, $R^1$, $R^2$ each, independently of one another, denote H or A, $R^3$ denotes H, $(CH_2)_n CONH_2$, $(CH_2)_n CONHA$, $(CH_2)_n CONAA'$, A, COA, OH, OA, CONH$(CH_2)_m NH_2$, CONH$(CH_2)_m NHA$, CONH$(CH_2)_m NAA'$, CO$(CH_2)_m NH_2$, CO$(CH_2)_m NHA$, CO$(CH_2)_m NAA'$, CO$(CH_2)_m Het$, CH(OH)A, CN, Het, Hal, CONH$(CH_2)_m NA$-COOA, $SO_2A$, NH$(CH_2)_m NH_2$, NH$(CH_2)_m NHA$, NH$(CH_2)_m NAA'$, $(CH_2)_n COOH$, $(CH_2)_n COOA$, O$(CH_2)_m NH_2$, O$(CH_2)_m NHA$, O$(CH_2)_m NAA'$, OHet, N=CH—NAA', N=CH—NHA, N=CH—$NH_2$, O$(CH_2)_m Het$, $SO_2(CH_2)_m OH$, O$(CH_2)_m OH$ or O$(CH_2)_m OA$, $R^{3'}$ denotes H or Hal, $R^4$ denotes $Het^1$, $NO_2$, NHCOA, NHCOOR$^5$, NHCONHR$^5$ or NHCOCONHR$^5$, $R^{4'}$ denotes H or Hal, $R^4$ and $R^{4'}$ together also denote NHCONH, $R^5$ denotes A, $(CH_2)_m NH_2$, $(CH_2)_m NHA$, $(CH_2)_m NAA'$ or $(CH_2)_m Het$, Het denotes piperidinyl, pyrrolidinyl, morpholin-4-yl, piperazinyl, 1,3-oxazolidin-3-yl, imidazolidinyl, oxazolyl, oxadiazolyl, thiazolyl, thienyl, furanyl, pyridyl, 1-azabicyclo[2.2.2]oct-3-yl, pyridazinyl, dihydropyridazinyl or pyrazolyl, where the radicals may also be mono- or disubstituted by A, pyridyl and/or =O (carbonyl oxygen), $Het^1$ denotes 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl or pyrazinyl, each of which is unsubstituted or mono- or disubstituted by A, O$(CH_2)_m NH_2$, O$(CH_2)_m NHA$, O$(CH_2)_m NAA'$, Het, OHet, N=CH—NAA', N=CH—NHA, N=CH—$NH_2$, O$(CH_2)_m Het$, OCH$_2$(A)CH$_2$Het, OCH$_2$CH(OH)CH$_2$NHA, O$(CH_2)_m$COHet, O$(CH_2)_m$CONAA', OCH$_2$C(AA')CH$_2$NAA', OCH$_2$CH(A)CH$_2$NAA', OCH$_2$CH(OH)CH$_2$OH and/or CONH$(CH_2)_m NAA'$, A, A' each, independently of one another, denote unbranched or branched alkyl having 1-10 C atoms, in which 1-7 H atoms may be replaced by OH, F and/or Cl, Hal denotes F, Cl, Br or I, m denotes 1, 2, 3 or 4, n denotes 0, 1, 2, 3 or 4, and, if $R^3$ is bonded to E' and $R^{3'}$ is bonded to E''', $R^3$ and $R^{3'}$ together also denote CH=CH—CH=CH, and pharmaceutically usable derivatives, salts, solvates, tautomers and stereoisomers thereof, including mixtures thereof in all ratios.

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail.

The starting compounds of the formulae II and III are generally known. If they are novel, however, they can be prepared by methods known per se.

Compounds of the formula I can preferably be obtained by reacting a compound of the formula II with a compound of the formula III.

In the compounds of the formula III, L preferably denotes Cl, Br, or a free or reactively modified OH group, such as, for example, an activated ester, an imidazolide or alkylsulfonyloxy having 1-6 C atoms (preferably methylsulfonyloxy or trifluoromethylsulfonyloxy) or arylsulfonyloxy having 6-10 C atoms (preferably phenyl- or p-tolylsulfonyloxy).

The reaction is generally carried out in the presence of an acid-binding agent, preferably an organic base, such as DIPEA, triethylamine, dimethylaniline, pyridine or quinoline.

The addition of an alkali or alkaline earth metal hydroxide, carbonate or bicarbonate or another salt of a weak acid of the alkali or alkaline earth metals, preferably of potassium, sodium, calcium or caesium, may also be favourable.

Depending on the conditions used, the reaction time is between a few minutes and 14 days, the reaction temperature is between about −30° and 140°, normally between −10° and 90°, in particular between about 0° and about 70°.

Examples of suitable inert solvents are hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide, 1-methylpyrrolidinone (NMP) or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents. Particular preference is given to acetonitrile, dichloromethane, NMP and/or DMF.

It is furthermore possible to convert a compound of the formula I into another compound of the formula I by converting a radical $R^3$ and/or $R^4$ into another radical $R^3$ and/or $R^4$.

For example, free amino groups can be acylated in a conventional manner using an acid chloride or anhydride, advantageously in an inert solvent, such as dichloromethane or THF, and/or in the presence of a base, such as triethylamine or pyridine, at temperatures between −60° and +30°. Furthermore, an oxyamidine derivative can be cyclised to give an oxadiazole derivative, preferably in THF using the Burgess reagent at temperatures between 60° and 80°.

A carboxylic acid can also be converted into a carboxamide under standard conditions, preferably by reaction with an amine.

It is furthermore possible to convert a compound of the formula I into another compound of the formula I by converting a radical $R^4$ into another radical $R^4$, for example by reducing nitro groups to amino groups (for example by hydrogenation on Raney nickel or Pd/carbon in an inert solvent, such as methanol or ethanol).

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine (tromethamine), but this is not intended to represent a restriction.

Compounds of the present invention which contain basic nitrogen-containing groups can be quaternised using agents such as ($C_1$-$C_4$)alkyl halides, for example methyl, ethyl, isopropyl and tert-butyl chloride, bromide and iodide; di($C_1$-$C_4$) alkyl sulfates, for example dimethyl, diethyl and diamyl sulfate; ($C_{10}$-$C_{18}$)alkyl halides, for example decyl, dodecyl, lauryl, myristyl and stearyl chloride, bromide and iodide; and aryl($C_1$-$C_4$)alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

Particular preference is given to hydrochloride, dihydrochloride, hydrobromide, maleate, mesylate, phosphate, sulfate and succinate.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound of the formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

The invention furthermore relates to medicaments comprising at least one compound of the formula I and/or pharmaceutically usable derivatives, solvates and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tabletting machine, giving lumps of nonuniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a prespecified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula I and salts, solvates and physiologically functional derivatives thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula I and the salts, solvates and physiologically functional derivatives thereof can also be delivered using monoclonal anti-bodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose.

Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I depends on a number of factors, including, for example, the age and weight of the animal, the precise condition that requires treatment, and its severity, the nature of the formulation and the method of administration, and is ultimately determined by the treating doctor or vet. However, an effective amount of a compound according to the invention for the treatment of neoplastic growth, for example colon or breast carcinoma, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The invention furthermore relates to medicaments comprising at least one compound of the formula I and/or pharmaceutically usable derivatives, solvates and stereoisomers thereof, including mixtures thereof in all ratios, and at least one further medicament active ingredient.

The invention also relates to a set (kit) consisting of separate packs of (a) an effective amount of a compound of the formula I and/or pharmaceutically usable derivatives, solvates and stereoisomers thereof, including mixtures thereof in all ratios, and (b) an effective amount of a further medicament active ingredient.

The set comprises suitable containers, such as boxes, individual bottles, bags or ampoules. The set may, for example, comprise separate ampoules, each containing an effective amount of a compound of the formula I and/or pharmaceutically usable derivatives, solvates and stereoisomers thereof, including mixtures thereof in all ratios, and an effective amount of a further medicament active ingredient in dissolved or lyophilised form.

Use

The present compounds are suitable as pharmaceutical active ingredients for mammals, especially for humans, in the treatment of tyrosine kinase-induced diseases. These diseases include the proliferation of tumour cells, pathological neovascularisation (or angiogenesis) which promotes the growth of solid tumours, ocular neovascularisation (diabetic retinopathy, age-induced macular degeneration and the like) and inflammation (psoriasis, rheumatoid arthritis and the like).

The present invention encompasses the use of the compounds of the formula I and/or physiologically acceptable salts and solvates thereof for the preparation of a medicament for the treatment or prevention of cancer. Preferred carcinomas for the treatment originate from the group cerebral carcinoma, urogenital tract carcinoma, carcinoma of the lymphatic system, stomach carcinoma, laryngeal carcinoma and lung carcinoma. A further group of preferred forms of cancer are monocytic leukaemia, lung adenocarcinoma, small-cell lung carcinomas, pancreatic cancer, glioblastomas and breast carcinoma.

Also encompassed is the use of the compounds according to Claim 1 according to the invention and/or physiologically acceptable salts and solvates thereof for the preparation of a medicament for the treatment or prevention of a disease in which angiogenesis is implicated.

Such a disease in which angiogenesis is implicated is an ocular disease, such as retinal vascularisation, diabetic retinopathy, age-induced macular degeneration and the like.

The use of compounds of the formula I and/or physiologically acceptable salts and solvates thereof for the preparation of a medicament for the treatment or prevention of inflammatory diseases also falls within the scope of the present invention. Examples of such inflammatory diseases include rheumatoid arthritis, psoriasis, contact dermatitis, delayed hypersensitivity reaction and the like.

Also encompassed is the use of the compounds of the formula I and/or physiologically acceptable salts and solvates thereof for the preparation of a medicament for the treatment or prevention of a tyrosine kinase-induced disease or a tyrosine kinase-induced condition in a mammal, in which to this method a therapeutically effective amount of a compound according to the invention is administered to a sick mammal in need of such treatment. The therapeutic amount varies according to the specific disease and can be determined by the person skilled in the art without undue effort.

The present invention also encompasses the use compounds of the formula I and/or physiologically acceptable salts and solvates thereof for the preparation of a medicament for the treatment or prevention of retinal vascularisation.

Methods for the treatment or prevention of ocular diseases, such as diabetic retinopathy and age-induced macular degeneration, are likewise part of the invention. The use for the treatment or prevention of inflammatory diseases, such as rheumatoid arthritis, psoriasis, contact dermatitis and delayed hypersensitivity reaction, as well as the treatment or prevention of bone pathologies from the group osteosarcoma, osteoarthritis and rickets, likewise falls within the scope of the present invention.

The expression "tyrosine kinase-induced diseases or conditions" refers to pathological conditions that depend on the activity of one or more tyrosine kinases. Tyrosine kinases either directly or indirectly participate in the signal transduction pathways of a variety of cellular activities, including proliferation, adhesion and migration and differentiation. Diseases associated with tyrosine kinase activity include proliferation of tumour cells, pathological neovascularisation that promotes the growth of solid tumours, ocular neovascularisation (diabetic retinopathy, age-induced macular degeneration and the like) and inflammation (psoriasis, rheumatoid arthritis and the like).

The compounds of the formula I can be administered to patients for the treatment of cancer, in particular fast-growing tumours.

The invention thus relates to the use of compounds of the formula I, and pharmaceutically usable derivatives, solvates and stereoisomers thereof, including mixtures thereof in all ratios, for the preparation of a medicament for the treatment of diseases in which the inhibition, regulation and/or modulation of kinase signal transduction plays a role.

Preference is given here to Met kinase.

Preference is given to the use of compounds of the formula I, and pharmaceutically usable derivatives, solvates and stereoisomers thereof, including mixtures thereof in all ratios, for the preparation of a medicament for the treatment of diseases which are influenced by inhibition of tyrosine kinases by the compounds according to Claim 1.

Particular preference is given to the use for the preparation of a medicament for the treatment of diseases which are influenced by inhibition of Met kinase by the compounds according to Claim 1.

Especial preference is given to the use for the treatment of a disease where the disease is a solid tumour.

The solid tumour is preferably selected from the group of tumours of the lung, squamous epithelium, the bladder, the stomach, the kidneys, of head and neck, the oesophagus, the cervix, the thyroid, the intestine, the liver, the brain, the prostate, the urogenital tract, the lymphatic system, the stomach and/or the larynx.

The solid tumour is furthermore preferably selected from the group lung adenocarcinoma, small-cell lung carcinomas, pancreatic cancer, glioblastomas, colon carcinoma and breast carcinoma.

Preference is furthermore given to the use for the treatment of a tumour of the blood and immune system, preferably for the treatment of a tumour selected from the group of acute myeloid leukaemia, chronic myeloid leukaemia, acute lymphatic leukaemia and/or chronic lymphatic leukaemia.

The disclosed compounds of the formula I can be administered in combination with other known therapeutic agents, including anticancer agents. As used here, the term "anticancer agent" relates to any agent which is administered to a patient with cancer for the purposes of treating the cancer.

The anti-cancer treatment defined herein may be applied as a sole therapy or may involve, in addition to the compound of the invention, conventional surgery or radiotherapy or chemotherapy. Such chemotherapy may include one or more of the following categories of anti-tumour agents:

(i) antiproliferative/antineoplastic/DNA-damaging agents and combinations thereof, as used in medical oncology, such as alkylating agents (for example cis-platin, carboplatin, cyclophosphamide, nitrogen mustard, melphalan, chloroambucil, busulphan and nitrosoureas); antimetabolites (for example antifolates such as fluoropyrimidines like 5-fluorouracil and tegafur, raltitrexed, methotrexate, cytosine arabinoside, hydroxyurea and gemcitabine); antitumour antibiotics (for example anthracyclines, like adriamycin, bleomycin, doxorubicin, daunomycin, epirubicin, idarubicin, mitomycin-C, dactinomycin and mithramycin); antimitotic agents (for example vinca alkaloids, like vincristine, vinblastine, vindesine and vinorelbine, and taxoids, like taxol and taxotere); topoisomerase inhibitors (for example epipodophyllotoxins, like etoposide and teniposide, amsacrine, topotecan, irinotecan and camptothecin) and cell-differentiating agents (for example all-trans-retinoic acid, 13-cis-retinoic acid and fenretinide), (ii) cytostatic agents, such as antioestrogens (for example tamoxifen, toremifene, raloxifene, droloxifene and iodoxyfene), oestrogen receptor downregulators (for example fulvestrant), antiandrogens (for example bicalutamide, flutamide, nilutamide and cyproterone acetate), LHRH antagonists or LHRH agonists (for example goserelin, leuprorelin and buserelin), progesterones (for example megestrol acetate), aromatase inhibitors (for example as anastrozole, letrozole, vorazole and exemestane) and inhibitors of 5α-reductase, such as finasteride;

(iii) agents which inhibit cancer cell invasion (for example metalloproteinase inhibitors, like marimastat, and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors, such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family;

(v) antiangiogenic agents, such as those which inhibit the effects of vascular endothelial growth factor, (for example the anti-vascular endothelial cell growth factor antibody bevacizumab [Avastin™], compounds such as those disclosed in published international patent applications WO 97/22596, WO 97/30035, WO 97/32856 and WO 98/13354) and compounds that work by other mechanisms (for example linomide, inhibitors of integrin αvβ3 function and angiostatin);

(vi) vessel-damaging agents, such as combretastatin A4 and compounds disclosed in international patent applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-Ras antisense;

(viii) gene therapy approaches, including, for example, approaches for replacement of aberrant genes, such as aberrant p53 or aberrant BRCA1 or BRCA2, GDEPT (gene-directed enzyme pro-drug therapy) approaches, such as those using cytosine deaminase, thymidine kinase or a bacterial nitroreductase enzyme, and approaches for increasing patient tolerance to chemotherapy or radiotherapy, such as multi-drug resistance gene therapy; and (ix) immunotherapy approaches, including, for example, ex-vivo and in-vivo approaches for increasing the immunogenicity of patient tumour cells, such as transfection with cytokines, such as interleukin 2, interleukin 4 or granulocyte-macrophage colony stimulating factor, approaches for decreasing T-cell anergy, approaches using transfected immune cells, such as cytokine-transfected dendritic cells, approaches using cytokine-transfected tumour cell lines, and approaches using anti-idiotypic antibodies.

The medicaments from Table 1 below are preferably, but not exclusively, combined with the compounds of the formula I.

TABLE 1

| | | |
|---|---|---|
| Alkylating agents | Cyclophosphamide | Lomustine |
| | Busulfan | Procarbazine |
| | Ifosfamide | Altretamine |
| | Melphalan | Estramustine phosphate |
| | Hexamethylmelamine | Mechloroethamine |
| | Thiotepa | Streptozocin |
| | chloroambucil | Temozolomide |
| | Dacarbazine | Semustine |
| | Carmustine | |
| Platinum agents | Cisplatin | Carboplatin |
| | Oxaliplatin | ZD-0473 (AnorMED) |
| | Spiroplatin | Lobaplatin (Aeterna) |
| | Carboxyphthalatoplatinum | Satraplatin (Johnson Matthey) |
| | Tetraplatin | BBR-3464 |
| | Ormiplatin | (Hoffmann-La Roche) |
| | Iproplatin | SM-11355 (Sumitomo) |
| | | AP-5280 (Access) |
| Antimetabolites | Azacytidine | Tomudex |
| | Gemcitabine | Trimetrexate |
| | Capecitabine | Deoxycoformycin |
| | 5-fluorouracil | Fludarabine |
| | Floxuridine | Pentostatin |
| | 2-chlorodesoxyadenosine | Raltitrexed |
| | 6-Mercaptopurine | Hydroxyurea |
| | 6-Thioguanine | Decitabine (SuperGen) |
| | Cytarabine | Clofarabine (Bioenvision) |
| | 2-fluorodesoxycytidine | Irofulven (MGI Pharma) |
| | Methotrexate | DMDC (Hoffmann-La Roche) |
| | Idatrexate | Ethynyloytidine (Taiho) |
| Topoisomerase inhibitors | Amsacrine | Rubitecan (SuperGen) |
| | Epirubicin | Exatecan mesylate (Daiichi) |
| | Etoposide | Quinamed (ChemGenex) |
| | Teniposide or mitoxantrone | Gimatecan (Sigma-Tau) |
| | Irinotecan (CPT-11) | Difiomotecan (Beaufour-Ipsen) |
| | 7-ethyl-10-hydroxycamptothecin | TAS-103 (Taiho) |
| | Topotecan | Elsamitrucin (Spectrum) |
| | Dexrazoxanet | J-107088 (Merck & Co) |

TABLE 1-continued

| | | |
|---|---|---|
| | (TopoTarget) | BNP-1350 (BioNumerik) |
| | Pixantrone (Novuspharma) | CKD-602 (Chong Kun Dang) |
| | Rebeccamycin analogue (Exelixis) | KW-2170 (Kyowa Hakko) |
| | BBR-3576 (Novuspharma) | |
| Antitumour antibiotics | Dactinomycin (Actinomycin D) | Amonafide |
| | Doxorubicin (Adriamycin) | Azonafide |
| | Deoxyrubicin | Anthrapyrazole |
| | Valrubicin | Oxantrazole |
| | Daunorubicin (Daunomycin) | Losoxantrone |
| | Epirubicin | Bleomycin sulfate (Blenoxan) |
| | Therarubicin | Bleomycinic acid |
| | Idarubicin | Bleomycin A |
| | Rubidazon | Bleomycin B |
| | Plicamycinp | Mitomycin C |
| | Porfiromycin | MEN-10755 (Menarini) |
| | Cyanomorpholinodoxo-rubicin | GPX-100 (Gem Pharmaceuticals) |
| | Mitoxantron (Novantron) | |
| Antimitotic agents | Paclitaxel | SB 408075 (GlaxoSmithKline) |
| | Docetaxel | |
| | Colchicine | E7010 (Abbott) |
| | Vinblastine | PG-TXL (Cell Therapeutics) |
| | Vincristine | |
| | Vinorelbine | IDN 5109 (Bayer) |
| | Vindesine | A 105972 (Abbott) |
| | Dolastatin 10 (NCI) | A 204197 (Abbott) |
| | Rhizoxin (Fujisawa) | LU 223651 (BASF) |
| | Mivobulin (Warner-Lambert) | D 24851 (ASTA Medica) |
| | | ER-86526 (Eisai) |
| | Cemadotin (BASF) | Combretastatin A4 (BMS) |
| | RPR 109881A (Aventis) | Isohomohalichondrin-B (PharmaMar) |
| | TXD 258 (Aventis) | |
| | Epothilone B (Novartis) | ZD 6126 (AstraZeneca) |
| | T 900607 (Tularik) | PEG-Paclitaxel (Enzon) |
| | T 138067 (Tularik) | AZ10992 (Asahi) |
| | Cryptophycin 52 (Eli Lilly) | !DN-5109 (Indena) |
| | Vinflunine (Fabre) | AVLB (Prescient NeuroPharma) |
| | Auristatin PE (Teikoku Hormone) | Azaepothilon B (BMS) |
| | BMS 247550 (BMS) | BNP-7787 (BioNumerik) |
| | BMS 184476 (BMS) | CA-4-prodrug (OXiGENE) |
| | BMS 188797 (BMS) | Dolastatin-10 (NrH) |
| | Taxoprexin (Protarga) | CA-4 (OXiGENE) |
| Aromatase inhibitors | Aminoglutethimide | Exemestan |
| | Letrozole | Atamestan (BioMedicines) |
| | Anastrazole | YM-511 (Yamanouchi) |
| | Formestan | |
| Thymidylate synthase inhibitors | Pemetrexed (Eli Lilly) | Nolatrexed (Eximias) |
| | ZD-9331 (BTG) | CoFactor™ (BioKeys) |
| DNA antagonists | Trabectedin (PharmaMar) | Mafosfamide (Baxter International) |
| | Glufosfamide (Baxter International) | Apaziquone (Spectrum Pharmaceuticals) |
| | Albumin + 32P (Isotope Solutions) | O6-benzylguanine (Paligent) |
| | Thymectacin (NewBiotics) | |
| | Edotreotid (Novartis) | |
| Farnesyl transferase inhibitors | Arglabin (NuOncology Labs) | Tipifarnib (Johnson & Johnson) |
| | Ionafarnib (Schering-Plough) | Perillyl alcohol (DOR BioPharma) |
| | BAY-43-9006 (Bayer) | |
| Pump inhibitors | CBT-1 (CBA Pharma) | Zosuquidar trihydrochloride (Eli Lilly) |
| | Tariquidar (Xenova) | |
| | MS-209 (Schering AG) | Biricodar dicitrate (Vertex) |
| Histone acetyl transferase inhibitors | Tacedinaline (Pfizer) | Pivaloyloxymethyl butyrate (Titan) |
| | SAHA (Aton Pharma) | |
| | MS-275 (Schering AG) | Depsipeptide (Fujisawa) |
| Metalloproteinase inhibitors | Neovastat (Aeterna Laboratories) | CMT-3 (CollaGenex) |
| | Marimastat (British Biotech) | BMS-275291 (Celltech) |
| Ribonucleoside reductase inhibitors | Gallium maltolate (Titan) | Tezacitabine (Aventis) |
| | Triapin (Vion) | Didox (Molecules for Health) |

TABLE 1-continued

| | | |
|---|---|---|
| TNF-alpha agonists/ antagonists | Virulizin (Lorus Therapeutics) CDC-394 (Celgene) | Revimid (Celgene) |
| Endothelin-A receptor antagonists | Atrasentan (Abbot) ZD-4054 (AstraZeneca) | YM-598 (Yamanouchi) |
| Retinoic acid receptor agonists | Fenretinide (Johnson & Johnson) LGD-1550 (Ligand) | Alitretinoin (Ligand) |
| Immunomodulators | Interferon Oncophage (Antigenics) GMK (Progenics) Adenocarcinoma vaccine (Biomira) CTP-37 (AVI BioPharma) JRX-2 (Immuno-Rx) PEP-005 (Peplin Biotech) Synchrovax vaccines (CTL Immune) Melanoma vaccine (CTL Immuno) p21-RAS vaccine (Gem-Vax) | Dexosome therapy (Anosys) Pentrix (Australian Cancer Technology) JSF-154 (Tragen) Cancer vaccine (Intercell) Norelin (Biostar) BLP-25 (Biomira) MGV (Progenies) !3-Alethin (Dovetail) CLL-Thera (Vasogen) |
| Hormonal and antihormonal agents | Oestrogens Conjugated oestrogens Ethynyloestradiol chlorotrianisene Idenestrol Hydroxyprogesterone caproate Medroxyprogesterone Testosterone Testosterone propionate Fluoxymesterone Methyltestosterone Diethylstilbestrol Megestrol Tamoxifen Toremofin Dexamethasone | Prednisone Methylprednisolone Prednisolone Aminoglutethimide Leuprolide Goserelin Leuporelin Bicalutamide Flutamide Octreotide Nilutamide Mitotan P-04 (Novogen) 2-methoxyoestradiol (EntreMed) Arzoxifen (Eli Lilly) |
| Photodynamic agents | Talaporfin (Light Sciences) Theralux (Theratechnologies) Motexafin-Gadolinium (Pharmacyclics) | Pd-Bacteriopheophorbid (Yeda) Lutetium-Texaphyrin (Pharmacyclics) Hypericin |
| Tyrosine kinase inhibitors | Imatinib (Novartis) Leflunomide(Sugen/Pharmacia) ZDI839 (AstraZeneca) Erlotinib (Oncogene Science) Canertjnib (Pfizer) Squalamine (Genaera) SU5416 (Pharmacia) SU6668 (Pharmacia) ZD4190 (AstraZeneca) ZD6474 (AstraZeneca) Vatalanib (Novartis) PKI166 (Novartis) GW2016 (GlaxoSmith-Kline) EKB-509 (Wyeth) EKB-569 (Wyeth) | Kahalide F (PharmaMar) CEP-701 (Cephalon) CEP-751 (Cephalon) MLN518 (Millenium) PKC412 (Novartis) Phenoxodiol O Trastuzumab (Genentech) C225 (ImClone) rhu-Mab (Genentech) MDX-H210 (Medarex) 2C4 (Genentech) MDX-447 (Medarex) ABX-EGF (Abgenix) IMC-1C11 (ImClone) |
| Various agents | SR-27897 (CCK-A inhibitor, Sanofi-Synthelabo) Tocladesine (cyclic AMP agonist, Ribapharm) Alvocidib (CDK inhibitor, Aventis) CV-247 (COX-2 inhibitor, Ivy Medical) P54 (COX-2 inhibitor, Phytopharm) CapCell ™ (CYP450 stimulant, Bavarian Nordic) GCS-IOO (gal3 antagonist, GlycoGenesys) G17DT immunogen (gastrin inhibitor, Aphton) | BCX-1777 (PNP inhibitor, BioCryst) Ranpirnase (ribonuclease stimulant, Alfacell) Galarubicin (RNA synthesis inhibitor, Dong-A) Tirapazamine (reducing agent, SRI International) N-Acetylcysteine (reducing agent, Zambon) R-Flurbiprofen (NF-kappaB inhibitor, Encore) 3CPA (NF-kappaB inhibitor, Active Biotech) Seocalcitol (vitamin D receptor agonist, Leo) |

TABLE 1-continued

| | | |
|---|---|---|
| | Efaproxiral (oxygenator, Allos Therapeutics) | 131-I-TM-601 (DNA antagonist, TransMolecular) |
| | PI-88 (heparanase inhibitor, Progen) | Eflornithin (ODC inhibitor, ILEX Oncology) |
| | Tesmilifen (histamine antagonist, YM BioSciences) | Minodronic acid (osteoclast inhibitor, Yamanouchi) |
| | Histamine (histamine H2 receptor agonist, Maxim) | Indisulam (p53 stimulant, Eisai) |
| | Tiazofurin (IMPDH inhibitor, Ribapharm) | Aplidin (PPT inhibitor, PharmaMar) |
| | Cilengitide (integrin antagonist, Merck KGaA) | Rituximab (CD20 antibody, Genentech) |
| | SR-31747 (IL-1 antagonist, Sanofi-Synthelabo) | Gemtuzumab (CD33 antibody, Wyeth Ayerst) |
| | CCI-779 (mTOR kinase inhibitor, Wyeth) | PG2 (haematopoiesis promoter, Pharmagenesis) |
| | Exisulind (PDE-V inhibitor, Cell Pathways) | Immunol ™ (triclosan mouthwash, Endo) |
| | CP-461 (PDE-V inhibitor, Cell Pathways) | Triacetyluridine (uridine prodrug, Wellstat) |
| | AG-2037 (GART inhibitor, Pfizer) | SN-4071 (sarcoma agent, Signature BioScience) |
| | WX-UK1 (plasminogen activator inhibitor, Wilex) | TransMID-107 ™ (immunotoxin, KS Biomedix) |
| | PBI-1402 (PMN stimulant, ProMetic LifeSciences) | PCK-3145 (apoptosis promoter, Procyon) |
| | Bortezomib (proteasome inhibitor, Millennium) | Doranidazole (apoptosis promoter, Pola) |
| | SRL-172 (T-cell stimulant, SR Pharma) | CHS-828 (cytotoxic agent, Leo) |
| | TLK-286 (glutathione-S transferase inhibitor, Telik) | Trans-retinic acid (differentiator, NIH) |
| | PT-100 (growth factor agonist, Point Therapeutics) | MX6 (apoptosis promoter, MAXIA) |
| | Midostaurin (PKC inhibitor, Novartis) | |
| Alkylating agents | Cyclophosphamide | Lomustine |
| | Busulfan | Procarbazine |
| | Ifosfamide | Altretamine |
| | Melphalan | Estramustine phosphate |
| | Hexamethylmelamine | Mechloroethamine |
| | Thiotepa | Streptozocin |
| | chloroambucil | Temozolomide |
| | Dacarbazine | Semustine |
| | Carmustine | |
| Platinum agents | Cisplatin | Carboplatin |
| | Oxaliplatin | ZD-0473 (AnorMED) |
| | Spiroplatin | Lobaplatin (Aetema) |
| | Carboxyphthalatoplatinum | Satraplatin (Johnson Matthey) |
| | Tetraplatin | BBR-3464 (Hoffmann-La Roche) |
| | Ormiplatin | SM-11355 (Sumitomo) |
| | Iproplatin | AP-5280 (Access) |
| Antimetabolites | Azacytidine | Tomudex |
| | Gemcitabine | Trimetrexate |
| | Capecitabine | Deoxycoformycin |
| | 5-fluorouracil | Fludarabine |
| | Floxuridine | Pentostatin |
| | 2-chlorodesoxyadenosine | Raltitrexed |
| | 6-Mercaptopurine | Hydroxyurea |
| | 6-Thioguanine | Decitabine (SuperGen) |
| | Cytarabine | Clofarabine (Bioenvision) |
| | 2-fluorodesoxycytidine | Irofulven (MGI Pharma) |
| | Methotrexate | DMDC (Hoffmann-La Roche) |
| | Idatrexate | Ethynylcytidine (Taiho) |
| Topoisomerase inhibitors | Amsacrine | Rubitecan (SuperGen) |
| | Epirubicin | Exatecan mesylate (Daiichi) |
| | Etoposide | Quinamed (ChemGenex) |
| | Teniposide or mitoxantrone | Gimatecan (Sigma-Tau) |
| | Irinotecan (CPT-11) | Diflomotecan (Beaufour-Ipsen) |
| | 7-ethyl-10-hydroxycamptothecin | TAS-103 (Taiho) |
| | Topotecan | Elsamitrucin (Spectrum) |
| | Dexrazoxanet | J-107088 (Merck & Co) |

TABLE 1-continued

| | | |
|---|---|---|
| | (TopoTarget) | BNP-1350 (BioNumerik) |
| | Pixantrone (Novuspharma) | CKD-602 (Chong Kun Dang) |
| | Rebeccamycin analogue (Exelixis) | KW-2170 (Kyowa Hakko) |
| | BBR-3576 (Novuspharma) | |
| Antitumour antibiotics | Dactinomycin (Actinomycin D) | Amonafide |
| | Doxorubicin (Adriamycin) | Azonafide |
| | Deoxyrubicin | Anthrapyrazole |
| | Valrubicin | Oxantrazole |
| | Daunorubicin (Daunomycin) | Losoxantrone |
| | Epirubicin | Bleomycin sulfate (Blenoxan) |
| | Therarubicin | Bleomycinic acid |
| | Idarubicin | Bleomycin A |
| | Rubidazon | Bleomycin B |
| | Plicamycinp | Mitomycin C |
| | Porfiromycin | MEN-10755 (Menarini) |
| | Cyanomorpholinodoxo-rubicin | GPX-100 (Gem Pharmaceuticals) |
| | Mitoxantron (Novantron) | |
| Antimitotic agents | Paclitaxel | SB 408075 (GlaxoSmithKline) |
| | Docetaxel | |
| | Colchicine | E7010 (Abbott) |
| | Vinblastine | PG-TXL (Cell Therapeutics) |
| | Vincristine | |
| | Vinorelbine | IDN 5109 (Bayer) |
| | Vindesine | A 105972 (Abbott) |
| | Dolastatin 10 (NCI) | A 204197 (Abbott) |
| | Rhizoxin (Fujisawa) | LU 223651 (BASF) |
| | Mivobulin (Warner-Lambert) | D 24851 (ASTA Medica) |
| | Cemadotin (BASF) | ER-86526 (Eisai) |
| | RPR 109881A (Aventis) | Combretastatin A4 (BMS) |
| | TXD 258 (Aventis) | Isohomohalichondrin-B (PharmaMar) |
| | Epothilone B (Novartis) | ZD 6126 (AstraZeneca) |
| | T 900607 (Tularik) | PEG-Paclitaxel (Enzon) |
| | T 138067 (Tularik) | AZ10992 (Asahi) |
| | Cryptophycin 52 (Eli Lilly) | !DN-5109 (Indena) |
| | Vinflunine (Fabre) | AVLB (Prescient NeuroPharma) |
| | Auristatin PE (Teikoku Hormone) | Azaepothilon B (BMS) |
| | BMS 247550 (BMS) | BNP-7787 (BioNumerik) |
| | BMS 184476 (BMS) | CA-4-prodrug (OXiGENE) |
| | BMS 188797 (BMS) | Dolastatin-10 (NrH) |
| | Taxoprexin (Protarga) | CA-4 (OXiGENE) |
| Aromatase inhibitors | Aminoglutethimide | Exemestan |
| | Letrozole | Atamestan (BioMedicines) |
| | Anastrazole | YM-511 (Yamanouchi) |
| | Formestan | |
| Thymidylate synthase inhibitors | Pemetrexed (Eli Lilly) | Nolatrexed (Eximias) |
| | ZD-9331 (BTG) | CoFactor ™ (BioKeys) |
| DNA antagonists | Trabectedin (PharmaMar) | Mafosfamide (Baxter International) |
| | Glufosfamide (Baxter International) | Apaziquone (Spectrum Pharmaceuticals) |
| | Albumin + 32P (Isotope Solutions) | O6-benzylguanine (Paligent) |
| | Thymectacin (NewBiotics) | |
| | Edotreotid (Novartis) | |
| Farnesyl transferase inhibitors | Arglabin (NuOncology Labs) | Tipifarnib (Johnson & Johnson) |
| | Ionafarnib (Schering-Plough) | Perillyl alcohol (DOR BioPharma) |
| | BAY-43-9006 (Bayer) | |
| Pump inhibitors | CBT-1 (CBA Pharma) | Zosuquidar trihydrochloride (Eli Lilly) |
| | Tariquidar (Xenova) | |
| | MS-209 (Schering AG) | Biricodar dicitrate (Vertex) |
| Histone acetyl transferase inhibitors | Tacedinaline (Pfizer) | Pivaloyloxymethyl butyrate (Titan) |
| | SAHA (Aton Pharma) | |
| | MS-275 (Schering AG) | Depsipeptide (Fujisawa) |
| Metalloproteinase inhibitors | Neovastat (Aeterna Laboratories) | CMT-3 (CollaGenex) |
| | Marimastat (British Biotech) | BMS-275291 (Celltech) |
| Ribonucleoside reductase inhibitors | | Tezacitabine (Aventis) |
| | | Didox (Molecules for Health) |
| | Gallium maltolate (Titan) | |
| | Triapin (Vion) | |

TABLE 1-continued

| | | |
|---|---|---|
| TNF-alpha agonists/ antagonists | Virulizin (Lorus Therapeutics) CDC-394 (Celgene) | Revimid (Celgene) |
| Endothelin-A receptor antagonists | Atrasentan (Abbot) ZD-4054 (AstraZeneca) | YM-598 (Yamanouchi) |
| Retinoic acid receptor agonists | Fenretinide (Johnson & Johnson) LGD-1550 (Ligand) | Alitretinoin (Ligand) |
| Immuno- modulators | Interferon Oncophage (Antigenics) GMK (Progenics) Adenocarcinoma vaccine (Biomira) CTP-37 (AVI BioPharma) JRX-2 (Immuno-Rx) PEP-005 (Peplin Biotech) Synchrovax vaccines (CTL Immuno) Melanoma vaccine (CTL Immuno) p21-RAS vaccine (GemVax) | Dexosome therapy (Anosys) Pentrix (Australian Cancer Technology) JSF-154 (Tragen) Cancer vaccine (Intercell) Norelin (Biostar) BLP-25 (Biomira) MGV (Progenics) !3-Alethin (Dovetail) CLL-Thera (Vasogen) |
| Hormonal and antihormonal agents | Oestrogens Conjugated oestrogens Ethynyloestradiol chlorotrianisene Idenestrol Hydroxyprogesterone caproate Medroxyprogesterone Testosterone Testosterone propionate Fluoxymesterone Methyltestosterone Diethylstilbestrol Megestrol Tamoxifen Toremofin Dexamethasone | Prednisone Methylprednisolone Prednisolone Aminoglutethimide Leuprolide Goserelin Leuporelin Bicalutamide Flutamide Octreotide Nilutamide Mitotan P-04 (Novogen) 2-methoxyoestradiol (EntreMed) Arzoxifen (Eli Lilly) |
| Photodynamic agents | Talaporfin (Light Sciences) Theralux (Theratechnologies) Motexafin-Gadolinium (Pharmacyclics) | Pd-Bacteriopheophorbid (Yeda) Lutetium-Texaphyrin (Pharmacyclics) Hypericin |
| Tyrosine kinase inhibitors | Imatinib (Novartis) Leflunomide(Sugen/Pharmacia) ZDI839 (AstraZeneca) Erlotinib (Oncogene Science) Canertjnib (Pfizer) Squalamine (Genaera) SU5416 (Pharmacia) SU6668 (Pharmacia) ZD4190 (AstraZeneca) ZD6474 (AstraZeneca) Vatalanib (Novartis) PKI166 (Novartis) GW2016 (GlaxoSmithKline) EKB-509 (Wyeth) EKB-569 (Wyeth) | Kahalide F (PharmaMar) CEP-701 (Cephalon) CEP-751 (Cephalon) MLN518 (Millenium) PKC412 (Novartis) Phenoxodiol O Trastuzumab (Genentech) C225 (ImClone) rhu-Mab (Genentech) MDX-H210 (Medarex) 2C4 (Genentech) MDX-447 (Medarex) ABX-EGF (Abgenix) IMC-1C11 (ImClone) |
| Various agents | SR-27897 (CCK-A inhibitor, Sanofi- Synthelabo) Tocladesine (cyclic AMP agonist, Ribapharm) Alvocidib (CDK inhibitor, Aventis) CV-247 (COX-2 inhibitor, Ivy Medical) P54 (COX-2 inhibitor, Phytopharm) CapCell ™ (CYP450 stimulant, Bavarian Nordic) GCS-IOO (gal3 antagonist, GlycoGenesys) G17DT immunogen (gastrin inhibitor, Aphton) Efaproxiral (oxygenator, | BCX-1777 (PNP inhibitor, BioCryst) Ranpirnase (ribonuclease stimulant, Alfacell) Galarubicin (RNA synthesis inhibitor, Dong- A) Tirapazamine (reducing agent, SRI International) N-Acetylcysteine (reducing agent, Zambon) R-Flurbiprofen (NF-kappaB inhibitor, Encore) 3CPA (NF-kappaB inhibitor, Active Biotech) Seocalcitol (vitamin D receptor agonist, Leo) 131-I-TM-601 (DNA |

TABLE 1-continued

| | |
|---|---|
| Allos Therapeutics) | antagonist, |
| PI-88 (heparanase inhibitor, Progen) | TransMolecular) |
| Tesmilifen (histamine antagonist, YM BioSciences) | Eflornithin (ODC inhibitor, ILEX Oncology) |
| | Minodronic acid (osteoclast inhibitor, Yamanouchi) |
| Histamine (histamine H2 receptor agonist, Maxim) | Indisulam (p53 stimulant, Eisai) |
| Tiazofurin (IMPDH inhibitor, Ribapharm) | Aplidin (PPT inhibitor, PharmaMar) |
| Cilengitide (integrin antagonist, Merck KGaA) | Rituximab (CD20 antibody, Genentech) |
| SR-31747 (IL-1 antagonist, Sanofi-Synthelabo) | Gemtuzumab (CD33 antibody, Wyeth Ayerst) |
| CCI-779 (mTOR kinase inhibitor, Wyeth) | PG2 (haematopoiesis promoter, Pharmagenesis) |
| Exisulind (PDE-V inhibitor, Cell Pathways) | Immunol ™ (triclosan mouthwash, Endo) |
| CP-461 (PDE-V inhibitor, Cell Pathways) | Triacetyluridine (uridine prodrug, Wellstat) |
| AG-2037 (GART inhibitor, Pfizer) | SN-4071 (sarcoma agent, Signature BioScience) |
| WX-UK1 (plasminogen activator inhibitor, Wilex) | TransMID-107 ™ (immunotoxin, KS Biomedix) |
| PBI-1402 (PMN stimulant, ProMetic LifeSciences) | |
| Bortezomib (proteasome inhibitor, Millennium) | PCK-3145 (apoptosis promoter, Procyon) |
| SRL-172 (T-cell stimulant, SR Pharma) | Doranidazole (apoptosis promoter, Pola) |
| TLK-286 (glutathione-S transferase inhibitor, Telik) | CHS-828 (cytotoxic agent, Leo) |
| PT-100 (growth factor agonist, Point Therapeutics) | Trans-retinic acid (differentiator, NIH) |
| | MX6 (apoptosis promoter, |

A combined treatment of this type can be achieved with the aid of simultaneous, consecutive or separate dispensing of the individual components of the treatment. Combination products of this type employ the compounds according to the invention.

Assays

The compounds of the formula I described in the examples were tested by the assays described below and were found to have kinase inhibitory activity. Other assays are known from the literature and could readily be performed by the person skilled in the art (see, for example, Dhanabal et al., Cancer Res. 59:189-197; Kin et al., J. Biol. Chem. 274:9116-9121; Sheu et al., Anticancer Res. 18:4435-4441; Ausprunk et al., Dev. Biol. 38:237-248; Gimbrone et al., J. Natl. Cancer Inst. 52:413-427; Nicosia et al., In Vitro 18:538-549).

Measurement of Met Kinase Activity

According to the manufacturer's data (Met, active, upstate, catalogue No. 14-526), Met kinase is expressed for the purposes of protein production in insect cells (Sf21; S. frugiperda) and subsequent affinity-chromatographic purification as "N-terminal 6His-tagged" recombinant human protein in a baculovirus expression vector.

The kinase activity can be measured using various available measurement systems. In the scintillation proximity method (Sorg at al., J. of Biomolecular Screening, 2002, 7, 11-19), the flashplate method or the filter binding test, the radioactive phosphorylation of a protein or peptide as substrate is measured using radioactively labelled ATP ($^{32}$P-ATP, $^{33}$P-ATP). In the case of the presence of an inhibitory compound, a reduced radioactive signal, or none at all, can be detected. Furthermore, homogeneous time-resolved fluorescence resonance energy transfer (HTR-FRET) and fluorescence polarisation (FP) technologies can be used as assay methods (Sills et al., J. of Biomolecular Screening, 2002, 191-214).

Other non-radioactive ELISA assay methods use specific phospho-antibodies (phospho-ABs). The phospho-antibody only binds the phosphorylated substrate. This binding can be detected by chemiluminescence using a second peroxidase-conjugated antibody (Ross et al., 2002, Biochem. J.).

Flashplate Method (Met Kinase)

The test plates used are 96-well Flashplate® microtitre plates from Perkin Elmer (Cat. No. SMP200). The components of the kinase reaction described below are pipetted into the assay plate. The Met kinase and the substrate poly Ala-Glu-Lys-Tyr, (pAGLT, 6:2:5:1), are incubated for 3 hrs at room temperature with radioactively labelled $^{33}$P-ATP in the presence and absence of test substances in a total volume of 100 µl. The reaction is terminated using 150 µl of a 60 mM EDTA solution. After incubation for a further 30 min at room temperature, the supernatants are filtered off with suction, and the wells are washed three times with 200 µl of 0.9% NaCl solution each time. The measurement of the bound radioactivity is carried out by means of a scintillation measuring instrument (Topcount NXT, Perkin-Elmer).

The full value used is the inhibitor-free kinase reaction. This should be approximately in the range 6000-9000 cpm. The pharmacological zero value used is staurosporin in a final concentration of 0.1 mM. The inhibitory values (IC50) are determined using the RS1_MTS program.

Kinase reaction conditions per well:

30 µl of assay buffer

10 µl of substance to be tested in assay buffer with 10% of DMSO

10 µl of ATP (final concentration 1 µM cold, 0.35 µCi of $^{33}$P-ATP)

50 µl of Met kinase/substrate mixture in assay buffer;

(10 ng of enzyme/well, 50 ng of pAGLT/well)

Solutions used:
Assay buffer:
50 mM HEPES
3 mM magnesium chloride
3 µM sodium orthovanadate
3 mM manganese(II) chloride
1 mM dithiothreitol (DTT)
pH=7.5 (to be set using sodium hydroxide)
Stop solution:
60 mM Titriplex III (EDTA)
$^{33}$P-ATP: Perkin-Elmer;
Met kinase: Upstate, Cat. No. 14-526, Stock 1 µg/10 µl; spec. activity 954 U/mg;
Poly-Ala-Glu-Lys-Tyr, 6:2:5:1: Sigma Cat. No. P1152

Above and below, all temperatures are indicated in ° C. In the following examples, "conventional work-up" means: water is added if necessary, the pH is adjusted, if necessary, to values between 2 and 10, depending on the constitution of the end product, the mixture is extracted with ethyl acetate or dichloromethane, the phases are separated, the organic phase is dried over sodium sulfate and evaporated, and the residue is purified by chromatography on silica gel and/or by crystallisation, Rf values on silica gel; eluent:ethyl acetate/methanol 9:1, Mass spectrometry (MS):
  EI (electron impact ionisation) M$^+$
  FAB (fast atom bombardment) (M+H)$^+$
  ESI (electrospray ionisation) (M+H)$^+$
  APCI-MS (atmospheric pressure chemical ionisation-mass spectrometry) (M+H)$^+$.

HPLC Analyses (Method A)
Column: Chromolith RP18e 50*4.6 mm
Flow rate: 2 ml/min
Solvent A: 0.05M aqueous NaHPO$_4$
Solvent B: acetonitrile+10% of water
Gradient 8 min
0-1 min: 99:1->99:1
1-7 min: 99:1-1:99
7-8 min: 1:99->1:99

HPLC Analysis (Method B)
Flow rate: 2 ml/min
99:01-0:100 water+0.1% (vol.) of TFA:acetonitrile+0.1% (vol.) of TFA
0.0 to 0.2 min: 99:01
0.2 to 3.8 min: 99:01->0:100
3.8 to 4.2 min: 0:100
Column: Chromolith Performance RP18e; 100 mm long, internal diameter
3 mm, wavelength: 220 nm HPLC Analyses (Method C)
Flow rate: 4 ml/min
Solvent A: 0.1 M trifluoroacetic acid in water
Solvent B: 0.1 M trifluoroacetic acid in acetonitrile:water (9:1)
Gradient 8 min
0-1 min: 99:1->99:1
1-7 min: 99:1-1:99
7-8 min: 1:99->1:99

LC-MS Method:
Column: Chromolith RP18e 50*4.6 mm
Flow rate: 2.4 ml/min
Solvent A: 0.1 M trifluoroacetic acid in water
Solvent B: 0.1 M trifluoroacetic acid in acetonitrile
0.0 to 2.6 min: 96:04 (solvent A:solvent B)→100% of solvent B
2.6 to 3.3 min: 100% of solvent B

EXAMPLE 1

The preparation of 3-(4-methylpiperazin-1-yl)propyl[3-(5-methoxy-2-oxo-benzooxazol-3-ylmethyl)phenyl]carbamate ("A1") is carried out analogously to the following scheme:

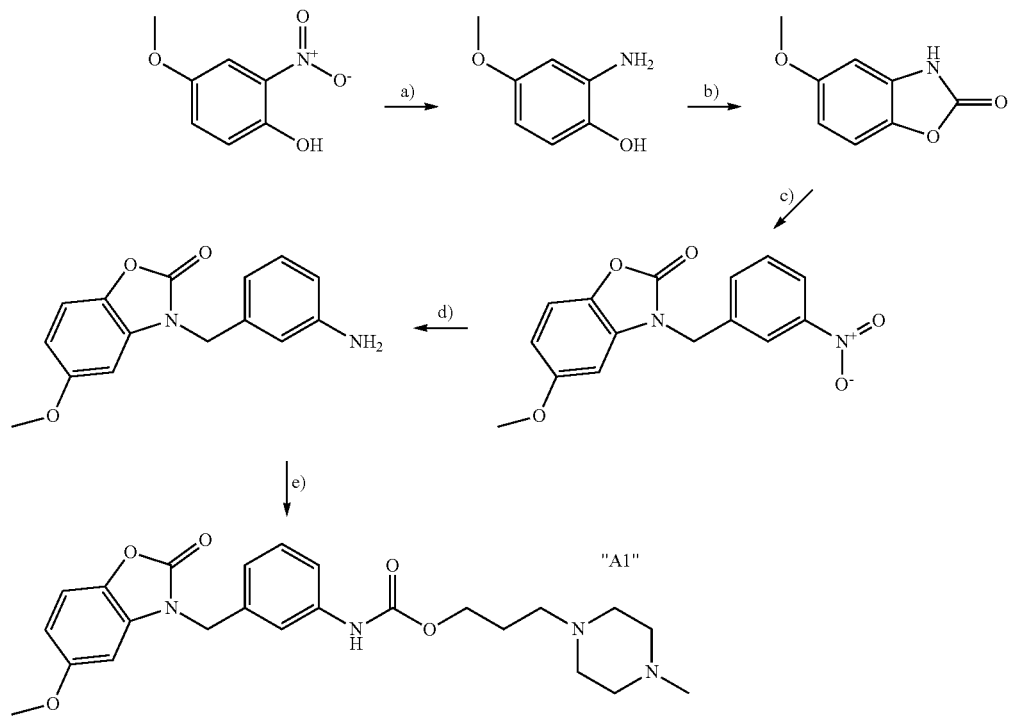

1.1 3.56 g of 4-methoxy-2-nitrophenol are dissolved in 35 ml of methanol, 1 g of 5% Pd/C is added under an inert-gas atmosphere, and the mixture is hydrogenated at atmospheric pressure by addition of hydrogen until starting material is no longer visible in the TLC.

The hydrogenation solution obtained after filtration is evaporated to dryness in a rotary evaporator. The residue is dissolved in acetone, filtered off through Celite with suction using activated carbon, and the mother liquor is evaporated to dryness. The residue is triturated with ether, filtered off with suction and dried at 50° C. in a vacuum drying oven;

m.p. 134-136°; ESI: 140 (M+H); HPLC Rt=2.19 min (method A);

yield: 1.78 g (64%) of 2-amino-4-methoxyphenol.

1.2 1.78 g of 2-amino-4-methoxyphenol are dissolved in 20 ml of THF in a 100 ml flask fitted with magnetic stirrer and drying tube, 2.12 g of 1,1'-carbonyldiimidazole are added with stirring, and the mixture is stirred at RT for a further 1 h. The dark-brown reaction solution is evaporated, and 50 ml of water are added, during which a precipitate occurs. This is separated off. It is washed well with water, the crystals are taken up in dichloromethane, the residual water is separated off, the solution is dried by addition of activated carbon, the mixture is filtered through Celite with suction, and the mother liquor is evaporated to dryness. The residue is triturated with ether, filtered off with suction and dried; m.p. 173-175°; ESI: 166 (M+H); HPLC: Rt 3.55 min (method A);

yield: 1.28 g (61%) of 5-methoxy-3H-benzooxazol-2-one.

1.3 1.28 g of 5-methoxy-2-benzoxazolinone are suspended in 20 ml of acetonitrile in a 100 ml round-bottomed flask fitted with magnetic stirrer, condenser and drying tube, 1.88 g of 3-nitrobenzyl bromide and 4.37 g of potassium carbonate are added, and the mixture is stirred at a bath temperature of 80° C. for 1 h. The mixture is poured into water, stirred well and filtered with suction. The crystals are dissolved in dichloromethane, the residual water is separated off, the mixture is dried and filtered, and the solvent is removed. The residue is stirred with ether, filtered off with suction again and dried;

m.p. 125-126°; ESI: 301 (M+H); HPLC: Rt=5.20 min (method A);

yield: 1.92 g (83%) of 5-methoxy-3-(3-nitrobenzyl)-3H-benzooxazol-2-one.

1.4 1.9 g of 5-methoxy-3-(3-nitrobenzyl)-3H-benzooxazol-2-one are dissolved in a mixture of 10 ml of THF and 10 ml of methanol, 1 g of Raney Ni is added under an inert-gas atmosphere, and the mixture is hydrogenated at atmospheric pressure by addition of hydrogen until starting material is no longer visible in the TLC. The solution freed from catalyst by filtration is dried over $Na_2SO_4$ and subsequently concentrated until a thick crystal slurry is present. This crystal slurry is diluted with about 200 ml of diethyl ether, and the crystals are filtered off with suction, washed with ether and dried at 50° C. in a vacuum drying cabinet;

m.p. 118°; ESI: 271 (M+H); HPLC: Rt=4.56 (method A);

yield: 1.19 g (69%) of 3-(3-aminobenzyl)-5-methoxy-2-benzoxazolinone.

1.5 324.34 mg of 3-(3-aminobenzyl)-5-methoxy-2-benzoxazolinone are suspended in 5 ml of dichloromethane in a reaction vial fitted with a magnetic stirrer, 252.03 μl of triethylamine are added, 145.35 mg of bis-(trichloromethyl) carbonate (triphosgene) are carefully added with cooling and stirring, and the mixture is stirred at RT for 10 minutes. 208.88 mg of 3-(4-methyl-1-piperazinyl)-1-propanol are then added, and the mixture is stirred at RT for 24 h in a tightly sealed reaction vial in a multiple synthesiser. The reaction mixture is diluted with dichloromethane, washed with water, dried and filtered, and the solvent is removed. The residue is adsorbed onto silica gel and chromatographed over a flash column on a FlashMaster with 20 g of LiChroprep 60 (25-40 μm) and dichloromethane+0-50% of methanol. The residue is dissolved in methanol, ethereal hydrochloric acid is added, the salt is precipitated using ether, and the supernatant solution is poured off. The salt is crystallised using methanol/ether, filtered off with suction, washed with ether and dried; m.p. 120°, decomposition from 150°; ESI: 455 (M+H); HPLC: Rt=4.00 (method A);

yield: 383 mg (61%) of "A1".

Preparation of 3-(4-methylpiperazin-1-yl)propyl[3-(5-methyl-2-oxo-oxazolo[4,5-b]pyridin-3-ylmethyl)phenyl]carbamate ("B1")

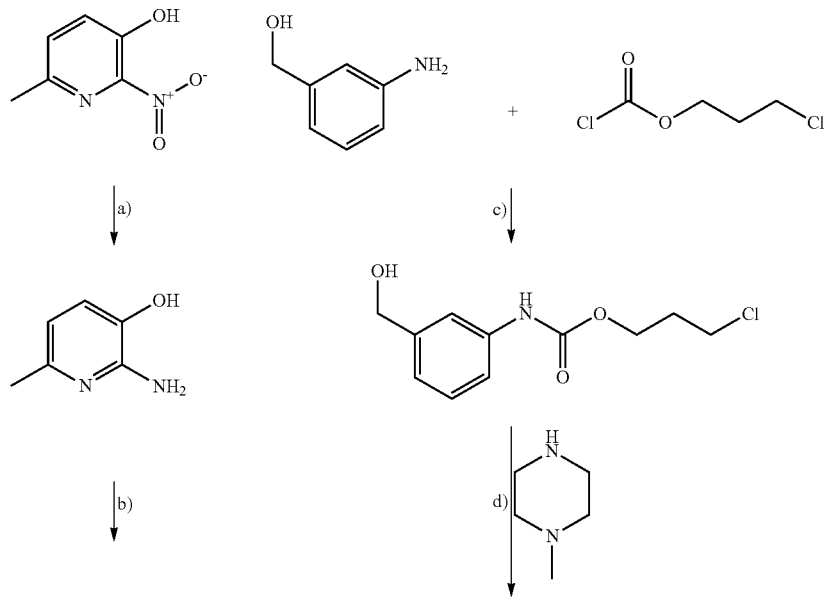

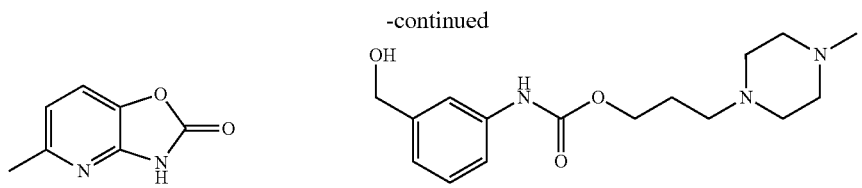

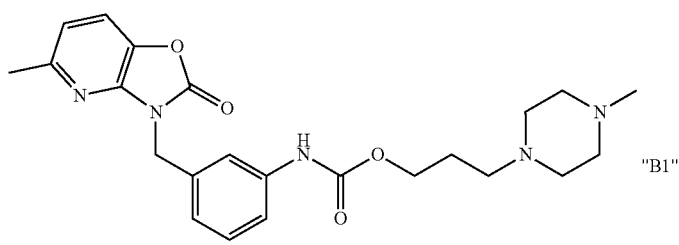

"B1"

Step a:

Preparation of 2-amino-6-methylpyridin-3-ol

Reduction of 6-methyl-2-nitropyridin-3-ol in a corresponding manner to Example 1.1 gives the desired product; ESI: 125 (M+H), Rt=0.51 min (method B).

Step b:

Preparation of 5-methyl-3H-oxazolo[4,5-b]pyridin-2-one

Reaction of 2-amino-6-methylpyridin-3-ol with CDI (carbonyldiimidazole) in a corresponding manner to Example 1.2 gives the desired product; ESI: 151 (M+H), Rt=1.58 min (method B).

Step c:

Preparation of 3-chloropropyl (3-hydroxymethylphenyl)carbamate 3.7 g (30 mmol) of 3-aminobenzyl alcohol are dissolved in 50 ml of acetone, and 3.2 g (30 mmol) of sodium carbonate are added. 5.7 g (36 mmol) of 3-chloropropyl chloroformate are metered into this suspension at 25° C. The reaction mixture is stirred at room temperature for a further 18 h. Water is added to the reaction mixture for hydrolysis, and the solid is subsequently filtered off. The solution is concentrated by distillation, during which the product deposits as an oil. The product phase is separated off. The aqueous phase is extracted with ethyl acetate. The organic phases are combined, washed with water and dried over sodium sulfate. The mixture is subsequently evaporated to dryness. The crude product is reacted further directly without further purification;
ESI: 244 (M+H).

Step d:

Synthesis of 3-(4-methylpiperazin-1-yl)propyl (3-hydroxymethylphenyl)carbamate 10 g (100 mmol) of N-methylpiperazine are added to a solution of 2.4 g (10 mmol) of 3-chloropropyl (3-hydroxymethylphenyl)carbamate in 10 ml of acetonitrile. The solution is refluxed for 4 h. The mixture is then hydrolysed by addition of water and cooled to about 65° C., and ethyl acetate is added. The mixture is then cooled to room temperature, during which the product is obtained as a solid between the organic and aqueous phases. The product is filtered off and rinsed with water, acetonitrile and ethyl acetate. The product is subsequently dried at 50° C. for several hours; ESI: 308 (M+H).

Step e:

Preparation of 3-(4-methylpiperazin-1-yl)propyl[3-(5-methyl-2-oxooxazolo-[4,5-b]pyridin-3-ylmethyl)phenyl]carbamate 98 mg (0.65 mmol) of 5-methyl-3H-oxazolo[4,5-b]pyridin-2-one, 200 mg (0.65 mmol) of 3-(4-methylpiperazin-1-yl)propyl (3-hydroxymethylphenyl)-carbamate and 325 mg (0.98 mmol) of polymer-bound triphenylphosphine (3 mmol/g) are suspended in 5 ml of DMF, and the mixture is shaken for 30 min. 229 mg (0.98 mmol) of di-tert-butyl azodicarboxylate are subsequently added. The reaction mixture is shaken at room temperature. The reaction mixture is filtered and rinsed with THF, and the filtrate is evaporated. The residue is purified by column chromatography on silica gel. Product: 68 mg of "B1"; ESI: 440 (M+H), Rt=2.11 min (method B);

$^1$H-NMR (DMSO-$d_6$, δ in ppm): 9.62 (1H, b); 7.64 (1H, d); 7.39-7.45 (2H, m); 7.26 (1H, t); 7.04 (1H, d); 7.00 (1H, d); 4.96 (2H, s), 4.11 (2H, t); 2.77 (3H, s); 2.48-2.52 (superimposed, 10H, m); 2.48 (3H, s); 1.59 (2H, m).

Preparation of 2-(4-methylpiperazin-1-yl)ethyl{3-[1-(5,6-difluoro-2-oxo-benzoxazol-3-yl)ethyl]phenyl}carbamate ("A27")

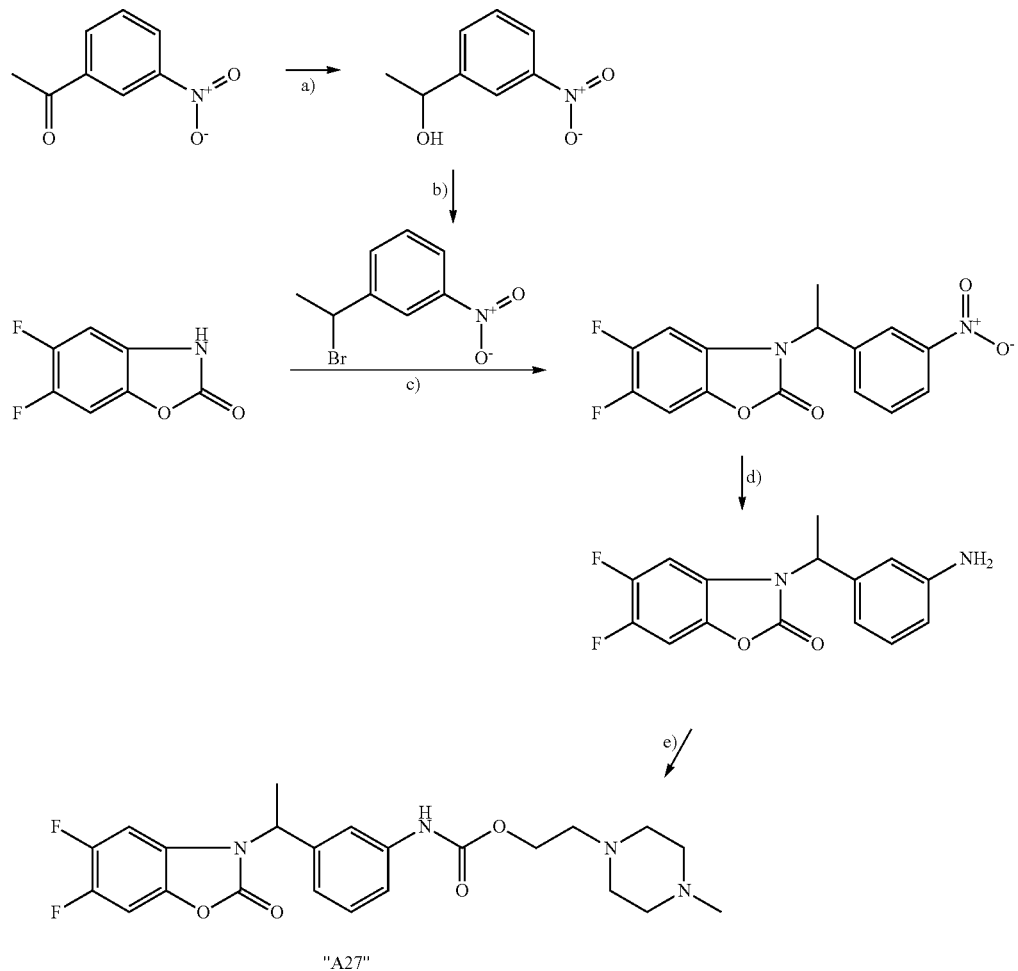

Step a:

Preparation of 1-(3-nitrophenyl)ethanol 26.4 g (160 mmol) of 1-(3-nitrophenyl)ethanone are suspended in 270 ml of methanol, and 6.1 g (160 mmol) of sodium borohydride are added in portions with ice cooling. The reaction mixture is subsequently stirred for a further 3 h without cooling, diluted with 300 ml of dichloromethane and washed with 3×200 ml of water. The organic phase is dried over sodium sulfate and evaporated to dryness.

Product: 26.15 g; HPLC: Rt=3.87 min (method A).

Step b:

Preparation of 1-(1-bromoethyl)-3-nitrobenzene 26.15 g (156 mmol) of 1-(3-nitrophenyl)ethanol are dissolved in 130 ml of glacial acetic acid, and 55 ml (313 mmol) of 33% HBr in glacial acetic acid are added dropwise with ice cooling. The reaction mixture is stirred at room temperature for 5 days. The mixture is subsequently diluted with 300 ml of DCM, washed with 3×200 ml of H$_2$O and 200 ml of saturated NaHCO$_3$ solution, dried over sodium sulfate and evaporated to dryness, and the residue is crystallised from petroleum ether.

Product: 30.4 g; HPLC: Rt=5.39 min (method A).

Step c:

Preparation of 5,6-difluoro-3-[1-(3-nitrophenyl)ethyl]-3H-benzoxazol-2-one 500 mg (2.9 mmol) of 5,6-difluoro-3H-benzoxazol-2-one, 672 mg (2.9 mmol) of (1-bromoethyl)-3-nitrobenzene and 1.58 g (11.4 mmol) of potassium carbonate are suspended in 6 ml of acetonitrile, and the mixture is stirred at 60° C. for 6 h. The mixture is subsequently diluted with 30 ml of MTBE, washed with 3×20 ml of H$_2$O, dried over sodium sulfate and evaporated to dryness. The crude product is purified by column chromatography on silica gel.

Product: 638 mg; ESI: 321 (M+H); HPLC: Rt=5.52 min (method A).

Step d:

Preparation of 3-[1-(3-aminophenyl)ethyl]-5,8-difluoro-3H-benzoxazol-2-one 633 mg (1.98 mmol) of 5,6-difluoro-3-[1-(3-nitrophenyl)ethyl]-3H-benzoxazol-2-one are dissolved in 10 ml of THF and hydrogenated under a hydrogen atmosphere using 700 mg of Raney nickel (water-wet). After 24 h, the reaction solution is filtered, the filtrate is evaporated to dryness, and the residue is crystallised from diethyl ether/petroleum ether.

Product: 500 mg; ESI: 291 (M+H), HPLC: Rt=5.01 min (method A).

Step e:

Preparation of 2-(4-methylpiperazin-1-yl)ethyl {3-[1-(5,6-difluoro-2-oxo-benzoxazol-3-yl)ethyl]phenyl}carbamate 250 mg (0.86 mmol) of 3-[1-(3-aminophenyl)ethyl]-5,6-difluoro-3H-benzoxazol-2-one, 137 mg (0.95 mmol) of 2-(4-methylpiperazin-1-yl)ethanol and 200 μl (1.81 mmol) of N-methylmorpholine are suspended in 10 ml of dichloromethane, the mixture is stirred at room temperature for 10 min, and 128 mg (0.43 mmol) of bis(trichloromethyl) carbonate are added. The reaction mixture is stirred at room temperature for 16 h. The mixture is subsequently diluted with 30 ml of dichloromethane, washed with 2×20 ml of saturated sodium hydrogencarbonate solution, dried over sodium sulfate and evaporated to dryness. The crude product is purified by column chromatography on silica gel, dissolved in acetone, warmed with HCl in ether and, when crystallisation is complete, filtered off with suction and dried. Product ("A27"): 95 mg, product is in the form of the hydrochloride;

m.p. 236-238° C. (decomposition); ESI: 461; HPLC: Rt=4.21 min (method A), $^1$H-NMR (DMSO-$d_6$, δ in ppm): 9.801 (SB, 1H), 7.728 (DD, 1H), 7.475 (M, 2H), 7.324 (M, 2H), 7.128 (D, 1H), 5.543 (M, 1H), 4.408 (SB, 2H), 4.023-3.110 (M, 10H), 2.809 (SB, 3H), 1.843 (D, 3H).

The following compounds are obtained analogously:

| No. | Name and/or structure | LCMS retention time [min]/LCMS mass [M + H]$^+$/m.p. [° C.] |
|---|---|---|
| "A6" | 3-(4-Methylpiperazin-1-yl)propyl [3-(6-chloro-2-oxobenzoxazol-3-ylmethyl)phenyl]carbamate | 1.673/459.8/243 (decomposition) |
| "A7" | 3-(4-Methylpiperazin-1-yl)propyl [3-(5-methyl-2-oxobenzoxazol-3-ylmethyl)phenyl]carbamate | 1.629/438.8/228 (decomposition) |
| "A8" | 3-(4-Methylpiperazin-1-yl)propyl [3-(5-acetyl-2-oxo-benzoxazol-3-ylmethyl)phenyl]carbamate | 1.514/466.8/174 (decomposition) |
| "A11" | 3-Dimethylaminopropyl [3-(2-oxooxazolo[4,5-b]pyridin-3-ylmethyl)phenyl]carbamate hydrochloride | ESI: 371 (M + H), HPLC: Rt = 3.53 min (method A) |
| "A16" | 3-Dimethylaminopropyl [3-(2-oxobenzoxazol-3-yl-methyl)phenyl]carbamate | 138-140 ESI: 370 (M + H), HPLC: Rt = 3.89 min (method A) |
| "A17" | 2-(4-Methylpiperazin-1-yl)ethyl [3-(2-oxobenzoxa-zol-3-ylmethyl)phenyl]carbamate hydrochloride | 1.509/410.8/237 (decomposition) ESI: 411 (M + H), HPLC: Rt = 3.87 min (method A) |

$^1$H NMR (250 MHz, DMSO-$d_6$) δ [ppm] 9.757 (s, 1H), 7.452 (sb, 1H), 7.419 (d, 1H), 7.370 (d, 1H), 7.286 (t, 1H), 7.185-7.129 (m, 3H), 7.053 (d, 1H), 5.011 (s, 2H), 4.343 (t, 2H), 3.803-3.403 (m, 10H), 2.794 (s, 3H)

| | | |
|---|---|---|
| "A18" | 3-(4-Methylpiperazin-1-yl)propyl [3-(2-oxobenz-oxazol-3-ylmethyl)phenyl]carbamate | 1.524/424.8/205 (decomposition) ESI: 425 (M + H), HPLC: Rt = 3.92 min (method A) |

$^1$H NMR (250 MHz, DMSO-$d_6$) δ [ppm] 9.676 (s, 1H), 7.453 (sb, 1H), 7.402 (d, 1H), 7.370 (d, 1H), 7.272 (t, 1H), 7.167-7.130 (m, 3H), 7.035 (d, 1H), 5.004 (s, 2H), 4.122 (t, 2H), 3.456 (m, 10H), 2.795 (s, 3H), 2.006 (t, 2H)

| | | |
|---|---|---|
| "A19" | 3-(4-Methylpiperazin-1-yl)propyl [3-(5,6-difluoro-2-oxobenzoxazol-3-ylmethyl)phenyl]carbamate | 1.609/460.8/264-265 (decomposition) ESI: 461 (M + H), HPLC: Rt = 4.13 min (method A) |

-continued

| No. | Name and/or structure | LCMS retention time [min]/LCMS mass [M + H]+/ m.p. [° C.] |
|---|---|---|
| "A20" | 3-(4-Methylpiperazin-1-yl)propyl [3-(6-methoxy-2-oxobenzoxazol-3-ylmethyl)phenyl]carbamate | 1.561/454.8/201 (decomposition) ESI: 455 (M + H), HPLC: Rt = 4.00 min (method A) |
| "A21" | 3-(4-Methylpiperazin-1-yl)propyl [3-(6-methyl-2-oxobenzoxazol-3-ylmethyl)phenyl]carbamate | 1.631/438.8/196 (decomposition) ESI: 439 (M + H), HPLC: Rt = 4.16 min (method A) |
| "A22" | 3-(4-Methylpiperazin-1-yl)propyl [3-(6-acetyl-2-oxo-benzoxazol-3-ylmethyl)phenyl]carbamate | 1.497/466.8/234 (decomposition) ESI: 467 (M + H), HPLC: Rt = 3.84 min (method A) |
| "A23" | Ethyl {3-[5-(4-methylpiperazin-1-yl)-2-oxobenzoxa-zol-3-ylmethyl]phenyl}carbamate<br>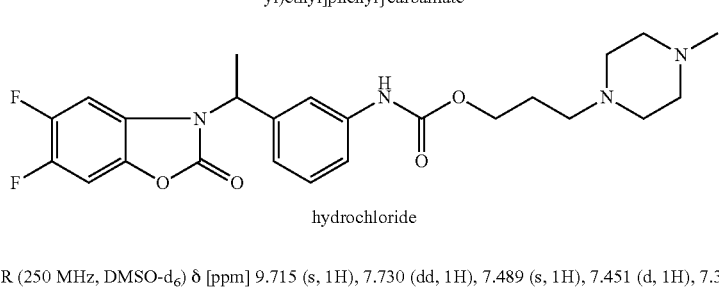<br>hydrochloride | 1.598/411.2/ 166-170 (decomposition) ESI: 411 (M + H), HPLC: Rt = 3.81 min (method A) |
| "A24" | 3-(4-Methylpiperazin-1-yl)propyl [3-(5-cyano-2-oxo-benzoxazol-3-ylmethyl)phenyl]carbamate, hydro-chloride | 1.514/450.2/ 212-214 ESI: 450 (M + H), HPLC: Rt = 3.89 min (method A) |
| "A25" | 3-(4-Methylpiperazin-1-yl)propyl [3-(5-ethyl-sulfonyl-2-oxobenzoxazol-3-ylmethyl)phenyl]-carbamate, dihydrochloride | 1.482/517.2/244 (decomposition) ESI: 517 (M + H), HPLC: Rt = 3.79 min (method A) |
| "A26" | 3-(4-Methylpiperazin-1-yl)propyl {3-[1-(5,6-difluoro-2-oxobenzoxazol-3-yl)ethyl]phenyl}carbamate<br>hydrochloride<br>$^1$H NMR (250 MHz, DMSO-d$_6$) δ [ppm] 9.715 (s, 1H), 7.730 (dd, 1H), 7.489 (s, 1H), 7.451 (d, 1H), 7.340-7.286 (m, 2H), 7.106 (d, 1H), 5.532 (q, 1H), 4.140 (t, 2H), 3.71-3.05 (m, 10H), 2.816 (s, 3H), 2.086 (sb, 2H), 1.839 (d, 3H) | 1.659/475.2/ 200-201 ESI: 475 (M + H), HPLC: Rt = 4.24 min (method A) |
| "A28a" | 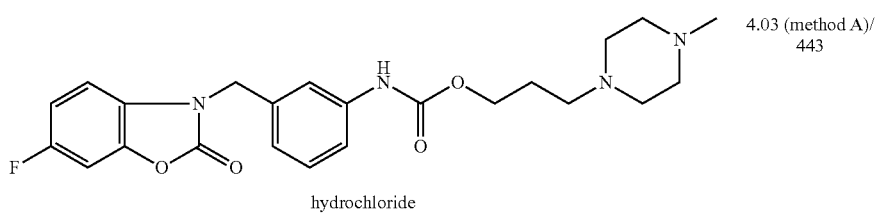<br>hydrochloride | 4.03 (method A)/ 443 |

| No. | Name and/or structure | LCMS retention time [min]/LCMS mass [M + H]+/ m.p. [° C.] |
|---|---|---|
| "A28b" | 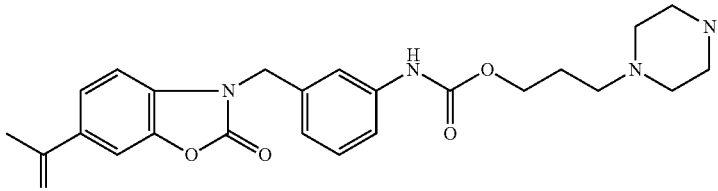 hydrochloride | 3.84 (method A)/ 467 |
EXAMPLE 2
The preparation of ethyl {3-[6-(2-dimethylaminoethylcarbamoyl)-2-oxo-benzoxazol-3-ylmethyl]phenyl}carbamate ("A29") is carried out analogously to the following scheme:
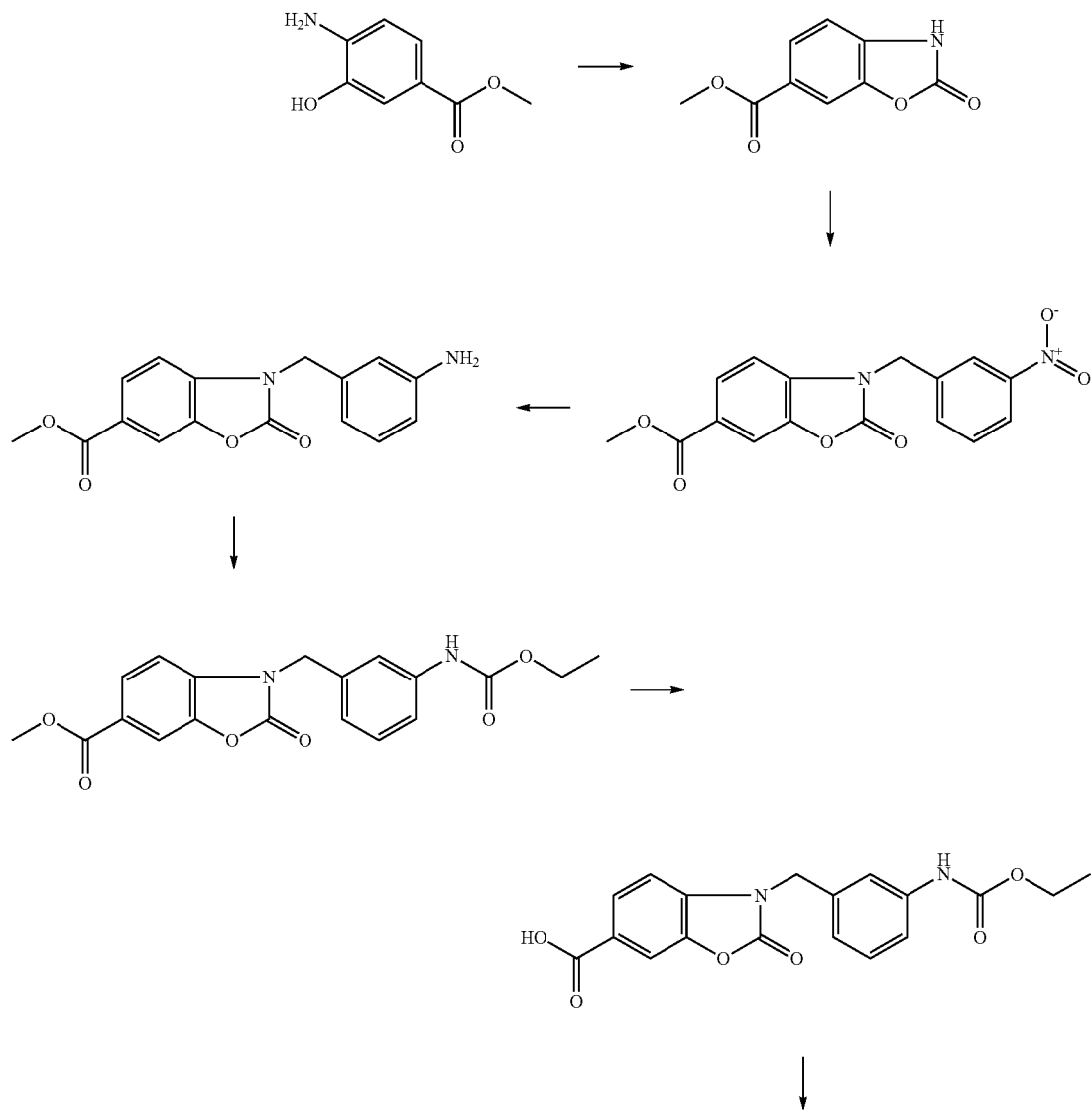

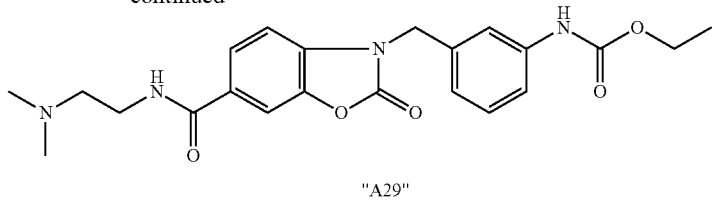

"A29"

2.1 9.36 g (0.056 mol) of methyl 3-hydroxy-4-aminobenzoate and 9.85 g of 1,1'-carbonyldiimidazole are dissolved in 125 ml of THF in a 250 ml single-necked flask with reflux condenser and drying tube, and the mixture is refluxed for 3 h. For work-up, the solvent is removed in a rotary evaporator, and the residue is taken up in dichloromethane and washed 3× with 1 N HCl and 1× with water. The organic phase is dried over sodium sulfate and evaporated to dryness in a rotary evaporator; yield 9.92 g (92%) of methyl 2-oxo-2,3-dihydrobenzoxazole-6-carboxylate; ESI: 194 (M+H); HPLC: Rt=2.57 min (method B).

2.2 1 g (5.2 mmol) of the substance methyl 2-oxo-2,3-dihydrobenzoxazole-6-carboxylate is dissolved in 20 ml of acetonitrile, 2.8 g (20.3 mmol) of potassium carbonate and 1.24 g (5.7 mmol) of m-nitrobenzyl bromide are added, and the mixture is heated under reflux for 16 h. After cooling, 30 ml of dichloromethane are added to te reaction mixture, and the mixture is extracted with 2×20 ml of water, the organic phase is dried over sodium sulfate, and the solvent is removed by distillation. The residue is slurried in methanol, filtered off with suction and washed with diethyl ether. The substance is reacted further without further purification; yield: 1.15 g (67%) of methyl 3-(3-nitrobenzyl)-2-oxo-2,3-dihydrobenzoxazole-6-carboxylate; m.p. 149-151° C.; ESI: 329 (M+H); HPLC: Rt=5.12 min (method A).

2.3 594 mg (1.8 mmol) of methyl 3-(3-nitrobenzyl)-2-oxo-2,3-dihydrobenzoxazole-6-carboxylate are dissolved in 10 ml of methanol, and the mixture is stirred under a hydrogen atmosphere with 0.6 g of Raney nickel. After a few hours, the formation of a precipitate is observed, and therefore 10 ml of THF are added, and the mixture is hydrogenated further under a hydrogen atmosphere. After 16 h, the reaction is terminated, and the catalyst is filtered off with suction and rinsed with methanol/THF. The residue is evaporated; yield: 562 mg of methyl 3-(3-aminobenzyl)-2-oxo-2,3-dihydrobenzoxazole-6-carboxylate. The substance is reacted further without further purification; ESI: 299 (M+H); HPLC: Rt=2.07 min (method B).

2.4 562 mg (1.88 mmol) of methyl 3-(3-aminobenzyl)-2-oxo-2,3-dihydrobenzoxazole-6-carboxylate are dissolved in 20 ml of dichloromethane in a round-bottomed flask, 152 µl (1.88 mmol) of pyridine are added, and 183 µl (1.88 mmol) of ethyl chloroformate are added dropwise with cold-water cooling. The mixture is stirred at RT for a further 1 hour, during which fine crystals deposit. A further 40 ml of DCM are added to the reaction mixture, which is then washed with 20 ml of 1 N HCl. The organic phase is washed with 20 ml of water until neutral and dried over sodium sulfate, and the solvent is removed by distillation; yield: 539 mg (77%) of methyl 3-(3-ethoxycarbonylaminobenzyl)-2-oxo-2,3-dihydrobenzoxazole-6-carboxylate. The substance is reacted further without further purification; ESI: 371 (M+H); HPLC: Rt=2.89 min (method B).

2.5 10 ml of water and 10 ml of conc. HCl are added to 517 mg (1.4 mmol) of methyl 3-(3-ethoxycarbonylaminobenzyl)-2-oxo-2,3-dihydrobenzoxazole-6-carboxylate in a 50 ml round-bottomed flask. The suspension is refluxed for 4 hours. A further 10 ml of conc. HCl are added, and the mixture is refluxed for 16 h. 10 ml of conc. HCl are added a further twice, and the mixture is refluxed for a further 16 h in each case.

The mixture is cooled to room temperature, and the precipitate is filtered off with suction and washed well with water; yield: 417 mg (84%) of 3-(3-ethoxycarbonylaminobenzyl)-2-oxo-2,3-dihydrobenzoxazole-6-carboxylic acid. The substance is reacted further without further purification; ESI: 357 (M+H); HPLC: Rt=2.54 min (method B).

2.6 100 mg (0.28 mmol) of 3-(3-ethoxycarbonylaminobenzyl)-2-oxo-2,3-dihydrobenzoxazole-6-carboxylic acid are dissolved in 2 ml of DMF, and 109 mg (0.56 mmol) of EDCI, 39 mg (0.56 mmol) of HOBt and 63 µl (0.56 mmol) of N-methylmorpholine are added. 37 µl (0.34 mmol) of 2-dimethylaminoethylamine are subsequently added, and the reaction solution is stirred at room temperature for 3 days.

The reaction mixture is purified by preparative HPLC, and the clean fractions are freeze-dried.

Yield: 89 mg (59%) of "A29" TFA salt; HPLC: RT=2.175 min (method B); LC-MS: [M+H]⁺=427 at RT=1.431 min.

The preparation of N-(2-dimethylaminoethyl)-2-oxo-3-(2-oxo-2,3-dihydro-1H-benzoimidazol-5-ylmethyl)-2,3-dihydrobenzoxazole-5-carboxamide ("A35") is carried out analogously to the following scheme:

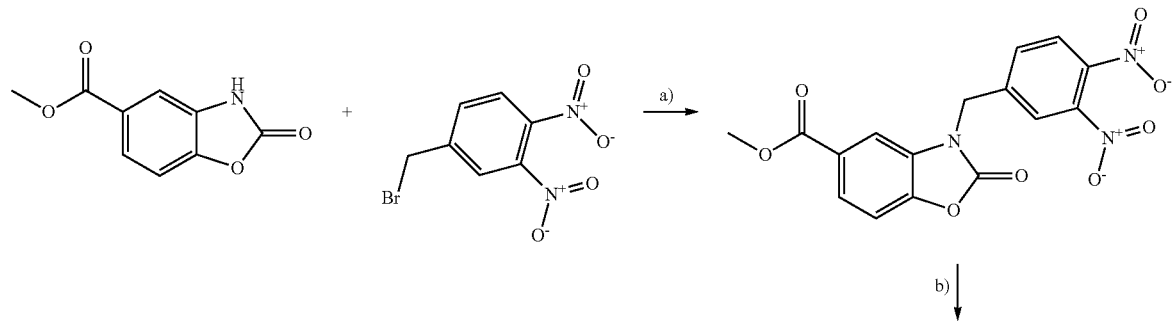

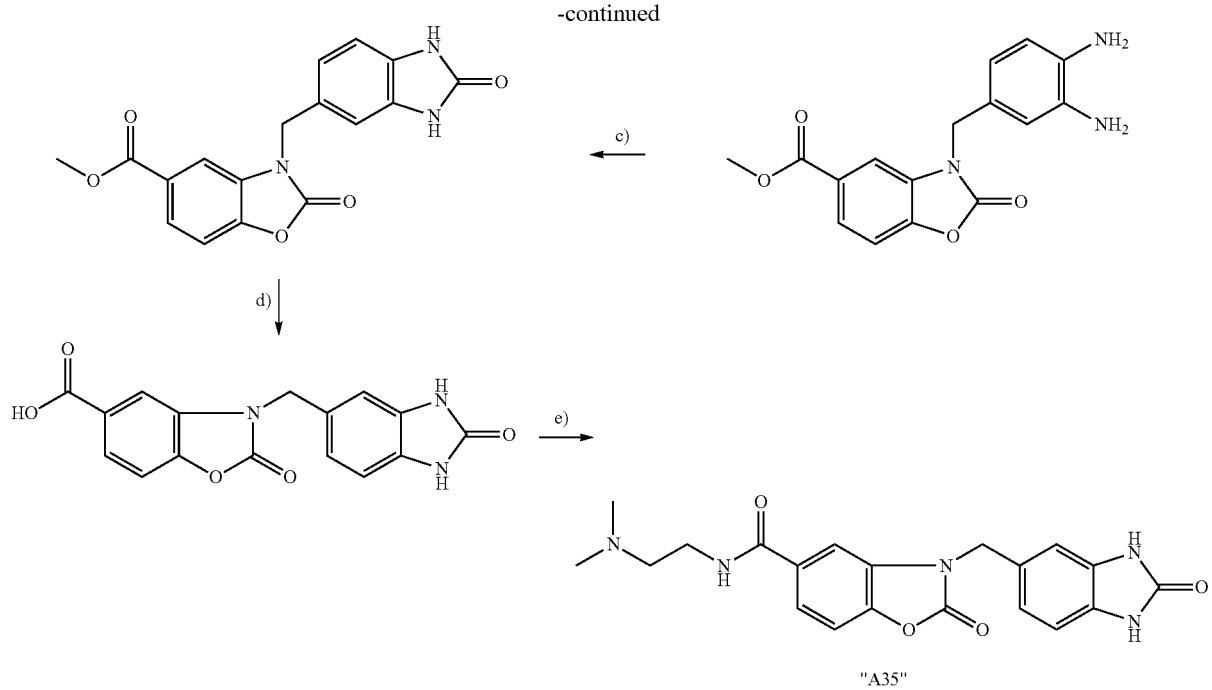

Step a)

Preparation of methyl 3-(3,4-dinitrobenzyl)-2-oxo-2,3-dihydrobenzoxazole-5-carboxylate 2 g (10.4 mmol) of methyl 2-oxo-2,3-dihydrobenzoxazole-5-carboxylate, 2.97 g (11.4 mmol) of 4-bromomethyl-1,2-dinitrobenzene (prepared in a corresponding manner to DE 3904797) and 5.7 g (41.4 mmol) of potassium carbonate are suspended in 50 ml of acetonitrile, and the mixture is stirred at 80° C. for 1 h. The reaction mixture is poured into 50 ml of water, extracted with 500 ml of MTBE, dried and evaporated to dryness. The residue is purified by column chromatography on silica gel; product: 1.5 g; ESI: 374 (M+H).

Step b:

Preparation of methyl 3-(3,4-diaminobenzyl)-2-oxo-2,3-dihydrobenzoxazole-5-carboxylate 1.45 g (3.8 mmol) of methyl 3-(3,4-dinitrobenzyl)-2-oxo-2,3-dihydrobenzoxazole-5-carboxylate are dissolved in 20 ml of THF and hydrogenated under a hydrogen atmosphere using 1 g of Raney nickel (water-wet). After 24 h, the reaction solution is filtered, and the filtrate is evaporated to dryness; product; 1.1 g, ESI: 314 (M+H).

Step c:

Preparation of methyl 2-oxo-3-(2-oxo-2,3-dihydro-1H-benzimidazol-5-yl-methyl)-2,3-dihydrobenzoxazole-5-carboxylate 1.1 g (3.5 mmol) of methyl 3-(3,4-diaminobenzyl)-2-oxo-2,3-dihydrobenzoxazole-5-carboxylate and 626 mg (3.9 mmol) of 1,1'-carbonyldiimidazole are stirred at room temperature for 24 h in 10 ml of THF. The reaction mixture is added to 150 ml of water, and the resultant precipitate is filtered off with suction and dried in vacuo; product; 1.1 g; ESI: 340 (M+H).

Step d:

Preparation of 2-oxo-3-(2-oxo-2,3-dihydro-1H-benzimidazol-5-ylmethyl)-2,3-dihydrobenzoxazole-5-carboxylic acid 1.1 g (3.24 mmol) of methyl 2-oxo-3-(2-oxo-2,3-dihydro-1H-benzimidazol-5-ylmethyl)-2,3-dihydrobenzoxazole-5-carboxylate are suspended in 20 ml of water, 30 ml of conc. hydrochloric acid are added, and the mixture is stirred at a bath temperature of 100° C. for 24 h. A further 20 ml of conc. HCl are added, and the reaction mixture is stirred at a bath temperature of 130° C. for 3 days. The suspension is filtered and washed with water, and the residue is dried at 50° C. in a drying cabinet; product; 996 mg; m.p. 230-231° C.; ESI 326; HPLC: Rt=4.24 min (method A).

Step e:

Preparation of N-(2-dimethylaminoethyl)-2-oxo-3-(2-oxo-2,3-dihydro-1H-benzimidazol-5-ylmethyl)-2,3-dihydrobenzoxazole-5-carboxamide 330 mg (0.76 mmol) of 2-oxo-3-(2-oxo-2,3-dihydro-1H-benzimidazol-5-yl-methyl)-2,3-dihydrobenzoxazole-5-carboxylic acid are dissolved in 3 ml of DMF, and 294 mg (1.52 mmol) of EDCI, 106 mg (0.76 mmol) of HOBt and 157 µl (1.52 mmol) of N-methylmorpholine are added. 81 mg (0.91 mmol) of 2-dimethylaminoethylamine are subsequently added, and the reaction solution is stirred at room temperature for 3 days. The reaction mixture is subsequently added to water and extracted with dichloromethane. The organic phase is dried over sodium sulfate, evaporated to dryness and purified by column chromatography on silica gel. The product is purified again by preparative HPLC; 100 mg of "A35" trifluoromethylacetate; ESI 397 (M+H), HPLC: Rt=3.89 min (method A).

The following compounds are obtained analogously:

| No. | Name and/or structure | LCMS retention time [min]/ LCMS mass [M + H]+/m.p. [° C.] |
|---|---|---|
| "A3" | 3-(4-Methylpiperazin-1-yl)propyl [3-(5-dimethyl-carbamoyl-2-oxobenzoxazol-3-ylmethyl)phenyl]-carbamate<br><br>trifluoroacetate | 1.435/496.2<br>HPLC: Rt = 3.60 min (method A) |
| "A4" | 3-Piperazin-1-ylpropyl [3-(5-dimethylcarbamoyl-2-oxobenzoxazol-3-ylmethyl)phenyl]carbamate | 1.432/482.2<br>HPLC: Rt = 3.57 min (method A) |
| "A5" | 3-(4-Methylpiperazin-1-yl)propyl [3-(5-propyl-carbamoyl-2-oxobenzoxazol-3-ylmethyl)phenyl]-carbamate | 1.520/510.2<br>HPLC: Rt = 3.97 min (method A) |
| "A10" | 3-Piperazin-1-ylpropyl [3-(5-propylcarbamoyl-2-oxobenzoxazol-3-ylmethyl)phenyl]carbamate | 245-253 (de-composition)<br>ESI: 496 (M + H),<br>HPLC: Rt = 4.03 min (method A) |
| "A12" | 3-Dimethylaminopropyl [3-(5-dimethylcarbamoyl-2-oxobenzoxazol-3-ylmethyl)phenyl]carbamate | 86-93<br>ESI: 441 (M + H),<br>HPLC: Rt = 3.65 min (method A) |
| "A13" | 3-Dimethylaminopropyl [3-(5-propylcarbamoyl-2-oxobenzoxazol-3-ylmethyl)phenyl]carbamate | 85-91<br>ESI: 455 (M + H),<br>HPLC: Rt = 3.92 min (method A) |
| \multicolumn{3}{l}{1H NMR (250 MHz, DMSO-$d_6$) δ [ppm] 9.624 (s, 1H), 8.415 (t, 1H), 7.679 (dd, 1H), 7.627 (s, 1H), 7.464-7.447 (m, 2H), 7.404 (d, 1H), 7.270 (t, 1H), 6.998 (d, 1H), 5.035 (s, 2H), 4.066 (t, 2H), 3.199 (m, 2H), 2.275 (t, 2H), 2.118 (s, 6H), 1.719 (m, 2H), 1.516 (m, 2H), 0.873 (t, 3H)} | | |
| "A14" | 3-Dimethylaminopropyl [3-(6-methoxycarbonyl-2-oxobenzoxazol-3-ylmethyl)phenyl]carbamate | 149-151<br>ESI: 428 (M + H),<br>HPLC: Rt = 4.03 min (method A) |
| "A15" | 3-Dimethylaminopropyl [3-(5-methoxycarbonyl-2-oxobenzoxazol-3-ylmethyl)phenyl]carbamate | ESI: 428 (M + H),<br>HPLC: Rt = 3.97 min (method A) |
| "A30" | Ethyl {3-[5-(2-dimethylaminoethylcarbamoyl)-2-oxobenzoxazol-3-ylmethyl]phenyl}carbamate | 1.586/427.2/<br>160-161<br>ESI: 427 (M + H),<br>HPLC: Rt = 3.73 min (method A) |
| "A31" | Ethyl {3-[5-(3-dimethylaminopropylcarbamoyl)-2-oxobenzoxazol-3-ylmethyl]phenyl}carbamate | 1.602/441.2/<br>116-119<br>ESI: 441 (M + H),<br>HPLC: Rt = 3.76 min (method A) |
| "A32" | Ethyl (3-{1-[5-(4-dimethylaminobutylcarbamoyl)-2-oxobenzoxazol-3-yl]ethyl}phenyl)carbamate | 1.661/469.2<br>ESI: 469 (M + H),<br>HPLC: Rt = 3.92 min (method A) |
| "A33" | Ethyl (3-{1-[5-(2-dimethylaminoethylcarbamoyl)-2-oxobenzoxazol-3-yl]ethyl}phenyl)carbamate | 1.644/441.2<br>ESI: 441 (M + H),<br>HPLC: Rt = 3.81 min (method A) |

| No. | Name and/or structure | LCMS retention time [min]/ LCMS mass [M + H]+/m.p. [° C.] |
|---|---|---|
| "A34" | N-(4-Dimethylaminobutyl)-2-oxo-3-(2-oxo-2,3-dihydro-1H-benzimidazol-5-ylmethyl)-2,3-dihydro-benzoxazole-5-carboxamide trifluoroacetate | 1.314/424.2 ESI: 424 (M + H), HPLC-MS: Rt = 1.31 min |
| "A36" | Ethyl (3-{1-[5-(3-dimethylaminopropylcarbamoyl)-2-oxobenzoxazol-3-yl]ethyl}phenyl)carbamate | 1.655/455.2/ 112-119/ESI: 455 (M + H), HPLC: Rt = 3.89 min (method A) |
| "A37" | Methyl 3-(3-ethoxycarbonylaminobenzyl)-2-oxo-2,3-dihydrobenzoxazole-6-carboxylate | ESI: 371 (M + H), HPLC: Rt = 2.89 min (method B) |
| "A38" | Ethyl {3-[6-(3-methylaminopropylcarbamoyl)-2-oxobenzoxazol-3-ylmethyl]phenyl}carbamate, trifluoroacetate (obtainable from "A40" using TFA in DCM) | 2.168/427 (at RT = 1.475) ESI: 427 (M + H), HPLC: Rt = 2.17 min (method B) |
| "A39" | Ethyl {3-[6-(3-dimethylaminopropylcarbamoyl)-2-oxobenzoxazol-3-ylmethyl]phenyl}carbamate, trifluoroacetate | 2.186/441 (at RT = 1.463 min) ESI: 441 (M + H), HPLC: Rt = 2.19 min (method B) |
| "A40" | Ethyl (3-{6-[3-(tert-butoxycarbonylmethylamino)-propylcarbamoyl]-2-oxobenzoxazol-3-ylmethyl}-phenyl)carbamate | 2.984/527 (at RT = 2.235 min) ESI: 527 (M + H), HPLC: Rt = 2.98 min (method B) |
| "A53" | | |

EXAMPLE 3

The preparation of ethyl (3-{6-[2-(4-methylpiperazin-1-yl)acetyl]-2-oxo-benzoxazol-3-ylmethyl}phenyl)carbamate ("A41") is carried out analogously to the following scheme:

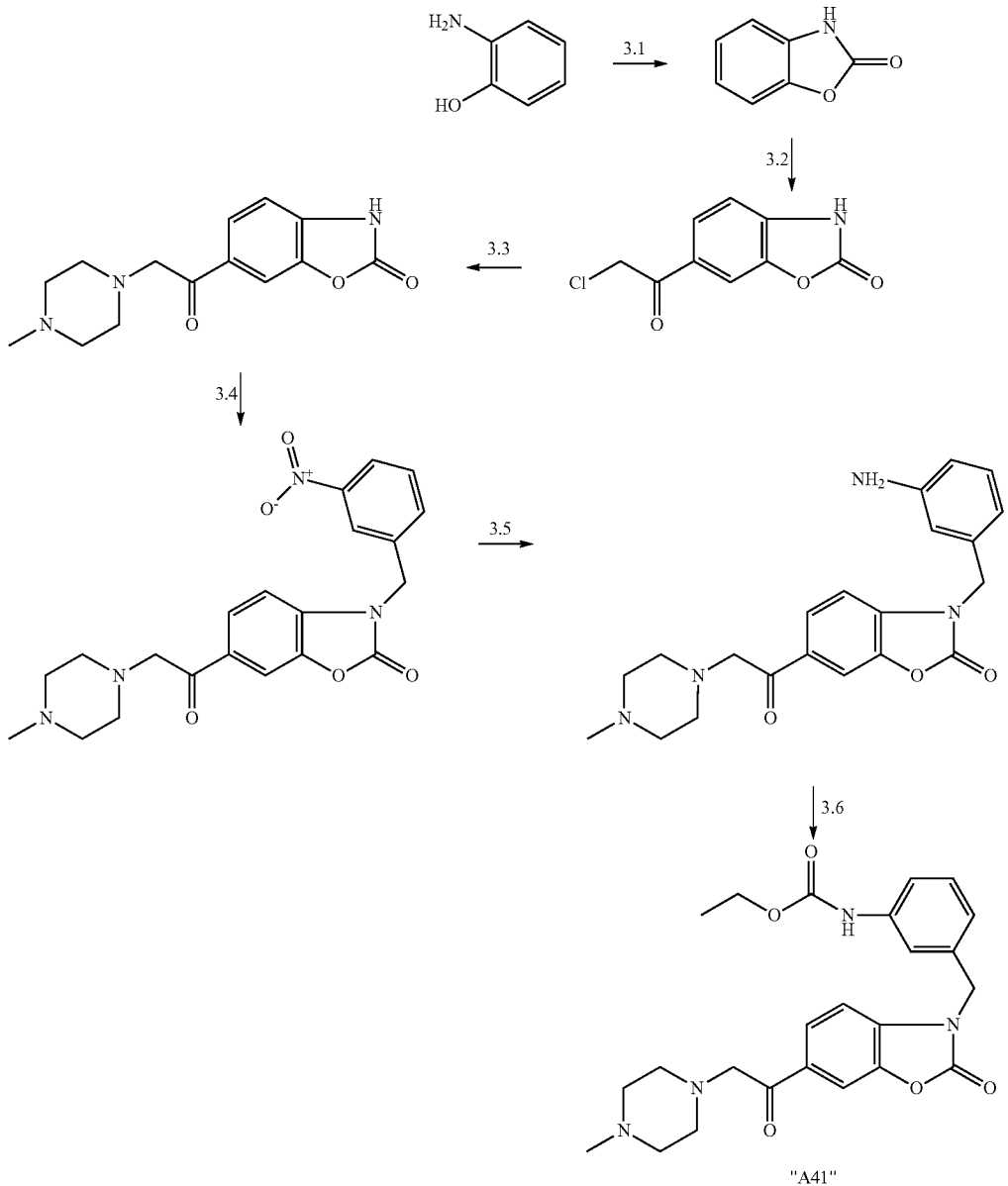

"A41"

3.3 1.6 ml (14.2 mmol) of 1-methylpiperazine are initially introduced in 50 ml of ethanol, 4.3 ml (31.2 mmol) of triethylamine are added, and 3 g (14.2 mmol) of 6-chloroacetyl-2-benzoxazolinone are added with stirring at room temperature. The reaction mixture is stirred overnight at room temperature. A further 1 ml (8.9 mmol) of 1-methylpiperazine is added, and the mixture is stirred at RT for 15 h and subsequently at 70° C. for 24 h. After cooling, the deposited crystals are filtered off with suction, washed with methanol and dried; yield: 0.8 g of 6-[2-(4-methylpiperazin-1-yl)acetyl]-3H-benzoxazol-2-one; HPLC: Rt=1.263 min. (method B); LC-MS: M+H=276 g/mol.

EXAMPLE 4

The preparation of 3-[3-(5-methyl-1,2,4-oxadiazol-3-yl)benzyl]-6-[2-(4-methylpiperazin-1-yl)acetyl]-3H-benzoxazol-2-one ("A42") is carried out analogously to the following scheme:

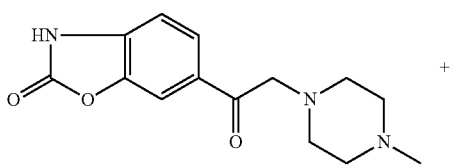

-continued

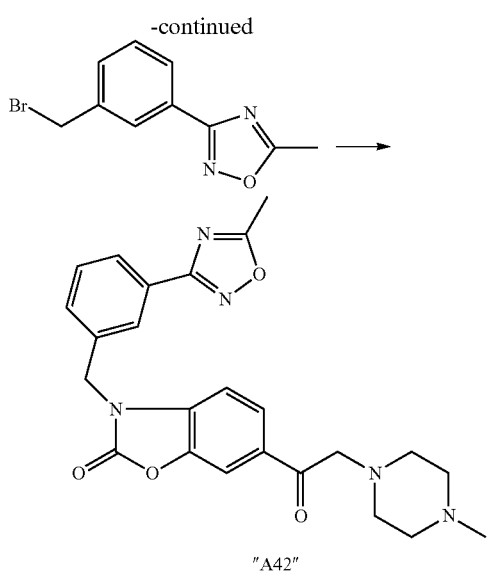

"A42"

309 mg (0.72 mmol) of 6-[2-(4-methylpiperazin-1-yl)acetyl]-3H-benzoxazol-2-one and 387 mg (2.8 mmol) of potassium carbonate are suspended in 10 ml of acetonitrile, and 200 mg (0.79 mmol) of 3-[3-(bromomethyl)-phenyl]-5-methyl-1,2,4-oxadiazole are added. The reaction mixture is stirred at 100° for 5 days. After cooling, the mixture is filtered, and the filtrate is evaporated. The residue is purified by preparative HPLC.

Yield: 42.1 mg (10%) of "A42" TFA salt; HPLC: Rt=2.003 min. (method B); LC-MS: [M+H]$^+$=448 at Rt=1.282 min.

EXAMPLE 5

The preparation of 3-[3-(5-methyl-1,2,4-oxadiazol-3-yl)benzyl]-6-[3-(4-methylpiperazin-1-yl)propionyl]-3H-benzoxazol-2-one ("A43") is carried out analogously to the following scheme:

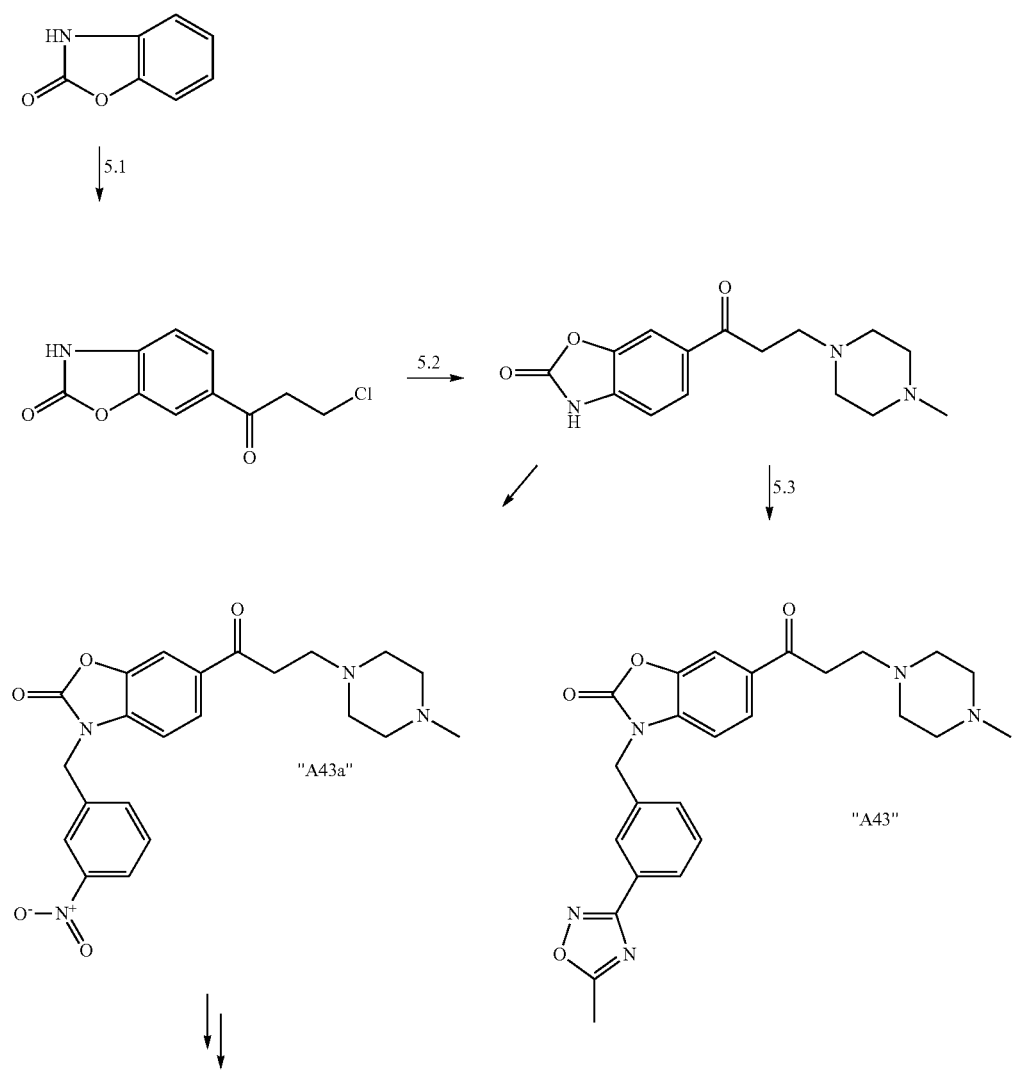

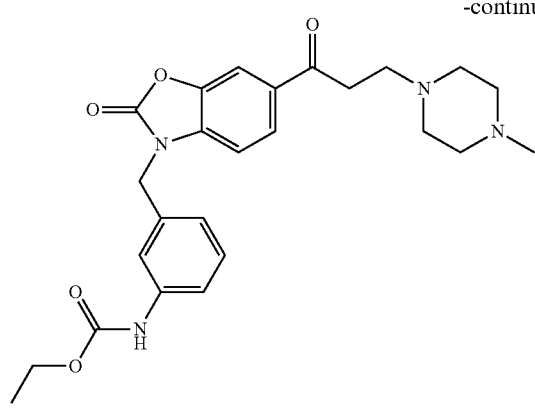

5.1 95.2 g (0.7 mol) of aluminium chloride are initially introduced in a 1 l three-necked flask with stirrer, condenser, thermometer and dropping funnel, and 27 g (0.2 mol) of benzoxazolone [preparation analogous to Example 2.1] are added with stirring, during which a stirrable, dark-brown slurry forms after a short time (weakly exothermic reaction). The mixture is stirred for a further 5 minutes, and 29.7 ml (0.3 mol) of 3-chloropropionyl chloride are then slowly added dropwise. The mixture is subsequently stirred at 80° for 2 h. After cooling, the mixture is diluted with 100 ml of dichloromethane, stirred for 15 minutes and stirred into 500 g of ice. The precipitate is filtered off with suction, washed with a little dichloromethane and then with water and dried. The crude crystals (41.2 g) are suspended in 100 ml of isopropanol, filtered off with suction, washed with 50 ml of isopropanol and then with MTB ether and dried; yield: 34.1 g (76%) of 6-(3-chloropropionyl)-3H-benzoxazol-2-one.

5.2 2.95 ml (26.6 mmol) of 1-methylpiperazine, 4 g (29.2 mmol) of potassium carbonate and 44 g (266 mmol) of potassium iodide are initially introduced in 70 ml of DMF, 6 g (26.6 mmol) of 6-(3-chloropropionyl)-3H-benzoxazol-2-one are added, and the mixture is stirred overnight at RT. The reaction mixture is filtered with suction, and the residue is washed a number of times with THF. The residue is dissolved in sodium hydrogen-carbonate solution, NaCl is added to the aqueous phase, and the mixture is extracted twice with 250 ml of ethyl acetate each time. The organic phase is dried over sodium sulfate and evaporated in a rotary evaporator; yield: 640 mg of 6-[3-(4-methylpiperazin-1-yl)propionyl]-3H-benzoxazol-2-one.

5.3 148 mg (0.45 mmol) of 6-[3-(4-methylpiperazin-1-yl) propionyl]-3H-benzoxazol-2-one and 243 mg (1.76 mmol) of potassium carbonate are suspended in 10 ml of acetonitrile, and 126 mg (0.50 mmol) of 3-[3-(bromomethyl)phenyl]-5-methyl-1,2,4-oxadiazole are added. The reaction mixture is stirred at 80° for 5 days. After cooling, the mixture is filtered, and the filtrate is evaporated. The residue is purified by preparative HPLC. Yield: 42.2 mg (16%) of "A43" TFA salt; HPLC: Rt=2.902 min. (method B); LC-MS: M+H=462 at Rt=1.251 min.

The following is obtained in a corresponding manner to the reaction scheme described above:

| No. | Structure | ESI (M + H) | Rt in min |
|---|---|---|---|
| "A43a" | (structure shown) trifluoroacetate | 425 | 1.81 (method B) |

EXAMPLE 6

Preparation of N,N-dimethyl-N'-{2-[3-(5-methyl-2-oxobenzoxazol-3-yl-methyl)phenyl]pyrimidin-5-yl}formamidine ("A44")

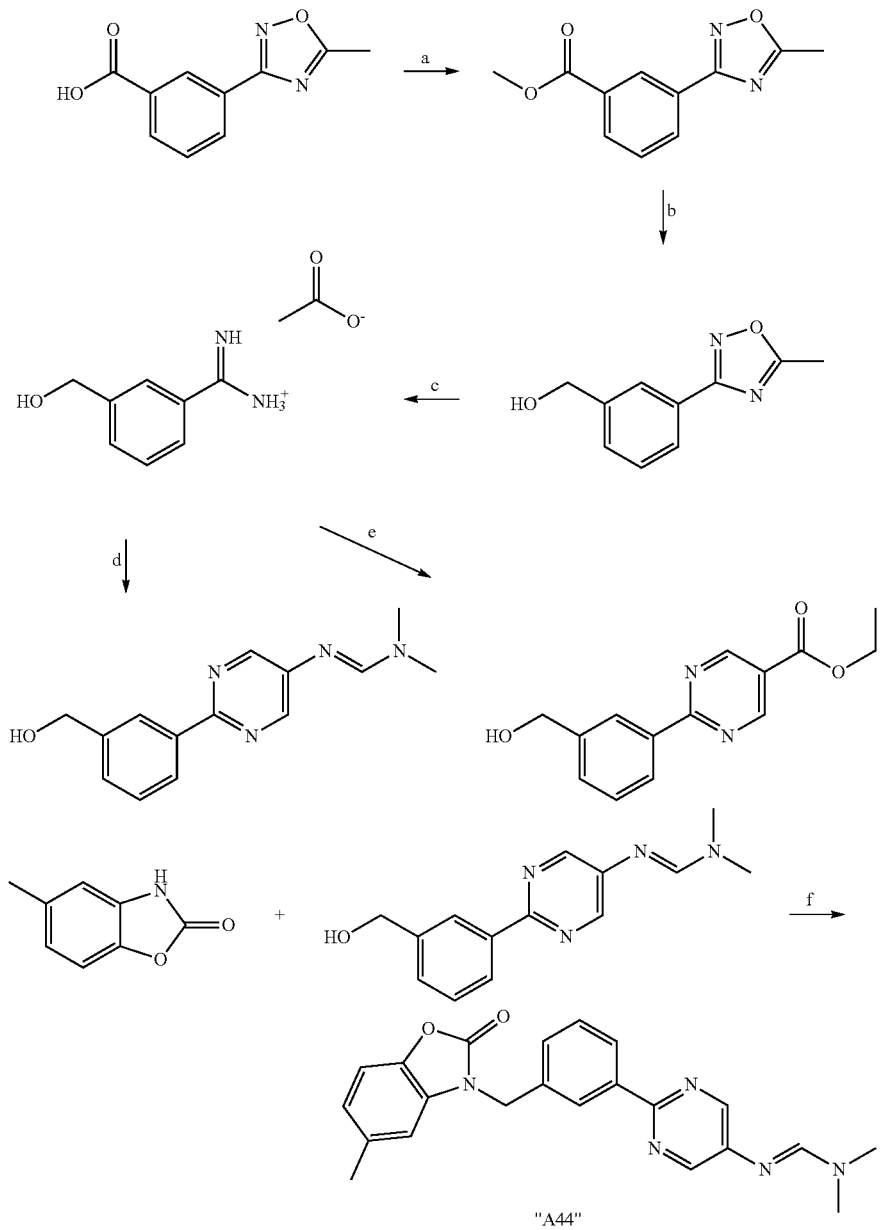

a)
3.781 g of 3-(5-methyl-1,2,4-oxadiazol-3-yl)benzoic acid (1858 mmol) are suspended in 100 ml of absolute methanol, 2.694 ml of thionyl chloride (37.13 mmol) are added dropwise with ice/$H_2O$ cooling and stirring, and the mixture is stirred without cooling for a further 72 h, during which a clear soln. forms.

The solvent is removed, the residue is dissolved in 100 ml of dichloromethane, the solution is shaken with 50 ml of saturated $NaHCO_3$ soln., dried over sodium sulfate and evaporated to dryness, and the residue is crystallised from diethyl ether/petroleum ether.

Yield: 3.46 g (15.86 mmol)=85% of methyl 3-(5-methyl-1,2,4-oxadiazol-3-yl)benzoate; m.p. 81-82°; ESI 219 (M+H), HPLC: Rt=2.65 min (method B).

b)
3.46 g of methyl 3-(5-methyl-1,2,4-oxadiazol-3-yl)benzoate (15.86 mmol) are dissolved in absolute THF in a 250 ml three-necked flask, 0.691 g of $LiBH_4$ (31.71 mmol) are introduced in portions with ice/$H_2O$ cooling and stirring, and the mixture is stirred without cooling for a further 20 h. Work-up: the pH is adjusted to 7 by slow dropwise addition of 1 N HCl (vigorous foaming) with stirring, the mixture is diluted with 100 ml of $H_2O$ and shaken with 3×50 ml of dichloromethane, the combined extracts are washed with 100 ml of H₂O, dried over sodium sulfate and evaporated to dryness, and the residue is purified by chromatography.

The crude chromatography residue is recrystallised from diethyl ether/-petroleum ether.

Yield: 1.643 g (8.64 mmol)=54% of [3-(5-methyl-1,2,4-oxadiazol-3-yl)-phenyl]methanol; m.p. 57-58°; ESI 191 (M+H); HPLC: Rt=2.38 min (method C).

c)

1 g of Raney nickel (water-wet) is added to 800 mg of [3-(5-methyl-1,2,4-oxadiazol-3-yl)phenyl]methanol (4.21 mmol) in a mixture of 10 ml of methanol, 1 ml of glacial acetic acid and 1 ml of water, and the mixture is hydrogenated at room temperature and atmospheric pressure until 91 ml of hydrogen have been taken up. For work-up, the catalyst is filtered off, and the solution which remains is evaporated to dryness. Purification is carried out by crystallisation from methanol/diethyl ether; yield: 716 mg (3.41 mmol)=81% of 3-hydroxymethylbenzamidinium acetate; m.p. 188°; ESI 151 (M+H); HPLC: Rt=0.51 min (method C).

d)

716 mg of 3-hydroxymethylbenzamidinium acetate (3.41 mmol) and 1662 mg of aminoreductone precursor (Acres Order No. 292440050) are suspended in 15 ml of absolute methanol under a nitrogen atmosphere in a 100 ml three-necked flask, a freshly prepared solution of 0.235 g of sodium in 5 ml of absolute methanol is added dropwise with stirring, and the mixture is subsequently stirred at 60° C. for 30 min, during which a clear solution forms.

For work-up, the reaction mixture is diluted with 50 ml of dichloromethane, washed twice with 20 ml of H₂O, dried over sodium sulfate and evaporated to dryness, and the residue is purified by chromatography (FlashMaster II gradient 0-5% of methanol in dichloromethane in 40 min); yield 597 mg (2.33 mmol)=68% of N'-[2-(3-hydroxymethylphenyl)pyrimidin-5-yl]-N,N-dimethylformamidine; m.p. 105-106°; ESI 257 (M+H), HPLC: Rt=2.24 min (method C).

e)

190 mg of ethyl 2-formyl-3-oxopropionate (1.32 mmol) are dissolved in 5 ml of absolute pyridine, and 252 mg of 3-hydroxymethylbenzamidinium acetate (1.2 mmol) are added. This suspension is heated at 90° for 2 hours in a heating block, during which everything dissolves. The reaction mixture is stirred into 30 ml of water. The deposited crystals are filtered off with suction, washed well with water and dried overnight at 80° in vacuo in a drying cabinet; yield: 279 mg of beige crystals=90% of theory; ESI 301 (M+H), HPLC: Rt=3.06 min (method B).

f)

149 mg (1.00 mmol) of 5-methylbenzoxazolone are suspended in 5 ml of absolute THF under a protective-gas atmosphere in a 25 ml single-necked flask, and 249 mg (1.15 mmol) of N'-[2-(3-hydroxymethylphenyl)pyrimidin-5-yl]-N,N-dimethylformamidine and 397 mg (1.50 mmol) of triphenylphosphine are subsequently added at room temperature. The reaction mixture is stirred at RT for 30 min. The reaction batch is subsequently cooled in an ice bath, and 310 µl (1.50 mmol) of diisopropyl azodicarboxylate are added dropwise at 0°, and, when the addition is complete, the mixture is stirred at RT for a further 2 h. The reaction batch is diluted with 30 ml of diethyl ether, and the resultant crystals are filtered off with suction, washed with diethyl ether and dried at 50° in a vacuum drying cabinet.

Yield: 263 mg (0.68 mmol)=68% of N,N-dimethyl-N'-{2-[3-(5-methyl-2-oxobenzoxazol-3-ylmethyl)phenyl]pyrimidin-5-yl}formamidine ("A44"); ESI 387 (M+H); HPLC: Rt=3.71 min (method C);

¹H NMR (250 MHz, DMSO-d₆) δ [ppm] 8.486 (s, 2H), 8.309 (s, 1H), 8.242 (m, 1H), 8.007 (s, 1H), 7.473 (m, 2H), 7.208 (s, 1H), 7.097 (d, 1H), 6.987 (d, 1H), 5.114 (s, 2H), 3.070 (s, 3H), 2.983 (s, 3H), 2.313 (s, 3H).

EXAMPLE 7

5-Methyl-3-[3-(5-methylpyrimidin-2-yl)benzyl]-3H-benzoxazol-2-one ("A45") is obtained analogously to the following scheme:

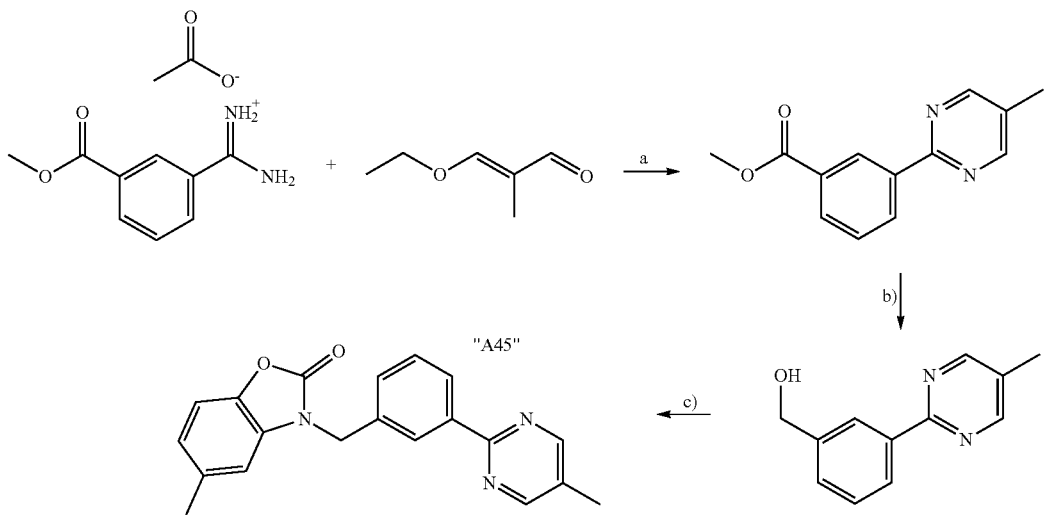

Step a:

Preparation of methyl 3-(5-methylpyrimidin-2-yl)benzoate 2.41 g (10 mmol) of methyl 3-carbamimidoylbenzoate acetate are suspended in 40 ml of methanol, 1.31 ml (11 mmol) of 3-ethoxymethacrolein and 2.04 ml of 30% sodium methoxide in methanol are added, and the mixture is stirred at 50° C. for 15 h. The reaction mixture is evaporated to dryness, and 100 ml of water are added. The precipitate formed is filtered off with suction and dried in vacuo. The crude product is reacted further without further purification; product: 1.65 g; ESI: 229 (M+H).

Step b:

Preparation of [3-(5-methylpyrimidin-2-yl)phenyl]methanol 1.65 g (7.16 mmol) of methyl 3-(5-methylpyrimidin-2-yl) benzoate, dissolved in 7 ml of THF, are added dropwise under a nitrogen atmosphere to a suspension of 272 mg (7.16 mmol) of lithium aluminium hydride in 7 ml of THF, and the mixture is stirred at room temperature for 24 h. 4 ml of a THF/water mixture (1:1) are subsequently added dropwise. A solution of 1.5 g of $Na_2CO_3$ in 4 ml of water is then added, the precipitate is filtered off with suction, and the residue is boiled with 2×THF/ethyl acetate and again filtered off with suction. The combined mother liquors are evaporated to dryness, the residue is dissolved in dichloromethane, and the solution is dried over sodium sulfate, filtered and again evaporated to dryness. The crude product is purified by column chromatography on silica gel; product: 500 mg; ESI: 201 (M+H).

Step c:

Preparation of 5-methyl-3-[3-(5-methylpyrimidin-2-yl)benzyl]-3H-benzoxazol-2-one 112 mg (0.75 mmol) of 5-methyl-3H-oxazolo[4,5-b]pyridin-2-one, 180 mg (0.90 mmol) of [3-(5-methylpyrimidin-2-yl)phenyl]methanol and 238 mg (0.90 mmol) of triphenylphosphine are suspended in 5 ml of THF, and the mixture is stirred for 30 min. The mixture is subsequently cooled to 0° C., and 186 µl (0.90 mmol) of diisopropyl azodicarboxylate are added. The reaction mixture is stirred at room temperature for 2 h. The reaction mixture is diluted with 20 ml of dichloromethane, washed with 2×20 ml of water, dried over sodium sulfate and evaporated. The residue is purified by column chromatography on silica gel; yield: 101 mg of "A45"; ESI: 332 (M+H); Rt=4.91 min (method C);

$^1$H NMR (250 MHz, DMSO-$d_6$) δ [ppm] 8.742 (s, 1H), 8.370 (s, 1H), 8.300 (m, 1H), 7.497 (m, 2H), 7.206 (s, 1H), 7.103 (d, 1H), 6.975 (d, 1H), 5.129 (s, 2H), 2.311 (s, 3H), 2.304 (s, 3H).

EXAMPLE 8

The preparation of N-propyl-3-{3-[6-(3-dimethylaminopropoxy)pyridazin-3-yl]benzyl}-2-oxo-2,3-dihydrobenzoxazole-5-carboxamide ("A54") is carried out analogously to the following scheme:

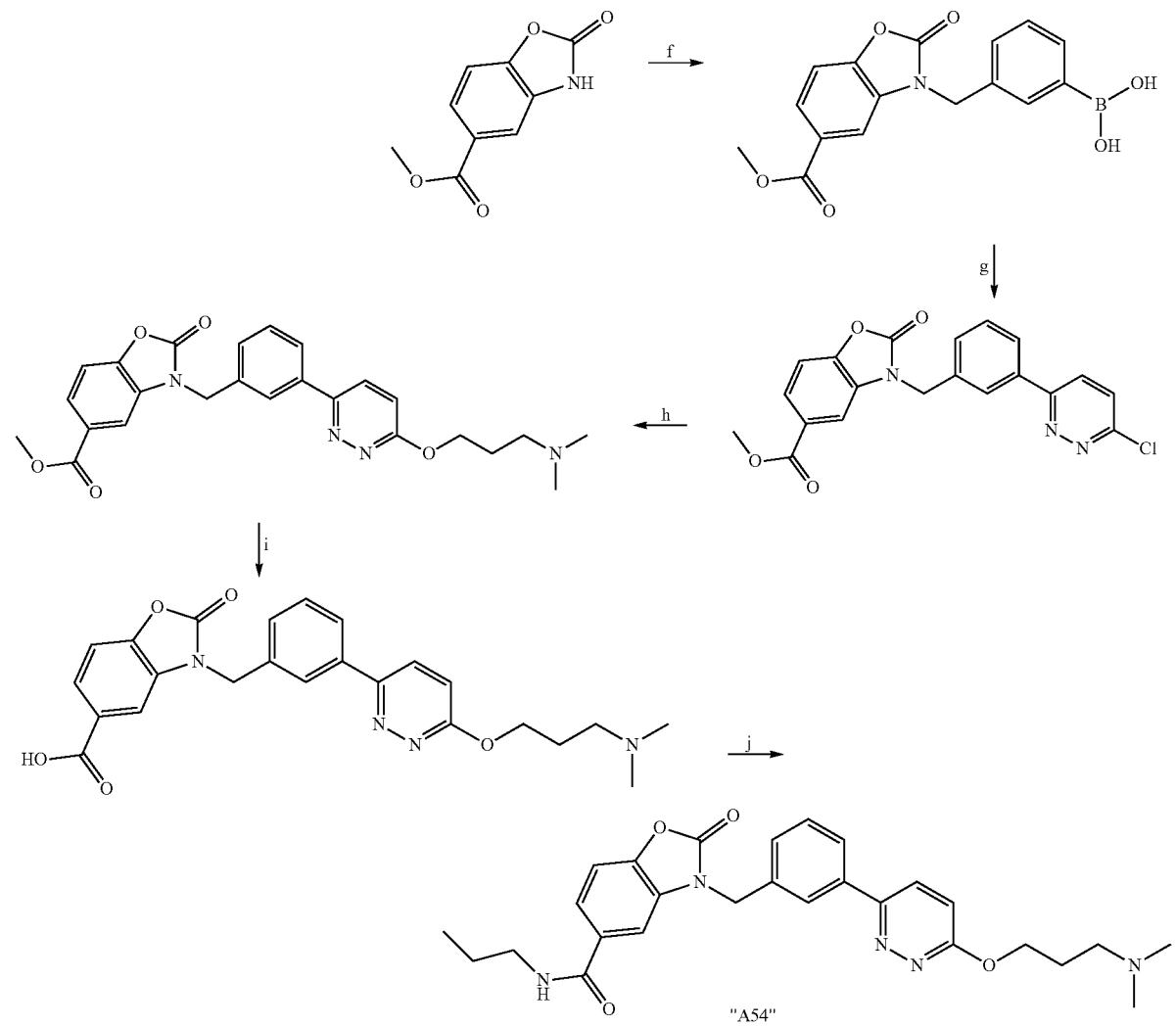

"A54"

Step f)
The preparation of the starting material methyl 2-oxo-2,3-dihydrobenzoxazole-5-carboxylate is carried out analogously to
1) Varma; Kapoor; CUSCAM; Curr. Sci.; 46; 1977; 779
2) Einhorn; Ruppert; JLACBF; Justus Liebigs Ann. Chem.; 325; 1902; 320.

The coupling to 3-hydroxymethylphenylboronic acid is carried out by standard methods.

Step g)

Preparation of methyl 3-[3-(6-chloropyridazin-3-yl)benzyl]-2-oxo-2,3-dihydrobenzoxazole-5-carboxylate The reaction of the boronic acid obtained in step g) with 3-chloro-6-iodopyridazine (preparation analogous to Goodman, Allan J.; Stanforth, Stephen P.; Tarbit, Brian; TETRAB; Tetrahedron; EN; 55; 52; 1999; 15067-15070) is carried out analogously to Goodman, Allan J.; Stanforth, Stephen P.; Tarbit, Brian; Tetrahedron; 55; 52; 1999; 15067-15070.

Step h)
The preparation of methyl 3-{3-[6-(3-dimethylaminopropoxy)pyridazin-3-yl]-benzyl}-2-oxo-2,3-dihydrobenzoxazole-5-carboxylate is carried out analogously to Heinisch, Gottfried; Langer, Thierry; J. Heterocycl. Chem.; 30; 6; 1993; 1685-1690.

Step i)
Acidic Ester Cleavage by Standard Methods

Step j)
Formation of the Amide by Standard Methods (Reagents TBTU/HOBt)

The following compounds are obtained analogously:

| No. | Name and/or structure | LCMS retention time [min]/LCMS mass $[M + H]^+$/ m.p. [° C.] |
|---|---|---|
| "A55" | | |
| "A56" | | |
| "A57" | | |
| "A58" | | |

EXAMPLE 9

The preparation of 3-(4-methylpiperazin-1-yl)propyl {3-[6-(1-hydroxyethyl)-2-oxobenzoxazol-3-ylmethyl]phenyl}carbamate ("A9") is carried out analogously to the following scheme:

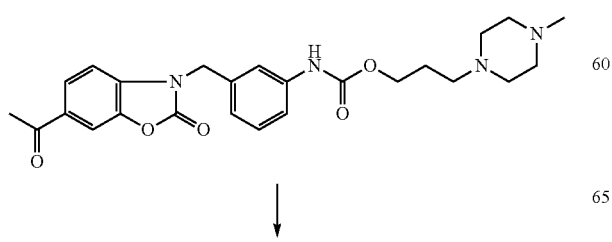

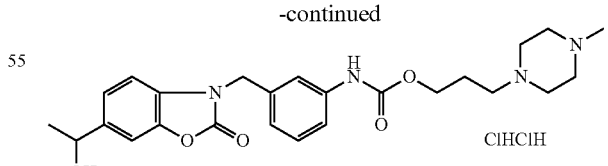

"A 9"

477 mg (1.02 mmol) of 3-(4-methylpiperazin-1-yl)propyl [3-(6-acetyl-2-oxo-benzooxazol-3-ylmethyl)phenyl]carbamate are dissolved in 20 ml of ethanol, and 38.7 mg (1.02 mmol) of sodium borohydride are added in portions with cooling. The mixture is stirred at room temperature for a further 1 h, and the clear reaction solution is diluted with water and extracted with dichloromethane. The organic phase is dried, filtered and evaporated to dryness. The residue is purified by column chromatography on silica gel. The product is precipitated as the dihydrochloride using 4 N dioxane/HCl and ether, giving 322 mg of "A9"; m.p. 215° C.; ESI 469 (M+H); HPLC: Rt=3.63 min (method A).

The following compound is obtained analogously:

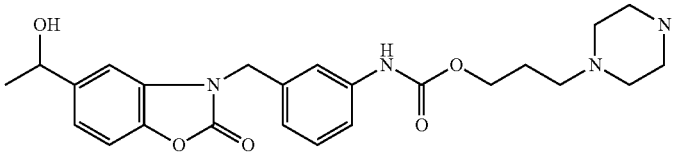 [SMILES: CC(O)c1ccc2oc(=O)n(Cc3cccc(NC(=O)OCCCN4CCNCC4)c3)c2c1]

| "A28" | 3-(4-Methylpiperazin-1-yl)propyl {3-[5-(1-hydroxy-ethyl)-2-oxobenzoxazol-3-ylmethyl]phenyl}carbamate dihydrochloride [obtainable from "A8" by NaBH$_4$ reduction] | 1.439/469.2/ 140 (decomposition) ESI: 469 (M + H), HPLC: Rt = 3.65 min (method A) |

EXAMPLE 10

The preparation of methyl 3-{3-[5-(3-dimethylaminopropoxy)pyrimidin-2-yl]-benzyl}-2-oxo-2,3-dihydrobenzoxazole-5-carboxylate ("A64") is carried out analogously to the following scheme:

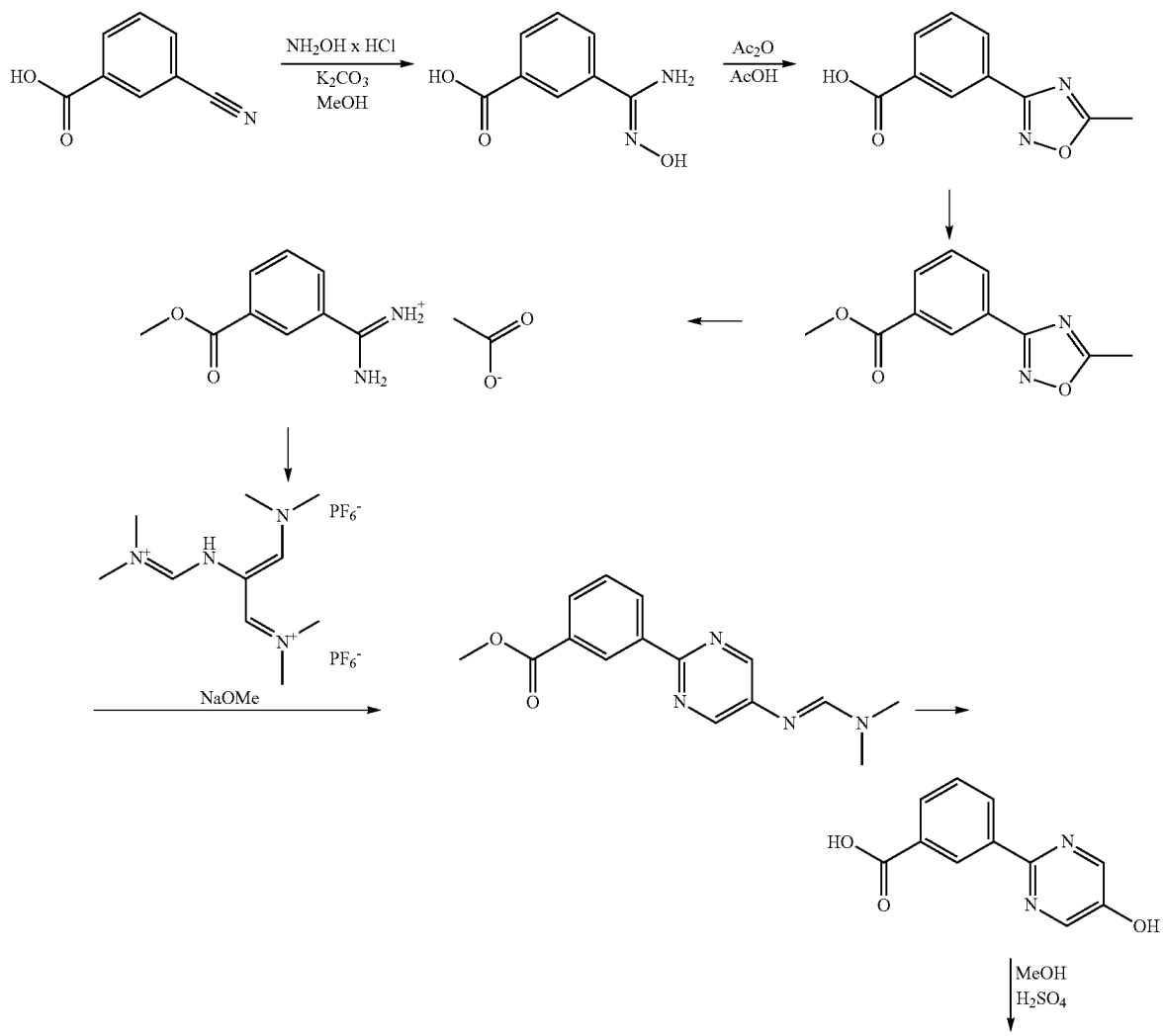

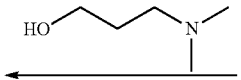
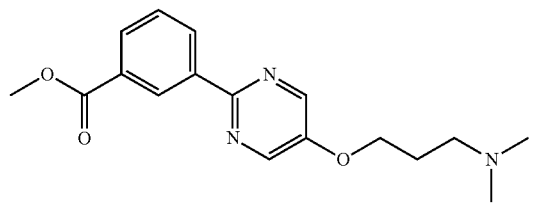 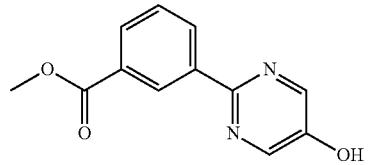

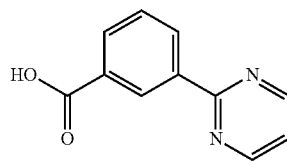

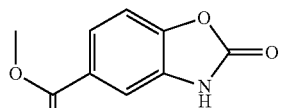

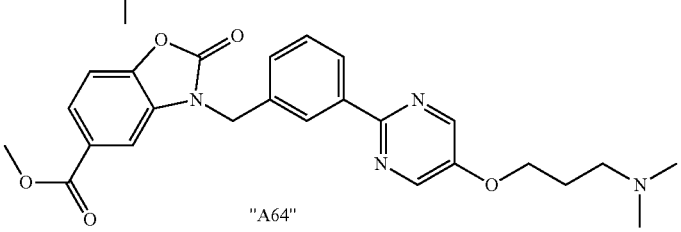

"A64"

Step 1:

Preparation of 3-(N-hydroxycarbamimidoyl)benzoic acid 1382 g (10.0 mop) of potassium carbonate are added in portions with stirring to a suspension, held at 30° C., of 500 g (3.40 mol) of 3-cyanobenzoic acid in 8 l of methanol. 695 g (10.0 mol) of hydroxylammonium chloride are subsequently added in small portions at an internal temperature of 40-45° C. The reaction mixture is then heated at the boil for 15 hours. The reaction mixture is evaporated in vacuo, and the residue is dissolved in water and acidified using 37% aqueous hydrochloric acid. The resultant precipitate is filtered off with suction, washed with water and dried in vacuo: 3-(N-hydroxycarbamimidoyl)benzoic acid as colourless crystals; m.p. 208° C.; ESI 181 (M+H).

Step 2:

Preparation of 3-(5-methyl-1,2,4-oxadiazol-3-yl)benzoic acid

A mixture of 614 g (3.41 mol) of 3-(N-hydroxycarbamimidoyl)benzoic acid, 756 ml (8.0 mol) of acetic anhydride and 2 l of acetic acid is heated at a temperature of 118° C. for 14 hours. The reaction mixture is cooled to 6° C. and filtered with suction. The residue is taken up in 2 l of water, filtered off with suction and washed well with water. The residue is recrystallised from ethanol/water: 3-(5-methyl-1,2,4-oxadiazol-3-yl) benzoic acid as colourless crystals; m.p. 225° C.; ESI 205 (M+H).

Step 3:

Preparation of methyl 3-(5-methyl-1,2,4-oxadiazol-3-yl)benzoate 7.83 ml (147 mmol) of concentrated sulfuric acid are added to a suspension of 30.0 g (147 mmol) of 3-(5-methyl-1,2,4-oxadiazol-3-yl)benzoic acid in 150 ml of methanol, and the mixture is heated at the boil for 18 hours. The reaction mixture is cooled in an ice bath, water is added, and the solid is filtered off with suction and washed well with water:methyl 3-(5-methyl-1,2,4-oxadiazol-3-yl)benzoate as colourless crystals; m.p. 81° C.; ESI 219 (M+H); HPLC: Rt=2.65 min (method B).

Step 4:

Preparation of methyl 3-carbamimidoylbenzoate acetate 150 ml of acetic acid, 150 ml of water and 50 g of water-moist Raney nickel are added to a solution of 327 g (1.47 mol) of methyl 3-(5-methyl-1,2,4-oxadiazol-3-yl)benzoate in 3 l of methanol, and the mixture is hydrogenated at room temperature and atmospheric pressure for 18 hours. The catalyst is filtered off, and the filtrate is evaporated. The residue is taken up in tert-butyl methyl ether, heated to the boil and filtered off with suction. The residue is dried in vacuo: 3-methoxycarbonylbenzamidinium acetate as colourless crystals; m.p. 222° C.; ESI 179 (M+H); HPLC: Rt=1.40 min (method B).

Step 5:

Preparation of methyl 3-[5-(dimethylaminomethyleneamino)pyrimidin-2-yl]-benzoate 2.2 l of a freshly prepared 1.5 M sodium methoxide solution are added dropwise with stirring to a suspension of 259 g (1.09 mol) of 3-methoxycarbonylbenzamidinium acetate and 528 g (1.08 mol) of ({2-dimethylamino-1-[dimethylimmoniomethyl]vinylamino}methylene)dimethyl-ammonium dihexafluorophosphate ("aminoreductone precursor", prepared in accordance with C. B. Dousson at al., Synthesis 2005, 1817) in 1 l of methanol. The reaction mixture is then warmed to 60° C. over the course of 40 min and held at this temperature for 30 min. The reaction mixture is then cooled to room temperature, diluted with 10 l of dichloromethane and washed three times with 5 l of water each time. The organic phase is dried over sodium sulfate and evaporated. The residue is recrystallised from ethyl acetate: methyl 3-[5-(dimethylaminomethyleneamino)pyrimidin-2-yl]-benzoate as beige crystals; m.p. 146° C.; ESI 285 (M+H); HPLC: Rt=2.03 min (method B).

Step 6:

Preparation of 3-(5-hydroxypyrimidin-2-yl)benzoic acid 160 ml (2.88 mol) of concentrated sulfuric acid are added to a suspension of 103.5 g (364 mmol) of methyl 3-[5-(dimethylaminomethyleneamino)-pyrimidin-2-yl]benzoate in 1.3 l of water, and the mixture is heated at the boil for 4 hours. The reaction mixture is cooled to room temperature, diluted with water and filtered with suction. The residue is washed with water and dried in vacuo: 3-(5-hydroxypyrimidin-2-yl)benzoic acid as brownish crystals; m.p. 293-295° C.; ESI 217 (M+H); HPLC: Rt=3.25 min (method C).

Step 7:

Preparation of methyl 3-(5-hydroxypyrimidin-2-yl)benzoate 32.7 ml (445 mmol) of thionyl chloride are added to a suspension of 88.0 g (366 mmol) of 3-(5-hydroxypyrimidin-2-yl)benzoic acid in 1.4 l of methanol, and the mixture is heated at 80° C. for 2 hours. 20 ml (276 mmol) of thionyl chloride and, after 2 hours, a further 10 ml (138 mmol) of thionyl chloride are then added. After each addition, the reaction mixture is stirred at 80° C. for 2 hours. The reaction mixture is concentrated to a volume of about 300 ml in vacuo. The resultant precipitate is filtered off and dried in vacuo: methyl 3-(5-hydroxypyrimidin-2-yl)benzoate as brownish crystals; m.p. 219-223° C., ESI 231 (M+H); HPLC: Rt=3.87 min (method C).

Step 8:

Preparation of methyl 3-[5-(3-dimethylaminopropoxy)pyrimidin-2-yl]benzoate

A solution, kept under nitrogen, of 6.1 g (26.5 mmol) of methyl 3-(5-hydroxypyrimidin-2-yl)benzoate, 10.5 g (39.8 mmol) of triphenylphosphine and 4.76 ml (39.8 mmol) of 3-(dimethylamino)-1-propanol in 200 ml of THF is cooled in an ice bath, and 8.21 ml (39.8 mmol) of diisopropyl azodicarboxylate are subsequently slowly added dropwise with stirring. After stirring at room temperature for 2 hours, the reaction mixture is evaporated in vacuo. The residue is partitioned between dichloromethane and saturated aqueous potassium hydrogensulfate solution. The aqueous phase is separated off, adjusted to a pH of 12 using saturated aqueous sodium hydroxide solution and extracted twice with dichloromethane. The organic phase is dried over sodium sulfate and evaporated. The residue is chromatographed on a silica-gel column with dichloromethane/methanol as eluent: methyl 3-[5-(3-dimethylaminopropoxy)pyrimidin-2-yl]benzoate as colourless crystals; m.p. 66° C.; ESI 316 (M+H); HPLC: 2.18 min (method B).

Step 9:

Preparation of {3-[5-(3-dimethylaminopropoxy)pyrimidin-2-yl]phenyl}-methanol 200 ml of a 1 M solution of diisobutylaluminium hydride in THF are added dropwise with stirring to a solution, kept under nitrogen, of 12.6 g (40.0 mmol) of methyl 3-[5-(3-dimethylaminopropoxy)pyrimidin-2-yl]benzoate in 200 ml of THF. After the mixture has been stirred at room temperature for 1 hour, 10 ml of a saturated aqueous sodium sulfate solution are added dropwise. The resultant precipitate is filtered off with suction and washed with dichloromethane. The filtrate is dried over sodium sulfate and evaporated. The residue is taken up in a mixture of diethyl ether and petroleum ether. The resultant precipitate is filtered off with suction, washed with petroleum ether and dried in vacuo: {3-[5-(3-dimethylaminopropoxy)pyrimidin-2-yl]phenyl}methanol as colourless crystals; m.p. 95-97° C.; ESI 288 (M+H); HPLC: Rt=2.35 min (method B).

Step 10:

Preparation of methyl 3-{3-[5-(3-dimethylaminopropoxy)pyrimidin-2-yl]-benzyl}-2-oxo-2,3-dihydrobenzoxazole-5-carboxylate 1.84 g (9.5 mmol) of methyl 2-oxo-2,3-dihydrobenzoxazole-5-carboxylate and 4.75 g (14.25 mmol) of polymer-bound triphenylphosphine (3 mmol/g) are added to a solution of 3.03 g (10.45 mmol) of {3-[5-(3-dimethylaminopropoxy)pyrimidin-2-yl]phenyl}methanol in 40 ml of THF. The suspension is shaken at room temperature for 30 min. The suspension is cooled in an ice bath, and 3.35 g (14.25 mmol) of di-tert-butyl azodicarboxylate are added in portions. After the mixture has been stirred at room temperature for 24 h, a further 4.75 g (14.25 mmol) of polymer-bound triphenylphosphine (3 mmol/g) and 3.35 g (14.25 mmol) of di-tert-butyl azodicarboxylate are added, and the mixture is shaken at room temperature for a further 24 h. The reaction mixture is filtered, the filtrate is evaporated to dryness, and the residue is purified by column chromatography on silica gel, giving 947 mg of "A64"; m.p. 125° C., ESI: 463 (M+H); Rt=3.07 min (method C);

$^1$H-NMR (DMSO-d$_6$, δ in ppm): 0.636 (S, 2H), 8.331 (SB, 1H), 8.250 (D, 1H), 7.806 (M, 2H), 7.514 (M, 3H), 5.251 (S, 2H), 4.217 (T, 2H), 3.829 (S, 3H), 2.370 (T, 2H), 2.153 (S, 6H), 1.895 (T, 2H).

The following compounds are prepared analogously. In some cases, DMF is used as solvent for better dissolution of the starting materials in step 10. In some cases, the crude products are purified by preparative HPLC. In some cases, the target compounds are dissolved in acetone and precipitated as the hydrochloride using 4 N HCl in dioxane.

The following compounds are obtained analogously:

| No. | Name and/or structure | ESI (M + H) | Rt in min |
|---|---|---|---|
| "A65" | 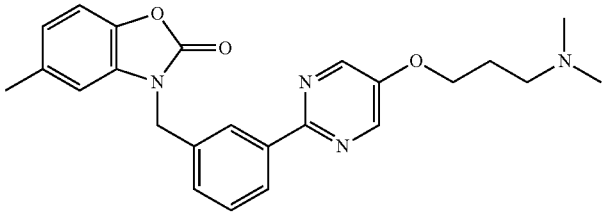<br>hydrochloride | 419 | 2.52 (method B) |

-continued
| No. | Name and/or structure | ESI (M + H) | Rt in min |
|---|---|---|---|
| "A66" | 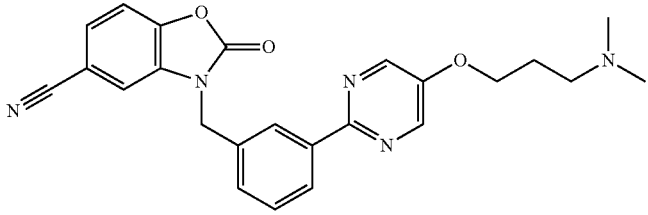<br>hydrochloride | 430 | 2.36 (method B) |
| "A67" | 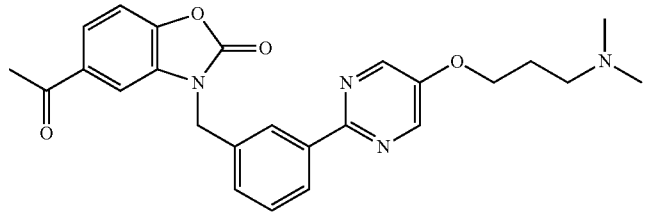 [SMILES: CC(=O)c1ccc2oc(=O)n(Cc3cccc(-c4ncc(OCCCN(C)C)cn4)c3)c2c1] | 447 | 2.33 (method B) |
| "A68" | 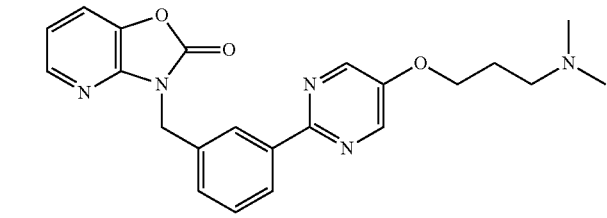 [SMILES: CN(C)CCCOc1cnc(-c2cccc(Cn3c(=O)oc4cccnc43)c2)nc1] | 446 | 2.25 (method B) |
| "A69" | 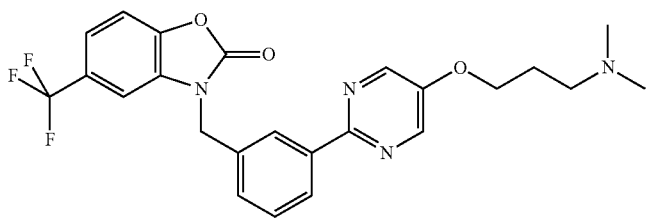<br>trifluoroacetate | 473 | 2.65 (method B) |
| "A70" | 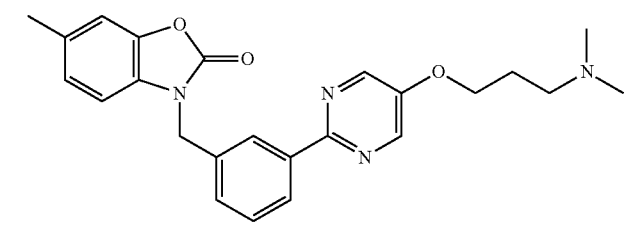<br>hydrochloride | 419 | 2.52 (method B) |
| "A71" | 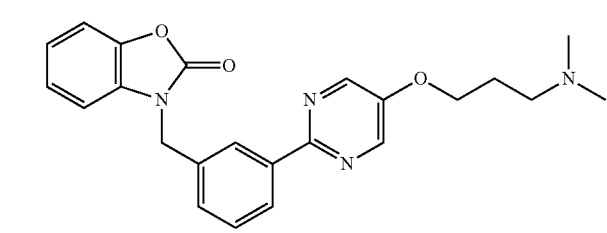<br>hydrochloride | 405 | 2.39 (method B) |

-continued
| No. | Name and/or structure | ESI (M + H) | Rt in min |
|---|---|---|---|
| "A72" | 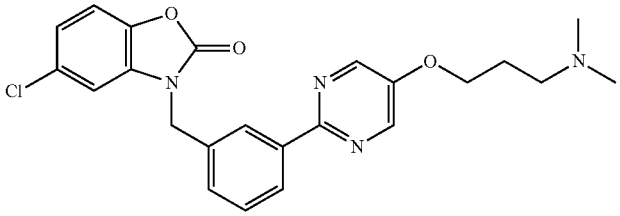<br>trifluoroacetate | 439 | 2.54 (method B) |
| "A73" | 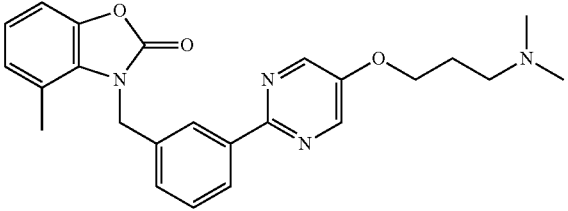 [SMILES: Cc1cccc2oc(=O)n(Cc3cccc(-c4ncc(OCCCN(C)C)cn4)c3)c12] | 419 | 2.48 (method B) |
| "A74" | 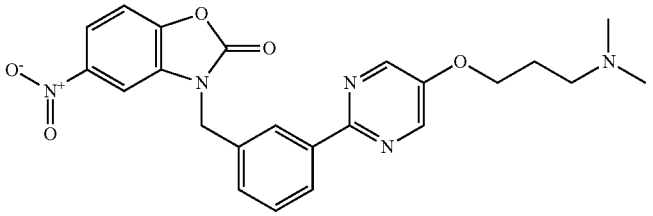 [SMILES: CN(C)CCCOc1cnc(-c2cccc(Cn3c(=O)oc4ccc([N+](=O)[O-])cc43)c2)nc1] | 450 | 2.41 (method B) |
| "A75" | 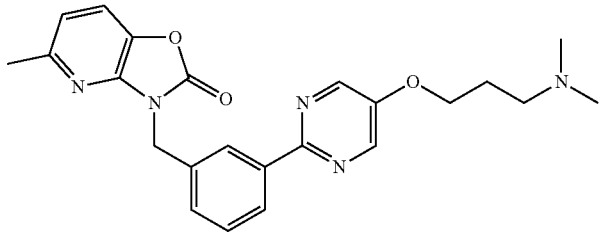 | 420 | 2.36 (method B) |
| "A76" | 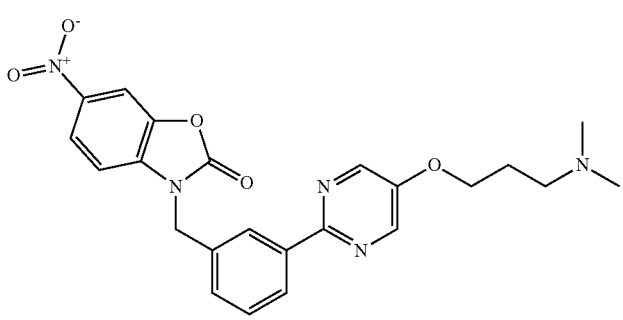<br>trifluoroacetate | 450 | 2.43 (method B) |
| "A77" | 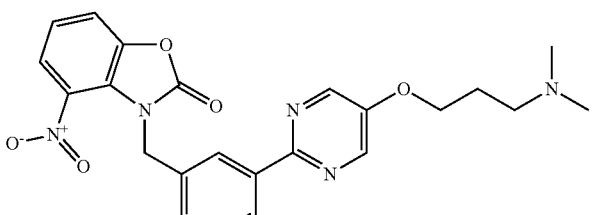<br>trifluoroacetate | 450 | 2.43 (method B) |

| No. | Name and/or structure | ESI (M + H) | Rt in min |
|---|---|---|---|
| "A78" | (5-bromo-benzoxazol-2-one linked via N to CH2-phenyl-pyrimidine-O-(CH2)3-N(CH3)2) | 484 | 2.58 (method B) |
| "A79" | (5-methyl-oxazolopyridin-2-one linked via N to CH2-phenyl-pyrimidine-O-CH2CH2-morpholine) | 448 | 2.28 (method B) |
| "A80" | (5-fluoro-benzoxazol-2-one linked via N to CH2-phenyl-pyrimidine-O-(CH2)3-N(CH3)2) | 423 | 2.43 (method B) |
| "A81" | (7-chloro-benzoxazol-2-one linked via N to CH2-phenyl-pyrimidine-O-(CH2)3-N(CH3)2) | 439 | 2.56 (method B) |
| "A82" | (5-ethylsulfonyl-benzoxazol-2-one linked via N to CH2-phenyl-pyrimidine-O-(CH2)3-N(CH3)2) | 497 | 2.26 (method B) |
| "A83" | (6-acetyl-benzoxazol-2-one linked via N to CH2-phenyl-pyrimidine-O-(CH2)3-N(CH3)2) | 447 | 2.31 (method B) |

-continued

| No. | Name and/or structure | ESI (M + H) | Rt in min |
|---|---|---|---|
| "A84" | | 463 | 2.42 (method B) |
| "A85" | | 530 | 2.66 (method B) |
| "A86" | | 435 | 2.39 (method B) |
| "A87" | trifluoroacetate | 432 | 2.41 (M + H) |
| "A88" | hydrochloride | 423 | 2.43 (method B) |
| "A89" | | 435 | 2.42 (method B) |

-continued

| No. | Name and/or structure | ESI (M + H) | Rt in min |
|---|---|---|---|
| "A90" | (structure) trifluoroacetate | 432 | 2.37 (method B) |
| "A91" | (structure) | 489 | 4.27 (method C) |
| "A92" | (structure) | 514 | 2.13 (method B) |
| "A93" | (structure) hydrochloride | 441 | 2.47 (method B) |
| "A94" | (structure) trifluoroacetate | 484/ 486 | 2.57 (method B) |
| "A95" | (structure) trifluoroacetate | 406 | 2.17 (method B) |

-continued

| No. | Name and/or structure | ESI (M + H) | Rt in min |
|---|---|---|---|
| "A96" | [structure: naphtho-oxazolone linked via CH2 to phenyl-pyrimidine-O-(CH2)3-N(CH3)2] | 455 | 2.73 (method B) |
| "A97" | [structure: 5-tert-butyl-benzoxazolone linked via CH2 to phenyl-pyrimidine-O-(CH2)3-N(CH3)2] trifluoroacetate | 461 | 2.86 (method B) |
| "A98" | [structure: 6-(methoxycarbonylmethyl)-benzoxazolone linked via CH2 to phenyl-pyrimidine-O-(CH2)3-N(CH3)2] trifluoroacetate | 477 | 2.43 (method B) |
| "A99" | [structure: 5-ethyl-benzoxazolone linked via CH2 to phenyl-pyrimidine-O-(CH2)3-N(CH3)2] | 433 | 2.68 (method B) |
| "A100" | [structure: 5-chloro-6-trifluoromethyl-benzoxazolone linked via CH2 to phenyl-pyrimidine-O-(CH2)3-N(CH3)2] trifluoroacetate | 507 | 2.84 (method B) |
| "A101" | [structure: 6,7-difluoro-benzoxazolone linked via CH2 to phenyl-pyrimidine-O-(CH2)3-N(CH3)2] hydrochloride | 441 | 2.60 (method B) |

| No. | Name and/or structure | ESI (M + H) | Rt in min |
|---|---|---|---|
| "A102" | 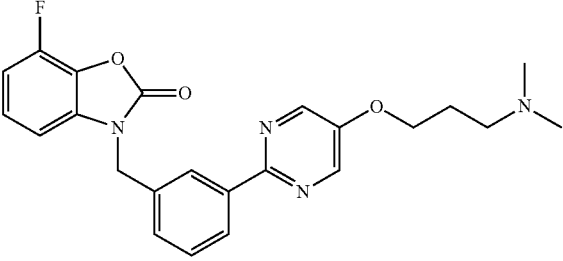hydrochloride | 423 | 2.52 (method B) |
| "A103" | 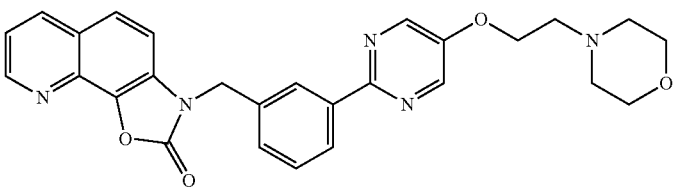 [SMILES: O=c1oc2c3ncccc3ccc2n1Cc1cccc(-c2ncc(OCCN3CCOCC3)cn2)c1] | 484 | 2.07 (method B) |
| "A104" | 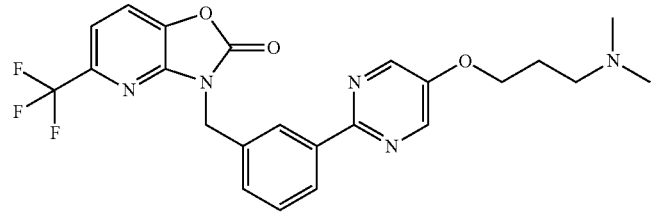 [SMILES: CN(C)CCCOc1cnc(-c2cccc(Cn3c(=O)oc4ccc(C(F)(F)F)nc43)c2)nc1] | 474 | |
| "A105" | 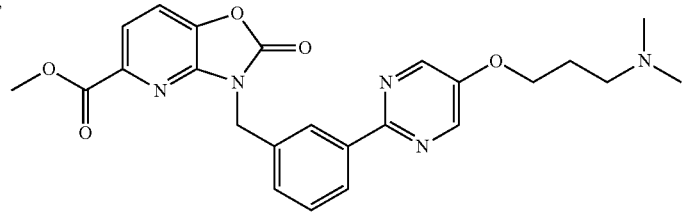 | 464 | |
| "A106" | 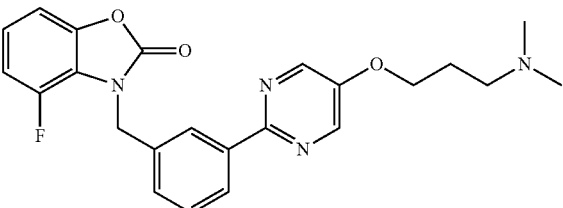trifluoroacetate | 423 | 2.49 (method B) |
| "A107" | 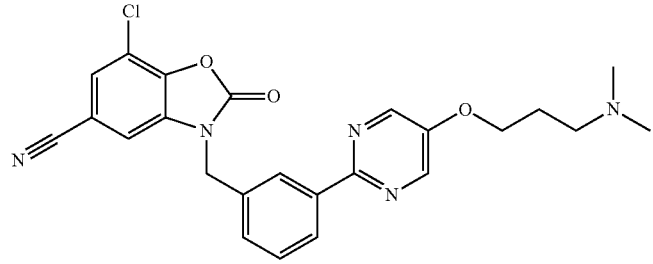trifluoroacetate | 464 | 2.59 (method B) |

| No. | Name and/or structure | ESI (M + H) | Rt in min |
|---|---|---|---|
| "A108" | 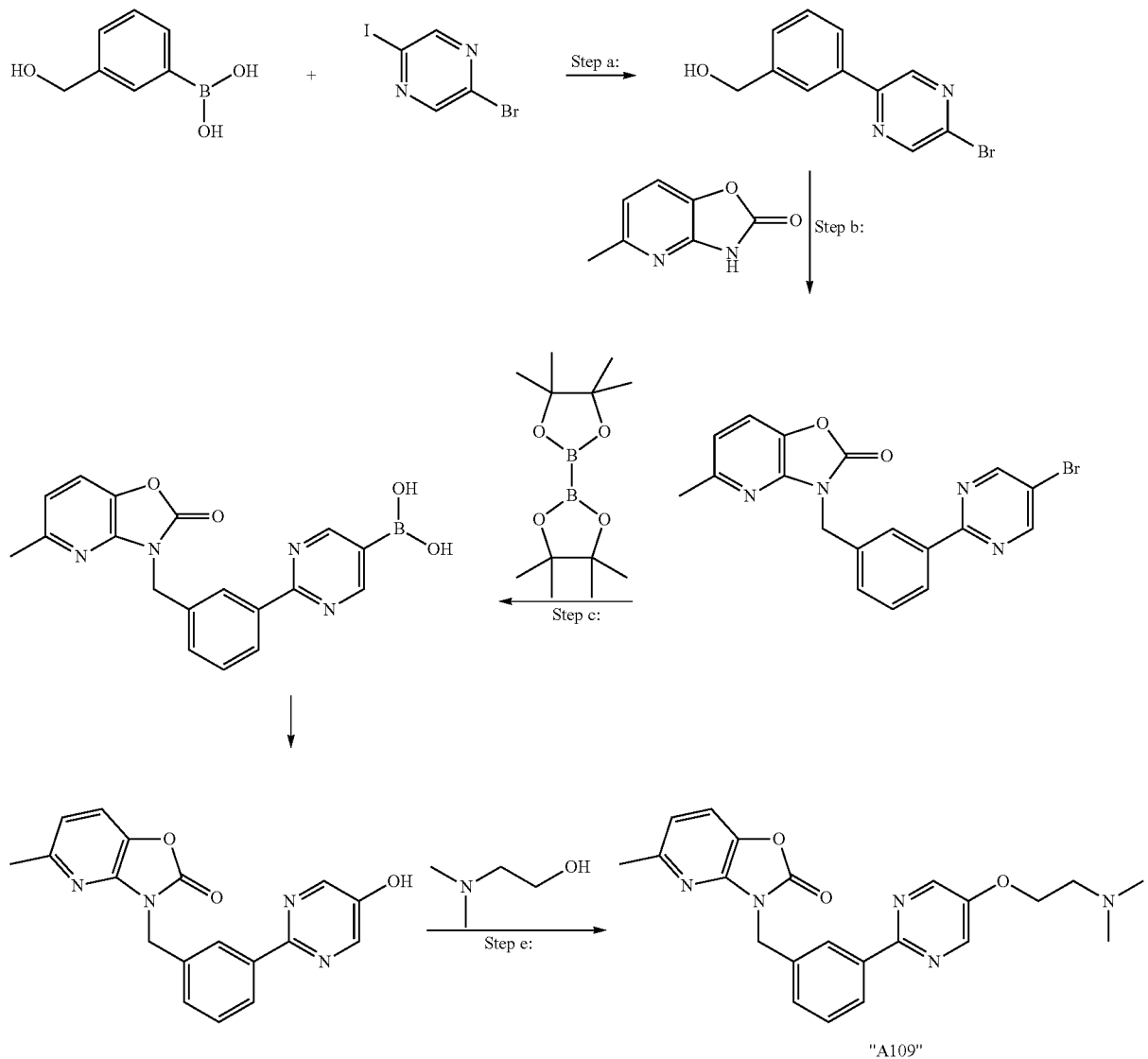 | 440 | |
EXAMPLE 11
The preparation of 3-{3-[5-(2-dimethylaminoethoxy)pyrimidin-2-yl]benzyl}-5-methyl-3H-oxazolo[4,5-b]pyridin-2-one ("A109") is carried out analogously to the following scheme:
Step a:
Preparation of [3-(5-bromopyrimidin-2-yl)phenyl]methanol
750 mg (0.65 mmol) of tetrakis(triphenylphosphine)palladium are added to a solution, kept under nitrogen, of 6.11 g (21.5 mmol) of 5-bromo-2-iodopyrimidine, 3.91 g (25.7 mmol) of 3-(hydroxymethyl)benzeneboronic acid and 9.11 g (42.9 mmol) of tripotassium phosphate trihydrate in 120 ml of dioxane and 14 ml of water, and the mixture is stirred at 90° C. for 18 hours. The reaction mixture is cooled to room temperature, tert-butyl methyl ether and water are added, and the mixture is filtered through kieselguhr. The organic phase of the filtrate is separated off, dried over sodium sulfate and evaporated. The residue is chromatographed on a silica-gel column with dichloromethane/methanol as eluent.

Product: 2.49 g; m.p. 114-117° C.; ESI: 265, 267 (M+H); HPLC: Rt=2.51 min (method B).

Step b:

Preparation of 3-[3-(5-bromopyrimidin-2-yl)benzyl]-5-methyl-3H-oxazolo-[4,5-b]pyridin-2-one 283 mg (1.87 mmol) of 5-methyl-3H-oxazolo[4,5-b]pyridin-2-one, 500 mg (1.87 mmol) of 3-(4-methylpiperazin-1-yl)propyl (3-hydroxymethylphenyl)-carbamate and 943 mg (2.83 mmol) of polymer-bound triphenylphosphine (3 mmol/g) are suspended in 15 ml of DMF, and the mixture is shaken for 30 min. 665 mg (2.83 mmol) of di-tert-butyl azodicarboxylate are subsequently added. The reaction mixture is shaken at room temperature. The reaction mixture is filtered, the residue is washed with THF, and the filtrate is evaporated. The crude product is purified by preparative HPLC; ESI: 399 (M+H); Rt=~3.12 min (method B);

$^1$H-NMR (DMSO-d$_6$, δ in ppm): 9.08 (2H, s); 8.40 (1H, b); 8.29 (1H, m); 7.65 (1H, d); 7.51-7.60 (2H, m); 7.05 (1H, d); 5.11 (2H, s); 2.46 (3H, s).

Step c:

Preparation of 2-(3-((5-methyl-2-oxooxazolo[4,5-b]pyridin-3(2H)-yl)-methyl)phenyl)pyrimidin-5-yl-5-boronic acid 374 mg (1.47 mmol) of bis(pinacolato)diboron and 334 mg (3.40 mmol) of potassium acetate are added to a suspension of 500 mg (1.13 mmol) of 3-[3-(5-bromopyrimidin-2-yl)benzyl]-5-methyl-3H-oxazolo[4,5-b]pyridin-2-one in 25 ml of DMF, and the mixture is heated at 70° C. under nitrogen. After the mixture has been stirred at this temperature for 15 minutes, 82 mg (0.12 mmol) of bis(triphenylphosphine)palladium(II) chloride are added, and the reaction mixture is stirred at 70° C. under nitrogen for 18 hours. The reaction mixture is allowed to cool to room temperature, and is then added to ice-water and stirred for 30 min. The solid formed is filtered off with suction and dried in vacuo. The product is reacted further without further purification; ESI: 363 (M+H); Rt=2.45 min (method B).

Step d:

Preparation of 3-[3-(5-hydroxypyrimidin-2-yl)benzyl]-5-methyl-3H-oxazolo-[4,5-b]pyridin-2-one 419 mg (4.2 mmol) of sodium perborate are added with ice cooling to 500 mg (1.40 mmol) of 2-(3-((5-methyl-2-oxooxazolo[4,5-b]pyridin-3(2H)-yl)methyl)phenyl)pyrimidin-5-yl-5-boronic acid in 10 ml of THF and 10 ml of water, and the mixture is stirred at room temperature for 2 hours. The reaction mixture is filtered through kieselguhr with suction. The filtrate is extracted repeatedly with dichloromethane, dried over sodium sulfate and evaporated to dryness. The crude product is reacted further without further purification; ESI: 335 (M+H); Rt=2.71 min (method B).

Step e:

Preparation of 3-{3-[5-(2-dimethylaminoethoxy)pyrimidin-2-yl]benzyl}-5-methyl-3H-oxazolo[4,5-b]pyridin-2-one 100 mg (0.3 mmol) of polymer-bound triphenylphosphine (3 mmol/g) and 30 μl (0.3 mmol) of 2-dimethylaminoethanol are added successively to a suspension of 67 mg (0.2 mmol) of 3-[3-(5-hydroxypyrimidin-2-yl)benzyl]-5-methyl-3H-oxazolo[4,5-b]pyridin-2-one in 3 ml of DMF. 69 mg (0.30 mmol) of di-tert-butyl azodicarboxylate are subsequently added. The reaction mixture is shaken at room temperature for 18 hours. A further 100 mg (0.3 mmol) of polymer-bound triphenylphosphine (3 mmol/g) and 69 mg (0.30 mmol) of di-tert-butyl azodicarboxylate are added, and the mixture is shaken at room temperature for 18 h. A further 100 mg (0.3 mmol) of polymer-bound triphenylphosphine (3 mmol/g), 69 mg (0.30 mmol) of di-tert-butyl azodicarboxylate and 30 μl (0.3 mmol) of 2-dimethylaminoethanol are subsequently added, and the mixture is shaken at room temperature for 18 h. The reaction mixture is filtered, the filtrate is evaporated in vacuo, and the residue is purified by column chromatography on silica gel, giving "A109". The crude product is purified by preparative HPLC: ESI: 406; HPLC: Rt=2.31 min (method B);

$^1$H-NMR (DMSO-d$_6$, δ in ppm): 8.69 (2H, b); 8.34 (1H, b); 8.23-8.27 (1H, m); 7.65 (1H, d); 7.48-7.52 (2H, m); 7.05 (1H, d); 5.102 (2H, s); 4.56 (2H, t); 2.89 (6H, b); 2.51 (superimposed 2H, b); 2.49 (3H, s).

The following compounds are prepared analogously. In some cases, the target compounds are dissolved in acetone and precipitated as the hydrochloride using 4 N HCl in dioxane.

| No. | Name and/or structure | ESI (M + H) | Rt in min |
|---|---|---|---|
| "A110" | (structure) | 444 | 2.45 (method B) |

-continued
| No. | Name and/or structure | ESI (M + H) | Rt in min |
|---|---|---|---|
| "A111" | 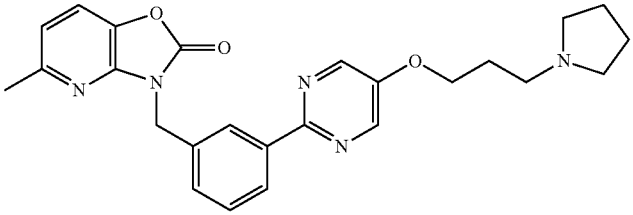 [SMILES: Cc1ccc2oc(=O)n(Cc3cccc(-c4ncc(OCCCN5CCCC5)cn4)c3)c2n1] | 446 | 2.45 (method B) |
| "A112" | 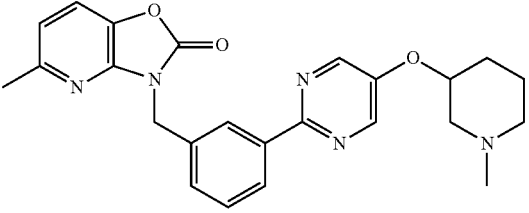 [SMILES: Cc1ccc2oc(=O)n(Cc3cccc(-c4ncc(OC5CCCN(C)C5)cn4)c3)c2n1] | 431 | 2.37 (method B) |
| "A113" | 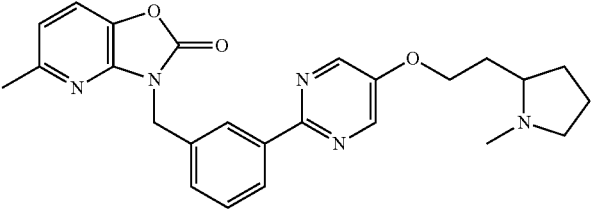 [SMILES: Cc1ccc2oc(=O)n(Cc3cccc(-c4ncc(OCCC5CCCN5C)cn4)c3)c2n1] | 446 | 2.44 (method B) |
| "A114" | 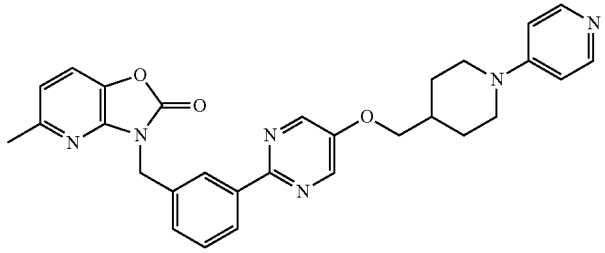<br>trifluoroacetate | 509 | 2.68 (method B) |
| "A115" | 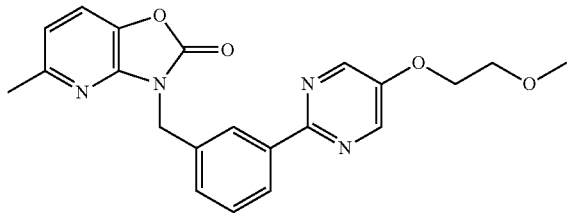 | 393 | |

-continued

| No. | Name and/or structure | ESI (M + H) | Rt in min |
|---|---|---|---|
| "A116" |  | 448 | |
| "A117" |  | 447 | |
| "A118" |  | 475 | |
| "A119" |  | 393 | |

EXAMPLE 12

The preparation of 3-{3-[5-(2,3-dihydroxypropoxy)pyrimidin-2-yl]benzyl}-5-methyl-3H-oxazolo[4,5-b]pyridin-2-one ("A120") is carried out analogously to the following scheme:

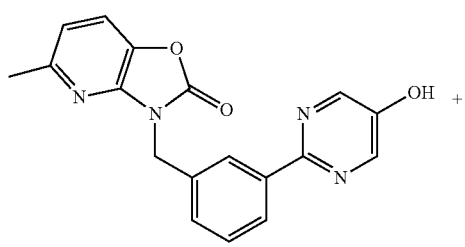

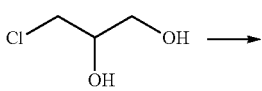

-continued

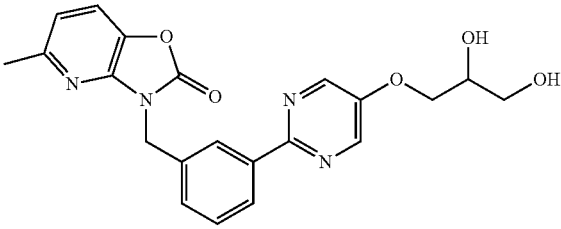

"A120"

37 mg (0.34 mmol) of 3-chloro-1,2-propanediol and 156 mg (0.48 mmol) of caesium carbonate are added to 67 mg (0.2 mmol) of 3-[3-(5-hydroxypyrimidin-2-yl)benzyl]-5-methyl-3H-oxazolo[4,5-b]pyridin-2-one in 3 ml of acetone. The reaction mixture is stirred at room temperature for 16 h and subsequently filtered, the residue is rinsed with acetone, and the filtrate is evaporated in vacuo. The residue is purified by preparative HPLC: ESI: 409, HPLC: Rt=2.50 min (method B).

The following compounds are prepared analogously. In some cases, the crude products are purified by column chromatography on silica gel. In some cases, the target compounds are dissolved in acetone and precipitated as the hydrochloride using 4 N HCl in dioxane.

| No. | Name and/or structure | ESI (M + H) | Rt in min |
|---|---|---|---|
| "A121" | | 420 | |
| "A122" | | 462 | |
| "A123" | | 450 | |
| "A124" | | 460 | |
EXAMPLE 13
Preparation of 5-methyl-3-{3-[5-(4-methylpiperazin-1-yl)pyrimidin-2-yl]-benzyl}-3H-oxazolo[4,5-b]pyridin-2-one ("A125")
13.1 Preparation of methyl 3-(5-aminopyrimidin-2-yl)benzoate
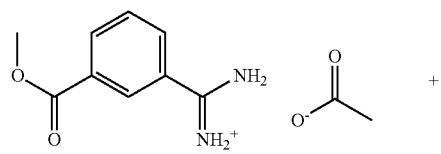
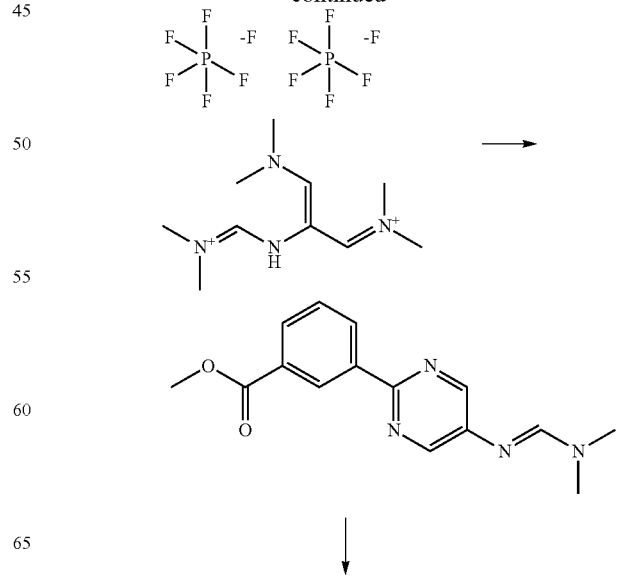
-continued

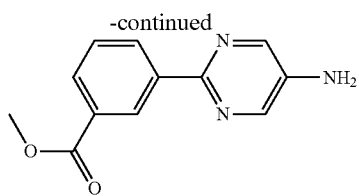

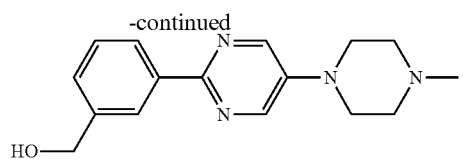

65.4 g (274 mmol) of methyl 3-carbamimidoylbenzoate are suspended in 800 ml of methanol, and 134 g (274 mmol) of aminoreductone precursor are added. 102 ml (548 mmol) of 30% sodium methoxide solution in methanol are added dropwise to this suspension. A solution forms. This is stirred at an internal temperature of 60° C. for 1 hour. After the mixture has been cooled to room temperature, a further 20 ml of 30% sodium methoxide solution in methanol are added dropwise, and the mixture is stirred at 60° C. for 1 hour. After the mixture has been cooled to room temperature, the resultant precipitate is filtered off with suction, the residue is suspended in 1 l of water, and the suspension is stirred at room temperature for 30 min. The precipitate is filtered off with suction and dried at 80° C. in a vacuum drying cabinet; yield: 68.5 g; HPLC: Rt=2.03 min (method B); LC-MS: 285 (M+H).

10.2 g (35.9 mmol) of methyl 3-[5-(dimethylaminomethyleneamino)pyrimidin-2-yl]benzoate are suspended in 1 l of methanol. 5.3 ml (107.3 mmol) of fuming sulfuric acid are added dropwise with gentle cooling (about 5-10° C.) (note, strongly exothermic reaction). When the addition is complete, the mixture is stirred firstly at room temperature for 30 min and subsequently at an oil-bath temperature of 88°. The reaction is monitored by means of HPLC. After 20 h, the clear, dark-yellow solution is evaporated to dryness. The residue is dissolved in 600 ml of ethyl acetate and washed with 2×150 ml of 1 N NaOH and 2×1 N HCl, dried over sodium sulfate and evaporated; yield: 3 g; HPLC: Rt=2.17 min (method B); LC-MS: 300 (M+H).

13.2 Preparation of {3-[5-(4-methylpiperazin-1-yl)pyrimidin-2-yl]phenyl}-methanol 2.5 g (10.9 mmol) of methyl 3-(5-aminopyrimidin-2-yl)benzoate are dissolved in 10 ml of NMP, and 2.59 g (18.5 mmol) of potassium carbonate and 3.6 g (18.5 mmol) of bis(2-chloroethyl)ethylamine hydrochloride are added. The suspension is stirred at 120° C. under an argon atmosphere for 15 h. The mixture is subsequently stirred at 140° C. for a further 12 h. After cooling to room temperature, the reaction mixture is stirred into 150 ml of water. The resultant precipitate is filtered off through kieselguhr with suction and discarded. The filtrate is adjusted to pH=14 using 32% NaOH. The slightly cloudy solution is extracted with 2×200 ml of ethyl acetate. The combined organic phases are washed with saturated sodium chloride solution, dried over sodium sulfate and evaporated to dryness and dried in vacuo. The product is reacted further without further purification;

yield: 860 mg; HPLC: Rt=2.11 min (method B); ESI: 313 (M+H).

860 mg (2.75 mmol) of methyl 3-[5-(4-methylpiperazin-1-yl)pyrimidin-2-yl]-benzoate are dissolved in 16 ml of THF, and 13.8 ml (13.8 mmol) of 1 M diisobutylaluminium hydride in THF are added dropwise at room temperature, and the reaction mixture is stirred at room temperature for 1 h. A further 13.8 ml (13.8 mmol) of 1 M diisobutylaluminium hydride in THF are added dropwise, and the reaction mixture is stirred at room temperature for 1 h. 3 ml of saturated sodium sulfate solution are added to the reaction mixture with ice cooling. Dichloromethane is added to the gelatinous mixture, which is then stirred for 30 min and filtered. The filtrate is dried over sodium sulfate and evaporated. Yield: 300 mg, yellow solid. The product is reacted further without further purification; HPLC: 1.68 min (method B); ESI: 285 (M+H).

13.3 Preparation of 5-methyl-3-{3-[5-(4-methylpiperazin-1-yl)pyrimidin-2-yl]benzyl}-3H-oxazolo[4,5-b]pyridin-2-one

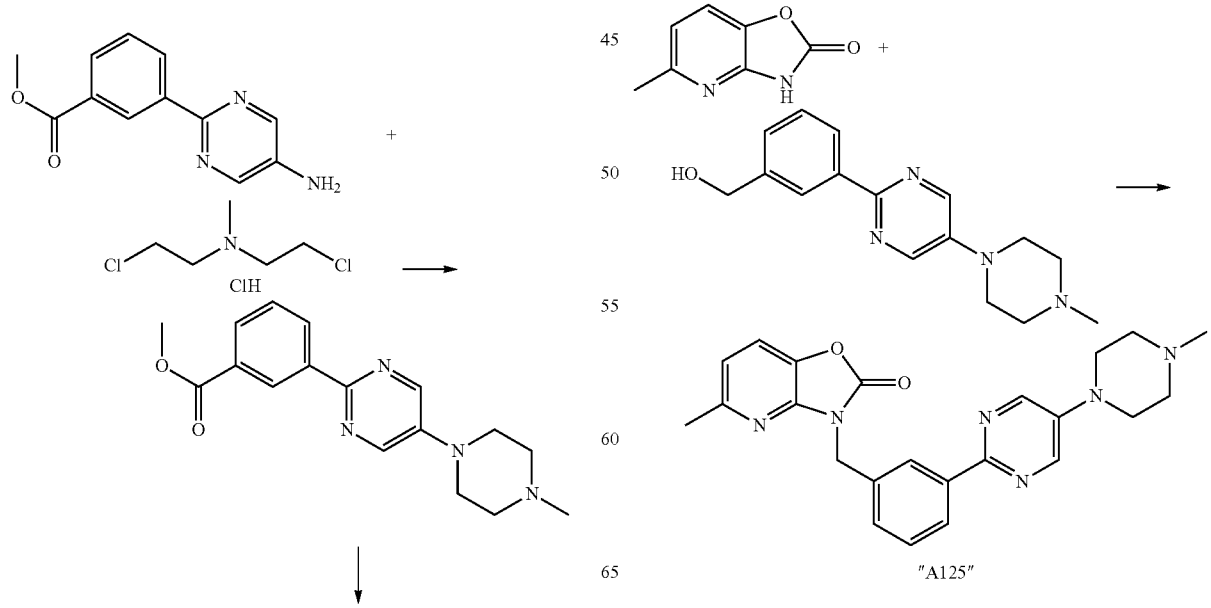

"A125"

67 mg (0.44 mmol) of 5-methyl-3H-oxazolo[4,5-b]pyridin-2-one and 125 mg (0.44 mmol) of {3-[5-(4-methylpiperazin-1-yl)pyrimidin-2-yl]phenyl}methanol are suspended in 5 ml of DMF with 222 mg (0.67 mmol) of polymer-bound triphenylphosphine (about 3 mmol of triphenylphosphine per g), and the mixture is shaken at room temperature for 30 min. 156 mg (0.67 mmol) of di-tert-butyl azodicarboxylate are added. The reaction mixture is shaken at room temperature for 15 h. The reaction mixture is filtered, the residue is evaporated, and the residue is purified by column chromatography on silica gel, giving 67 mg of "A125"; HPLC: Rt=2.20 min (method B); ESI: 418 (M+H);

$^1$H-NMR (DMSO-d$_6$, δ in ppm): 8.58 (2H, s); 8.30 (1H, s); 8.21 (1H, d); 7.65 (1H, d); 7.42-7.49 (2H, m); 7.06 (1H, d); 5.09 (2H, s); 2.48-2.52 (superimposed 8H, m); 2.47 (3H, s); 2.25 (3H, s).

EXAMPLE 14

Preparation of 5-methyl-3-{3-[5-(4-methylpiperazin-1-yl)pyrimidin-2-yl]-benzyl}-3H-oxazolo[4,5-b]pyridin-2-one ("A126")

14.1 Preparation of tert-butyl 4-[2-(3-hydroxymethylphenyl)pyrimidin-5-yl]-piperazine-1-carboxylate 3.2 g (13.95 mmol) of methyl 3-(5-aminopyrimidin-2-yl)benzoate are dissolved in 80 ml of NMP, and 4.73 g (25.96 mmol) of bis(2-chloroethyl)-ammonium chloride and 3.13 g (23.73 mmol) of potassium carbonate are added. The suspension is stirred at 130° C. under an argon atmosphere for 7 days. The reaction mixture is filtered, and the filtrate is stirred into 1 l of diethyl ether. In the process, a residue is deposited as an oil. The organic phase is separated off and discarded.

500 ml of ethyl acetate and 200 ml of saturated sodium hydrogencarbonate solution are added to the residue, the organic phase is separated off, and the aqueous phase is extracted again with 500 ml of ethyl acetate. The organic phases are combined, dried over sodium sulfate and evaporated. The residue is reacted further without further work-up; yield: 2.4 g; HPLC: Rt=2.07 min (method B); ESI: 299 (M+H).

2.4 g (5.4 mmol) of methyl 3-(5-piperazin-1-ylpyrimidin-2-yl)benzoate are dissolved in 15 ml of DMF, 2.98 g (21.6 mmol) of potassium carbonate and 1.5 ml (7.0 mmol) of di-tert-butyl dicarbonate are added, and the mixture is stirred at room temperature for 30 min. The reaction mixture is filtered, and the filtrate is evaporated. The residue is taken up in 200 ml of ethyl acetate and 50 ml of saturated sodium hydrogencarbonate solution. The organic phase is separated off and washed with 50 ml of 1 N HCl, dried over sodium sulfate and evaporated. The product is reacted further without further purification; yield: 1.1 g; HPLC: 3.18 min (method B); ESI: 399 (M+H).

862 mg (2.16 mmol) of tert-butyl 4-[2-(3-methoxycarbonylphenyl)pyrimidin-5-yl]piperazine-1-carboxylate are dissolved in 15 ml of THF, and 10.8 ml (10.8 mmol) of 1 M diisobutylaluminium hydride in THF are added at room temperature. The reaction mixture is stirred at room temperature

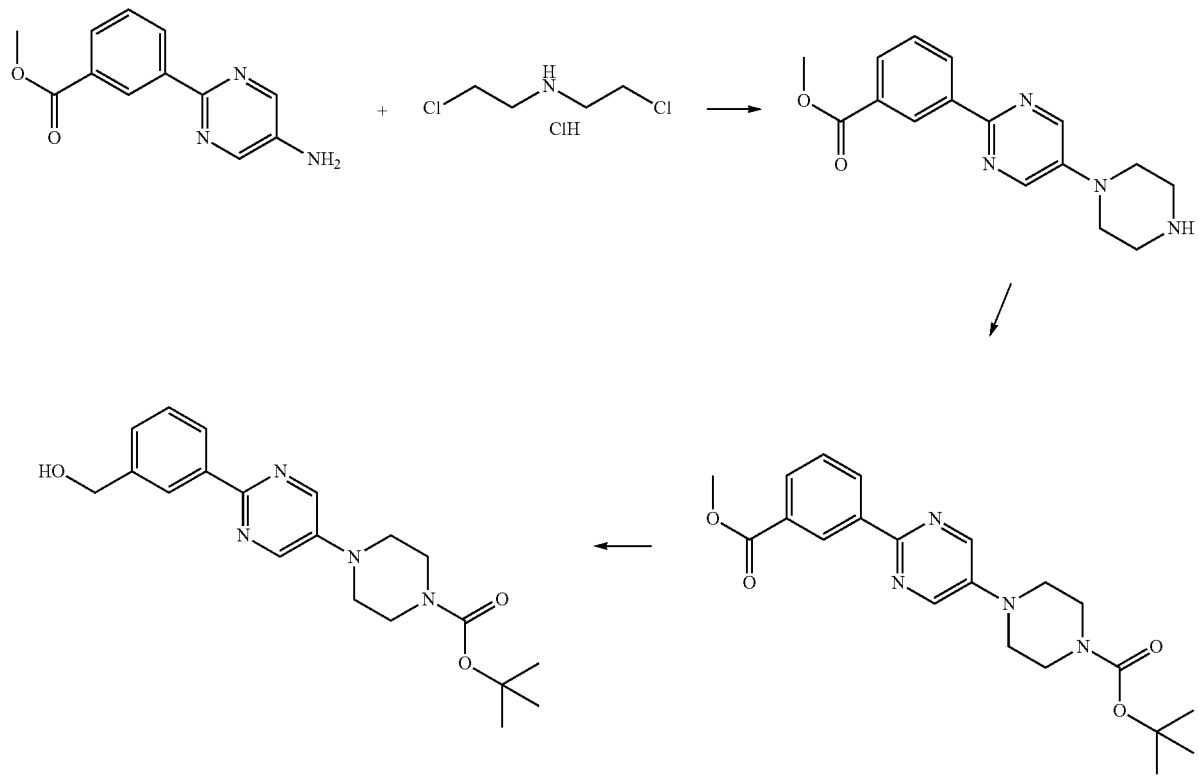 [SMILES: COC(=O)c1cccc(-c2ncc(N)cn2)c1 ; ClCCNCCCl ; Cl ; COC(=O)c1cccc(-c2ncc(N3CCNCC3)cn2)c1 ; CC(C)(C)OC(=O)N1CCN(c2cnc(-c3cccc(CO)c3)nc2)CC1 ; COC(=O)c1cccc(-c2ncc(N3CCN(C(=O)OC(C)(C)C)CC3)cn2)c1]

for 1 h. 3 ml of saturated sodium sulfate solution are added to the reaction mixture with ice cooling. 30 ml of dichloromethane and 5 ml of methanol are added to the gelatinous mixture, which is then stirred for 10 min and filtered through kieselguhr with suction. The filtrate is dried over sodium sulfate and evaporated. The residue is dissolved in dichloromethane and filtered, and the filtrate is evaporated. The product is reacted further without further purification; yield:

677 mg of tert-butyl 4-[2-(3-hydroxymethylphenyl)pyrimidin-5-yl]-piperazine-1-carboxylate; HPLC: 2.66 min (method B); ESI: 371 (M+H).

14.2

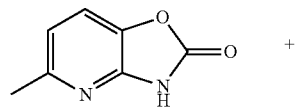
+

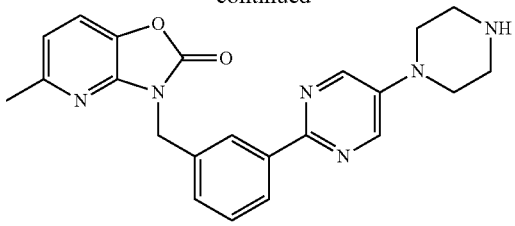
"A126"

Preparation of 5-methyl-3-[3-(5-piperazin-1-ylpyrimidin-2-yl)benzyl]-3H-oxazolo[4,5-b]pyridin-2-one Step a:
67 mg (0.44 mmol) of 5-methyl-3H-oxazolo[4,5-b]pyridin-2-one and 163 mg (0.44 mmol) of tert-butyl 4-[2-(3-hydroxymethylphenyl)pyrimidin-5-yl]piperazine-1-carboxylate are suspended in 5 ml of DMF with 222 mg (0.67 mmol) of polymer-bound triphenylphosphine (about 3 mmol of triphenylphosphine per g), and the mixture is shaken at room temperature for 30 min. 156 mg (0.67 mmol) of di-tert-butyl azodicarboxylate are added. The reaction mixture is shaken at room temperature for 15 h. The reaction mixture is filtered, the residue is evaporated, and the residue is purified by column chromatography on silica gel.
Product: 80 mg; HPLC: Rt=3.10 min (method B); ESI: 503 (M+H), 403 (M-Boc+H).

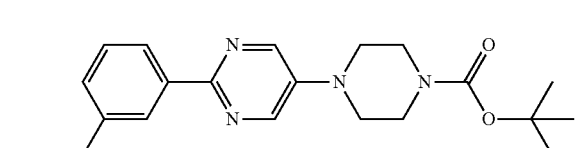

Step b:
80 mg (0.16 mmol) of tart-butyl 4-{2-[3-(5-methyl-2-oxooxazolo[4,5-b]pyridin-3-ylmethyl)phenyl]pyrimidin-5-yl}piperazine-1-carboxylate are dissolved in 6 ml of acetonitrile, and 6 ml of 4 M HCl in dioxane are added. The reaction mixture is stirred at room temperature for 1 h and evaporated. The residue is taken up in water and ethyl acetate, and the water phase is adjusted to pH 12 using NaOH and extracted with ethyl acetate and dichloromethane. The organic phases are combined, dried over sodium sulfate and purified by column chromatography.
Yield: 44 mg of "A126": HPLC: Rt=2.23 min (method B); ESI: 403 (M+H).

The following compounds are obtained analogously:

| No. | Name and/or structure | LCMS retention time [min]/LCMS mass [M + H]+/ m.p. [° C.] |
|---|---|---|
| "A46" | 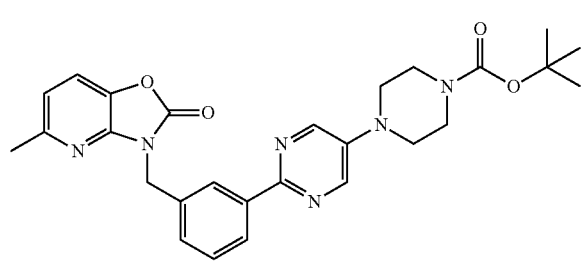 | |

| No. | Name and/or structure | LCMS retention time [min]/LCMS mass [M + H]+/ m.p. [° C.] |
|---|---|---|
| "A47" | 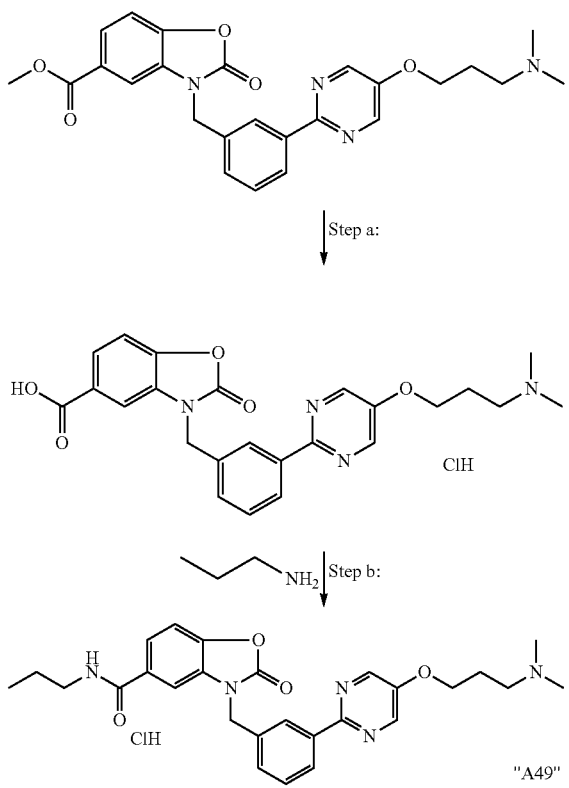 | |
| "A48" | | |

EXAMPLE 15

The preparation of N-propyl-3-{3-[5-(3-dimethylaminopropoxy)pyrimidin-2-yl]benzyl}-2-oxo-2,3-dihydrobenzoxazole-5-carboxamide hydrochloride ("A49") is carried out analogously to the following scheme:

Step a:

Preparation of 3-{3-[5-(3-dimethylaminopropoxy)pyrimidin-2-yl]benzyl}-2-oxo-2,3-dihydrobenzoxazole-5-carboxylic acid hydrochloride 886 mg (1.92 mmol) of 3-{3-[5-(3-dimethylaminopropoxy)pyrimidin-2-yl]-benzyl}-2-oxo-2,3-dihydrobenzoxazole-5-carboxylic acid are suspended in 18 ml of water, and 18 ml of conc. HCl are added. The reaction mixture is stirred at 130° C. for 2 h. The reaction mixture is evaporated to dryness, dried in vacuo and reacted further without further purification;
product: 1.0 g. The product is in the form of the hydrochloride.
ESI: 449 (M+H), Rt=277 min (method C).

Step b:

Preparation of N-propyl-3-{3-[5-(3-dimethylaminopropoxy)pyrimidin-2-yl]-benzyl}-2-oxo-2,3-dihydrobenzoxazole-5-carboxamide hydrochloride 485 mg (1 mmol) of 3-{3-[5-(3-dimethylaminopropoxy)pyrimidin-2-yl]-benzyl}-2-oxo-2,3-dihydrobenzoxazole-5-carboxylic acid hydrochloride are dissolved in 4 ml of DMF, and 387 mg (2 mmol) of EDCI, 139 mg (1 mmol) of HOBt and 516 µl (5 mmol) of N-methylmorpholine are added. 71 mg (1.2 mmol) of propylamine are subsequently added, and the reaction solution is stirred at room temperature for 3 days. The reaction mixture is subsequently added to water and extracted with dichloromethane. The organic phase is dried over sodium sulfate, evaporated to dryness and purified by column chromatography on silica gel. The product is taken up in methanol, ethereal HCl is added, and the mixture is evaporated to dryness, giving 349 mg of "A49" hydrochloride;
ESI 490 (M+H); HPLC: Rt=2.67 min (method C);
$^1$H-NMR (DMSO-$d_6$, δ in ppm): 8.658 (S, 2H), 8.487 (SB, 1H), 8.320 (S, 1H), 8.260 (M, 1H), 7.746 (D, 1H), 7.701 (DD. 1H), 7.520 (D, 2H), 7.465 (D, 1H), 5.197 (S, 2H), 4.309 (T, 2H), 3.210 (M, 4H), 2.782 (D, 6H), 2.211 (M, 2H), 1.517 (M, 2H), 0.867 (T, 3H).

The following compounds are prepared analogously. In some cases, the crude products are purified by preparative HPLC.

| No. | Structure | ESI (M + H) | Rt in min |
|---|---|---|---|
| "A127" | 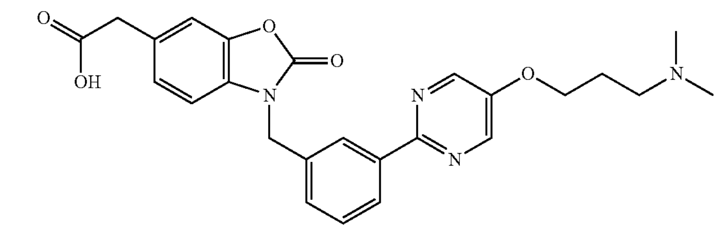 [SMILES: CN(C)CCCOc1cnc(-c2cccc(Cn3c(=O)oc4cc(CC(=O)O)ccc43)c2)nc1] | 463 | 2.21 (method B) |
| "A128" | hydrochloride | 516 | 4.05 (method C) |
| "A129" | hydrochloride | 518 | 3.63 (method C) |
| "A130" | hydrochloride | 502 | 3.89 (method C) |
| "A131" | hydrochloride | 489 | 3.81 (method C) |

-continued

| No. | Structure | ESI (M + H) | Rt in min |
|---|---|---|---|
| "A132" | 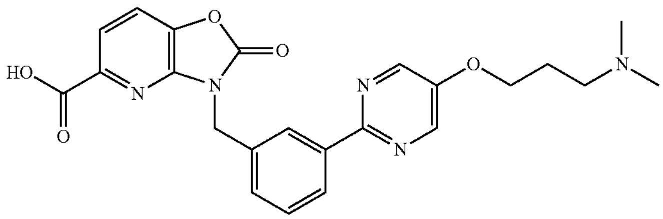 [SMILES: CN(C)CCCOc1cnc(-c2cccc(Cn3c(=O)oc4ccc(C(=O)O)nc43)c2)nc1] | 450 | |
| "A133" | 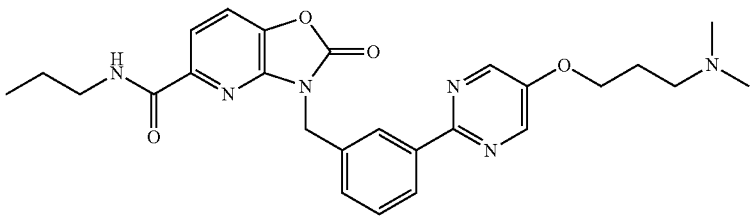 [SMILES: CCCNC(=O)c1ccc2oc(=O)n(Cc3cccc(-c4ncc(OCCCN(C)C)cn4)c3)c2n1] | 491 | |
| "A134" | 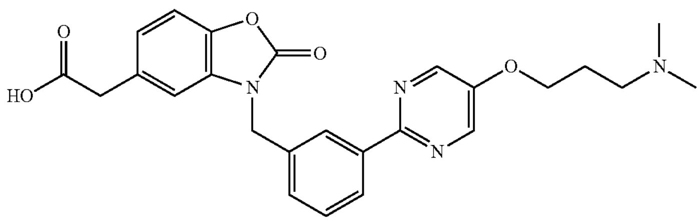 [SMILES: CN(C)CCCOc1cnc(-c2cccc(Cn3c(=O)oc4ccc(CC(=O)O)cc43)c2)nc1] | 463 | |
| "A135" | 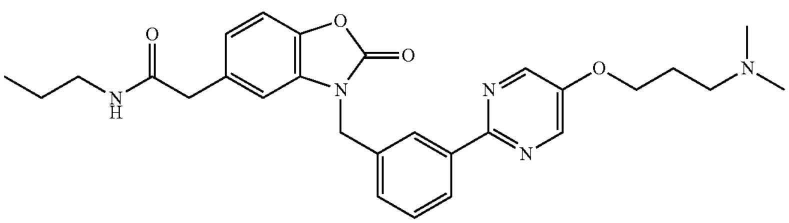 [SMILES: CCCNC(=O)Cc1ccc2oc(=O)n(Cc3cccc(-c4ncc(OCCCN(C)C)cn4)c3)c2c1] | 504 | |
| "A50" | 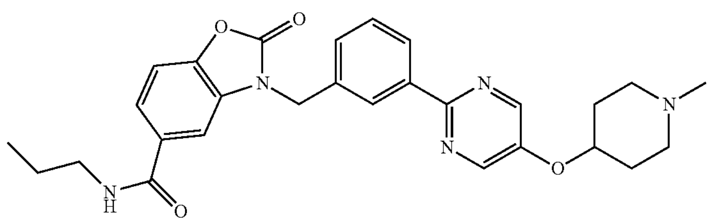 [SMILES: CCCNC(=O)c1ccc2oc(=O)n(Cc3cccc(-c4ncc(OC5CCN(C)CC5)cn4)c3)c2c1] | | |
| "A51" | 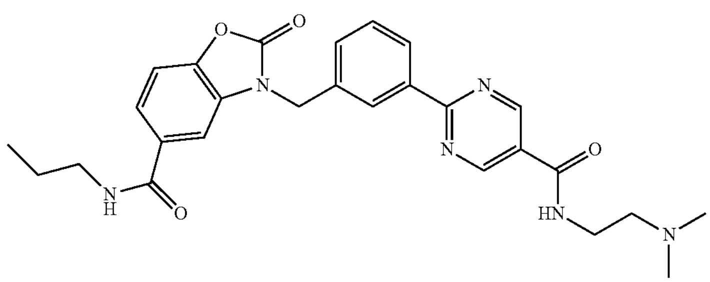 [SMILES: CCCNC(=O)c1ccc2oc(=O)n(Cc3cccc(-c4ncc(C(=O)NCCN(C)C)cn4)c3)c2c1] | | |

| No. | Structure | ESI (M + H) | Rt in min |
|---|---|---|---|
| "A52" | 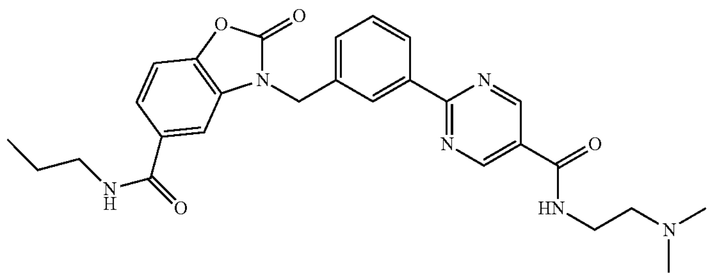 [SMILES: CCCNC(=O)c1ccc2oc(=O)n(Cc3cccc(-c4ncc(C(=O)NCCN(C)C)cn4)c3)c2c1] | | |

EXAMPLE 16

The preparation of 3-{3-[5-(3-dimethylaminopropoxy)pyrimidin-2-yl]benzyl}-6-(1-hydroxyethyl)-3H-benzoxazol-2-one ("A136") is carried out analogously to the following scheme:

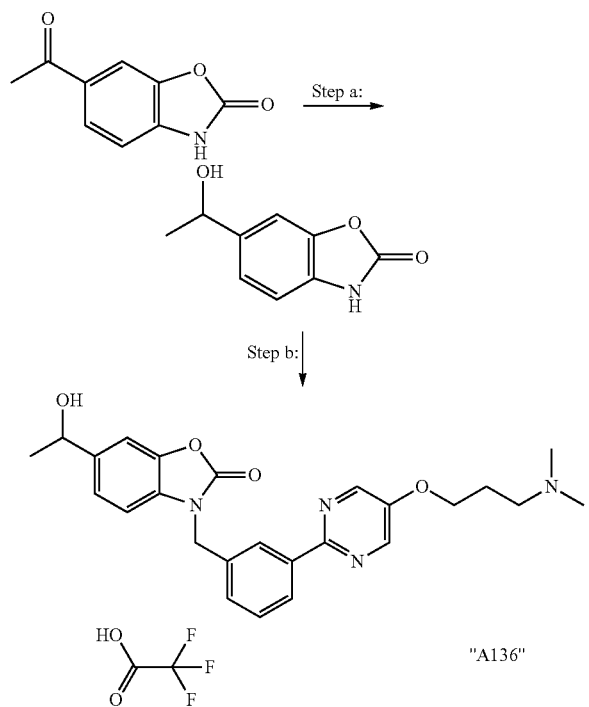

Step a:

Preparation of 6-(1-hydroxyethyl)-3H-benzoxazol-2-one 2.5 g (14.1 mmol) of 6-acetyl-3H-benzoxazol-2-one are dissolved in 150 ml of methanol, and the mixture is stirred for 5 h with 2.5 g of palladium on activated carbon (5%) and under a hydrogen atmosphere. The catalyst is filtered off with suction and rinsed with methanol. The filtrate is evaporated to dryness and dried in vacuo.

Step b:

Preparation of 3-{3-[5-(3-dimethylaminopropoxy) pyrimidin-2-yl]benzyl}-6-(1-hydroxyethyl)-3H-benzoxazol-2-one 94 mg (0.52 mmol) of 6-(1-hydroxyethyl)-3H-benzoxazol-2-one and 261 mg (0.78 mmol) of polymer-bound triphenylphosphine (3 mmol/g) are added to a solution of 150 mg (0.52 mmol) of {3-[5-(3-dimethylaminopropoxy)pyrimidin-2-yl]phenyl}methanol in 6 ml of THF. The suspension is shaken at room temperature for 30 min. 212 mg (0.90 mmol) of di-tert-butyl azodicarboxylate are added to the suspension. After the mixture has been shaken at room temperature for 24 h, a further 261 mg (0.78 mmol) of polymer-bound triphenylphosphine (3 mmol/g) and 212 mg (0.90 mmol) of di-tert-butyl azodicarboxylate are added, and the mixture is shaken at room temperature for a further 24 h. The reaction mixture is filtered, the filtrate is evaporated to dryness, and the residue is purified by preparative HPLC, giving 33 mg of "A136" trifluoroacetate; ESI: 449 (M+H); Rt=2.20 min (method B);

$^1$H-NMR (DMSO-d$_6$, δ in ppm): 9.42 (1H, b); 8.65 (2H, s); 8.30 (1H, b); 8.26 (1H, m); 7.48-7.53 (2H, m); 7.33 (1H, s); 7.15 (2H, d); 5.17 (1H, b); 5.13 (2H, s); 4.72 (1H, m); 4.27 (2H, t); 3.26 (2H, t); 2.83 (6H, s); 2.15 (2H, m); 1.30 (3H, d).

The following compound is prepared analogously:

| No. | Name and/or structure | ESI (M + H) | Rt in min |
|---|---|---|---|
| "A137" | trifluoroacetate | 449 | 2.25 (method B) |

EXAMPLE 17

The preparation of N-[3-(6-chloro-2-oxobenzoxazol-3-yl-methyl)phenyl]-acetamide ("A138") is carried out analogously to the following scheme:

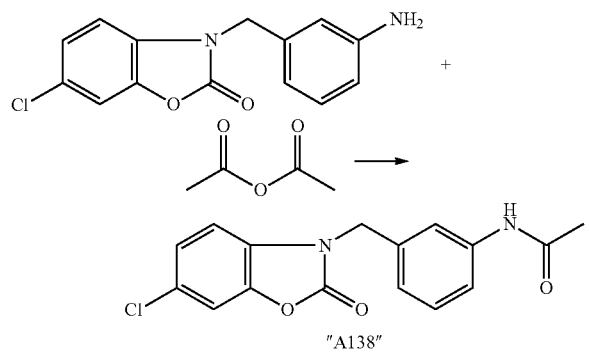

"A138"

300 mg (1.09 mmol) of 3-(3-aminobenzyl)-6-chloro-3H-benzoxazol-2-one are dissolved in 3 ml of tetrahydrofuran, 134 µl (1.42 mmol) of acetic anhydride and 303 µl (2.18 mmol) of triethylamine are added, and the mixture is left to stand at room temperature for 2 h, during which a precipitate forms. The reaction mixture is diluted with water, and the precipitate is filtered off with suction and washed with water. The residue is triturated with ether, filtered off with suction and dried, giving 272 mg of "A138"; m.p. 209-210° C.; ESI: 317 (M+H); HPLC: Rt=4.43 min (method C);

¹H-NMR (DMSO-d₆, δ in ppm): 9.920 (SB, 1H), 7.573 (M, 2H), 7.483 (SB, 1H), 7.272 (M, 2H), 7.173 (D, 1H), 7.051 (D, 1H), 5.015 (S, 2H), 2.001 (S, 3H).

EXAMPLE 18

The preparation of 1-[3-(6-chloro-2-oxobenzoxazol-3-yl-methyl)phenyl]-3-[3-(4-methylpiperazin-1-yl)propyl]urea ("A139") is carried out analogously to the following scheme:

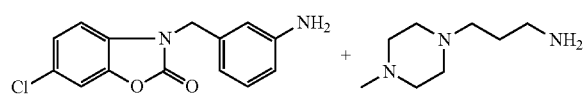

↓

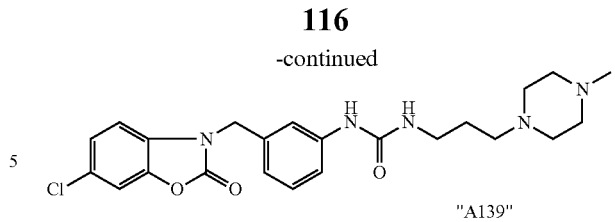

"A139"

300 mg (1.09 mmol) of 3-(3-aminobenzyl)-6-chloro-3H-benzoxazol-2-one are dissolved in 6 ml of acetonitrile, 227 mg (1.09 mmol) of 4-nitrophenyl chloroformate and 88 µl (1.09 mmol) of pyridine are added, and the mixture is stirred at room temperature for 40 minutes. 381 mg (2.73 mmol) of potassium carbonate and 174 µl (1.64 mmol) of 1-(3-aminopropyl)-4-methylpiperazine are subsequently added, and the mixture is stirred at 70° C. for 24 h. The reaction mixture is poured into 50 ml of water and extracted with 3×100 ml of dichloromethane, and the combined dichloromethane phases are dried over sodium sulfate and evaporated to dryness. The crude product is purified by column chromatography on silica gel. The product is dissolved in methanol, ethereal hydrochloric acid is added, and the mixture is evaporated to dryness. The salt is crystallised from methanol/ether, filtered off with suction and dried, giving 256 mg of "A139" dihydrochloride; m.p. 246° C.; ESI: 458 (M+H); HPLC: Rt=2.80 min (method C), ¹H-NMR (DMSO-d₆, δ in ppm): 8.868 (SB, 1H), 7.594 (D, 1H), 7.361 (M, 2H), 7.265 (M, 1H), 7.188 (M, 2H), 6.906 (D, 1H), 6.499 (SB, 1H), 4.981 (S, 2H), 3.888-3.218 (M, 6H), 3.153 (D, 4H), 2.821 (SB, 3H), 1.857 (SB, 2H).

The following compound is prepared analogously:

| No. | Name and/or structure | ESI (M + H) | Rt in min |
|---|---|---|---|
| "A140" | 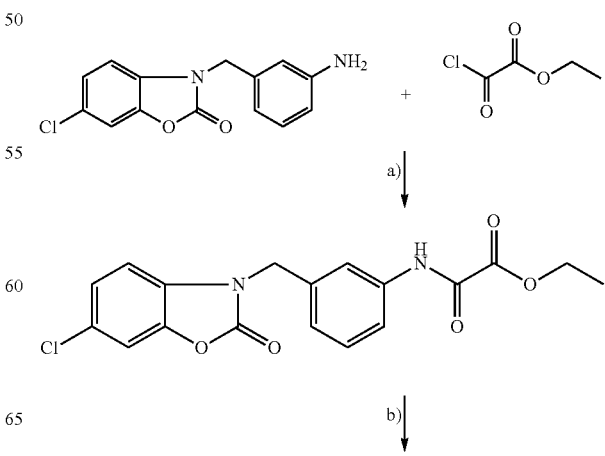 trifluoroacetate | 403 | 2.91 (method C) m.p. 182° C. |

EXAMPLE 19

The preparation of N-[3-(6-chloro-2-oxobenzoxazol-3-yl-methyl)phenyl]-N'-(2-dimethylaminoethyl)oxalamide ("A141") is carried out analogously to the following scheme:

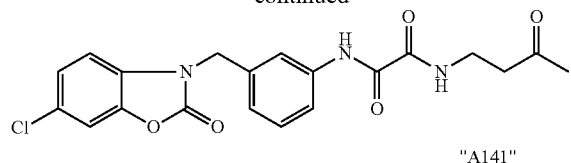

"A141"

Step a:

Preparation of ethyl N-[3-(6-chloro-2-oxobenzoxazol-3-ylmethyl)phenyl]-oxalaminate 300 mg (1.09 mmol) of 3-(3-aminobenzyl)-6-chloro-3H-benzoxazol-2-one are suspended in 3 ml of dichloromethane and 115 μl (1.42 mmol) of pyridine. 124 μl (1.09 mmol) of ethyl chloroformyl formate are subsequently added, and the mixture is stirred at room temperature for 30 minutes, during which a clear solution forms. The mixture is diluted with dichloromethane, washed with 1 N hydrochloric acid and then with water, dried over sodium sulfate and evaporated to dryness. The product is reacted further directly without further purification; product: 408 mg; ESI: 375 (M+H); HPLC: 4.32 min (method C).

Step b:

Preparation of N-[3-(6-chloro-2-oxobenzoxazol-3-ylmethyl)phenyl]-N'-(2-dimethylaminoethyl)oxalamide 408 mg (1.09 mmol) of ethyl N-[3-(6-chloro-2-oxobenzoxazol-3-ylmethyl)-phenyl]oxalaminate are suspended in 20 ml of ethanol, 133 μl (1.20 mmol) of N,N-dimethylethylenediamine are added, and the mixture is stirred at room temperature for 48 h. The precipitate is filtered off with suction, washed with ethanol and then with ether and dried. The crude product is suspended in methanol, and ethereal hydrochloric acid is added, during which a virtually clear solution forms briefly, from which the salt immediately crystallises out again. The precipitate is filtered off with suction, washed with a little methanol and then with ether and dried, giving 292 mg of "A141" hydrochloride; m.p. 273° C.; ESI 417 (M+H); HPLC: Rt=3.09 min (method C);

$^1$H-NMR (DMSO-$d_6$, δ in ppm): 10.667 (S, 1H), 9.990 (SB, 1H), 7.797 (M, 2H), 7.617 (D, 1H), 7.373 (T, 1H), 7.266 (M, 1H), 7.196 (M, 2H), 5.061 (S, 2H), 3.557 (M, 2H), 3.233 (T, 2H), 2.798 (S, 6H).

EXAMPLE 20

The preparation of N-(4-dimethylaminobutyl)-2-[3-(5-methyl-2-oxooxazolo-[4,5-b]pyridin-3-ylmethyl)phenyl]pyrimidine-5-carboxamide ("A142") is carried out analogously to the following scheme:

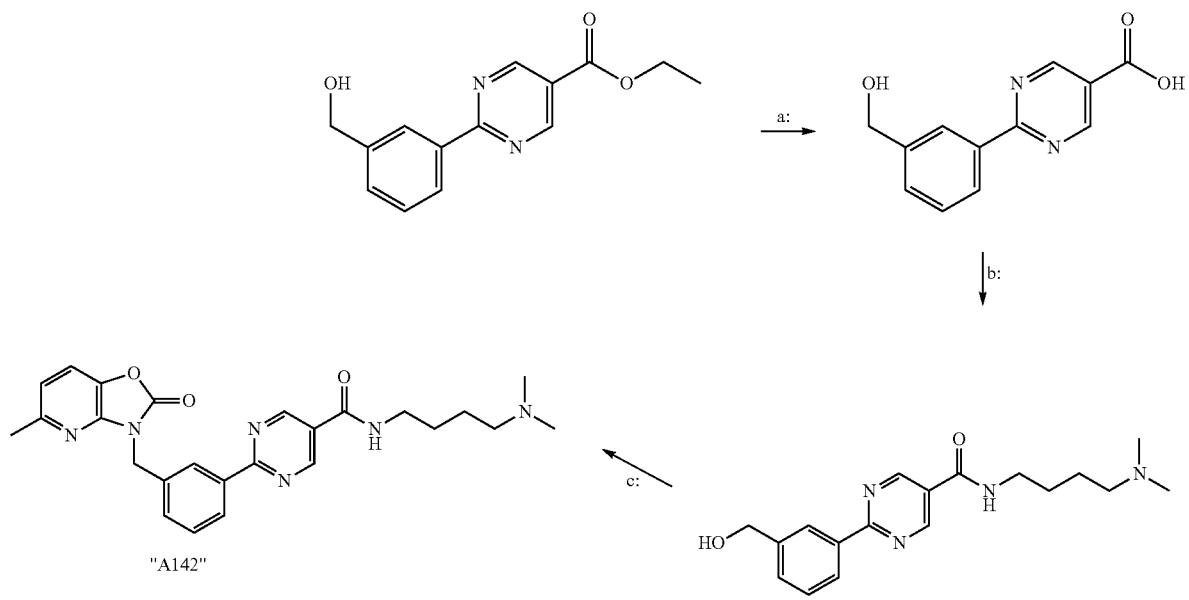

"A142"

Step a:

1 g (3.88 mmol) of ethyl 2-(3-hydroxymethylphenyl)pyrimidine-5-carboxylate is dissolved in 40 ml of THF and 4 ml of water, and 372 mg (15.5 mmol) of lithium hydroxide are added. The reaction mixture is refluxed for 4 h. The THF is subsequently removed by distillation, the solution is adjusted to pH 5 using 1 N HCl, and the solid is filtered off with suction, dried in vacuo and reacted further directly without further purification. ESI: 231 (M+H); Rt=1.98 min (method B).

Step b:

1.4 g (6.08 mmol) of 2-(3-hydroxymethylphenyl)pyrimidine-5-carboxylic acid are dissolved in 8 ml of THF and 2 ml of DMF, and 1.36 ml (12.2 mmol) of 4-methylmorpholine, 1.77 g (9.12 mmol) of EDCI and 1.10 g (7.91 mmol) of HOBt are added. 919 mg (7.91 mmol) of N,N-di-methylaminobutylamine are added, and the reaction mixture is stirred at room temperature for 18 h. The reaction solution is evaporated, the residue is taken up in ethyl acetate, and the mixture is washed with 1 N NaOH and saturated NaCl solution. The organic phase is dried over sodium sulfate and evaporated. The crude product is reacted further without further purification.

ESI: 329; HPLC: Rt=1.81 min (method B).

Step c:

Reaction of the starting materials in a Mitsunobu reaction as described above, giving "A142"; ESI: 461 (M+H); Rt=2.32 min (method B);

$^1$H-NMR (DMSO-$d_6$, δ in ppm): 9.24 (2H, s); 8.81 (1H, t); 8.51 (1H, s); 8.38 (1H, d); 7.66 (1H, d); 7.54-7.61 (2H, m); 7.06 (1H, d); 5.14 (2H, s); 2.51 (superimposed, 6H, b); 2.48 (3H, s); 2.23 (2H, t); 1.57 (2H, m); 1.47 (2H, m).

EXAMPLE 21

The preparation of 5-methyl-3-[3-(3-methyl-6-oxo-6H-pyridazin-1-yl)-benzyl]-3H-oxazolo[4,5-b]pyridin-2-one ("A143") is carried out analogously to the following scheme:

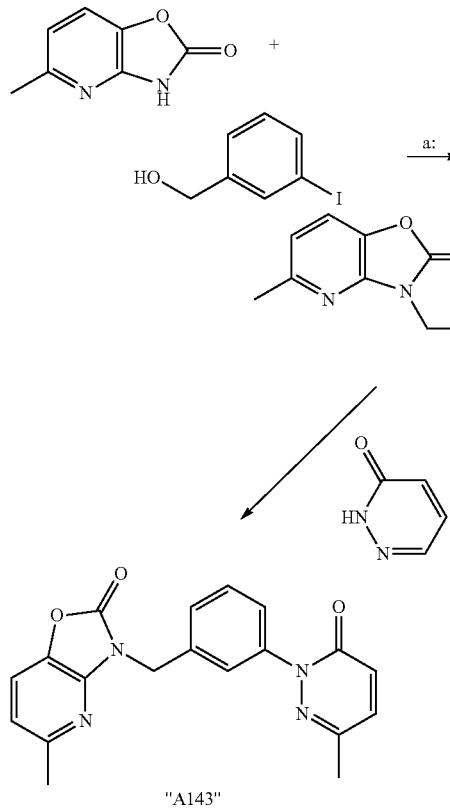

Step a:

Reaction of 5-methyl-3H-oxazolo[4,5-b]pyridin-2-one with (3-iodophenyl)-methanol under Mitsunobu conditions gives 3-(3-iodobenzyl)-5-methyl-3H-oxazolo[4,5-b]pyridin-2-one; ESI: 367 (M+H).

Step b:

14.3 mg (0.08 mmol) of copper(I) iodide, 76 mg (0.55 mmol) of potassium carbonate and 11 mg (0.08 mmol) of 8-hydroxyquinoline are added to a solution of 184 mg (0.50 mmol) of 3-(3-iodobenzyl)-5-methyl-3H-oxazolo-[4,5-b]pyridin-2-one and 55.1 mg (0.5 mmol) of 6-methylpyridazin-3(2H)-one in 2 ml of DMF, and the mixture is heated at 120° C. for 24 hours. The reaction mixture is allowed to cool, and 10% aqueous ammonia solution and ethyl acetate are added. The resultant precipitate is filtered off with suction, washed with water and dried. The residue is boiled in ethyl acetate, filtered off with suction and washed with ethyl acetate. The residue is dried in vacuo, giving "A143", ESI 349 (M+H),

EXAMPLE 22

The preparation of 5-methyl-3-[3-(5-methylpyridin-2-yl)benzyl]-3H-oxazolo[4,5-b]pyridin-2-one ("A144") is carried out analogously to the following scheme:

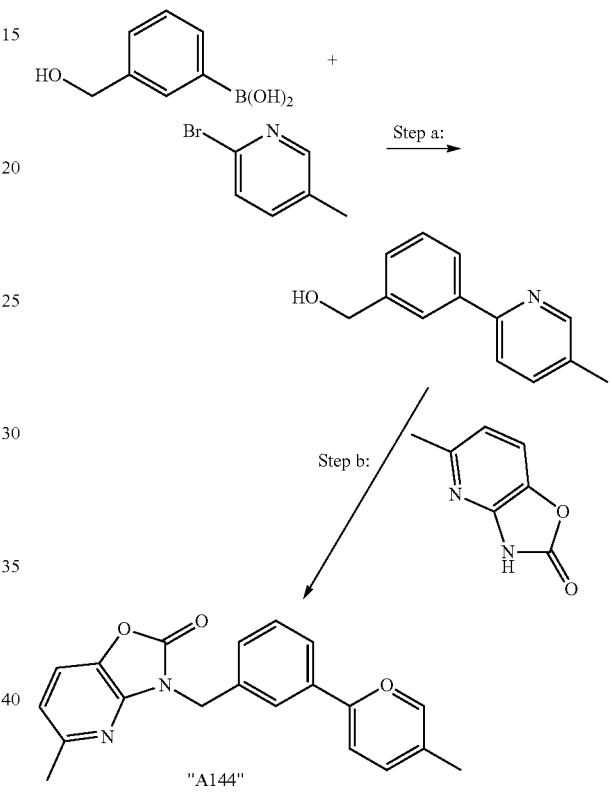

Step a:

92 mg (0.03 mmol) of tetrakis(triphenylphosphine)palladium are added to a suspension, kept under nitrogen, of 849 mg (4.0 mmol) of tripotassium phosphate, 344 mg (2.0 mmol) of 2-bromo-5-methylpyridine and 304 mg (2.0 mmol) of 3-hydroxymethylbenzeneboronic acid in 12 ml of dioxane and 1 ml of water, and the mixture is heated at the boil with stirring for 18 hours. The reaction mixture is cooled to room temperature and partitioned between water and ethyl acetate. The organic phase is dried over sodium sulfate and evaporated, and the residue is chromatographed on a silica-gel column with dichloromethane/methanol as eluent: [3-(5-methylpyridin-2-yl)phenyl]methanol as yellowish oil; ESI 200.

Step b:

Reaction of [3-(5-methylpyridin-2-yl)phenyl]methanol with 5-methyl-3H-oxazolo[4,5-b]pyridin-2-one under Mitsunobu conditions gives the desired 5-methyl-3-[3-(5-methylpyridin-2-yl)benzyl]-3H-oxazolo[4,5-b]-pyridin-2-one, ESI 332 (M+H).

121
5-Methyl-3-(3-pyrimidin-5-ylbenzyl)-3H-oxazolo[4,5-b]pyridin-2-one ("A145") is prepared analogously:
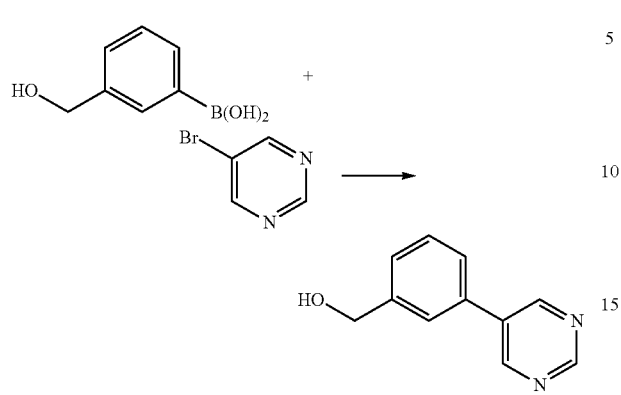
122
-continued
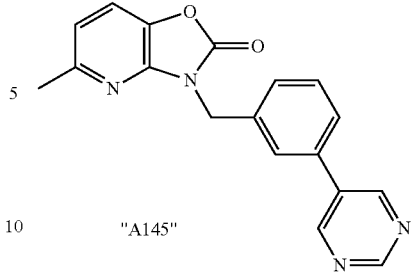
"A145"
EXAMPLE 23
The preparation of 5-methyl-3-[3-(4-piperazin-1-ylpyrimidin-2-yl)benzyl]-3H-oxazolo[4,5-b]pyridin-2-one ("A146") is carried out analogously to the following scheme:
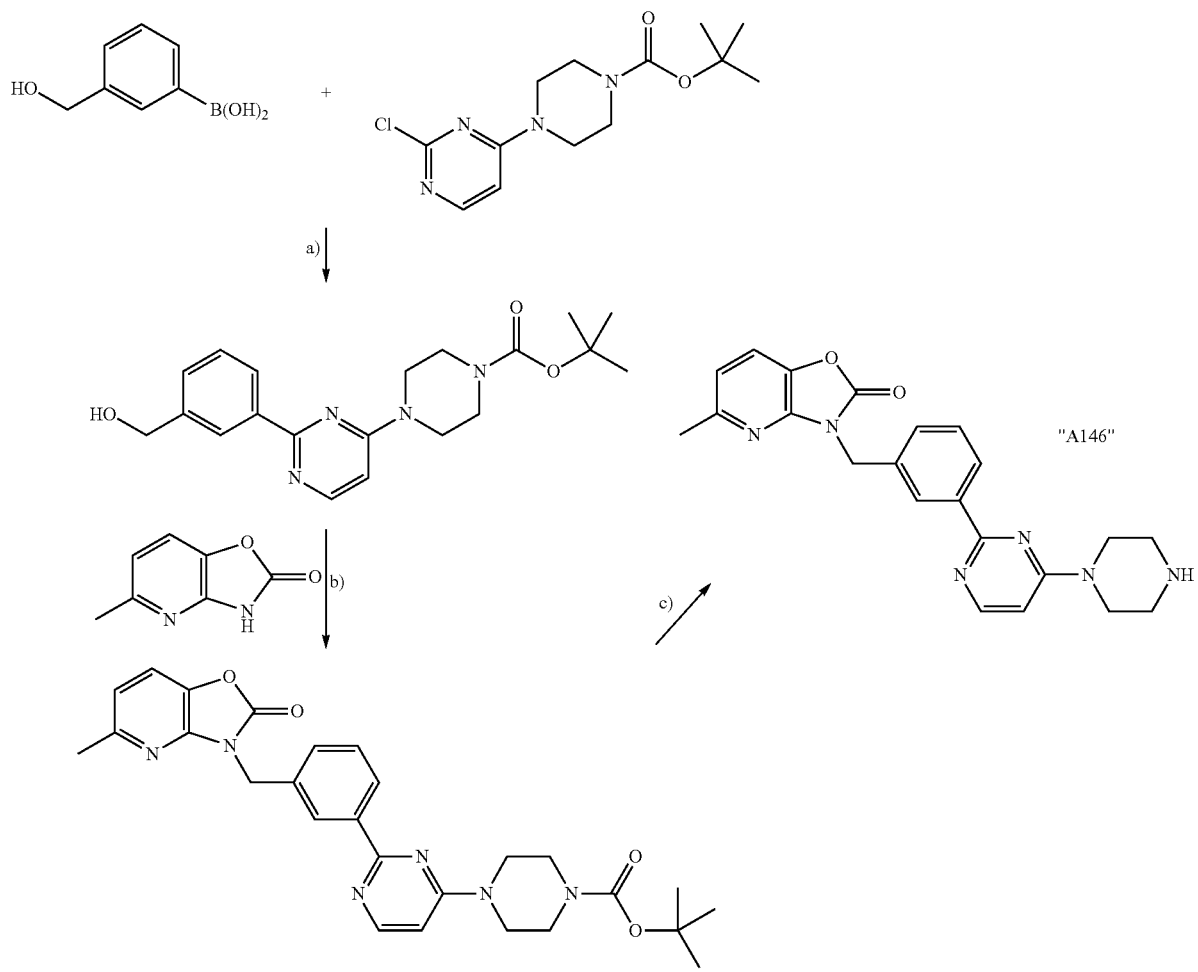

Step a:

A catalyst solution prepared by reaction of 56 mg (0.08 mmol) of bis(triphenylphosphine)palladium(II) chloride and 3.0 mg (0.08 mmol) of sodium borohydride in 0.4 ml of THF at 55° C. is added to a suspension, kept under nitrogen, of 849 mg (4.0 mmol) of tripotassium phosphate, 598 mg (2.0 mmol) of tert-butyl 4-(2-chloropyrimidin-4-yl)piperazine-1-carboxylate (prepared as described in WO 03/104225) and 304 mg (2.0 mmol) of 3-hydroxymethylbenzeneboronic acid in 12 ml of dioxane and 1 ml of water. The reaction mixture is stirred at 97° C. for 18 hours. The reaction mixture is cooled and partitioned between water and ethyl acetate. The organic phase is dried over sodium sulfate and evaporated, and the residue is chromatographed on a silica-gel column with dichloromethane/methanol as eluent: tert-butyl 4-[2-(3-hydroxymethylphenyl)pyrimidin-4-yl]piperazine-1-carboxylate as yellowish solid; ESI 371.

Step b:

118 mg (0.582 mmol) of diisopropyl azodicarboxylate are added to a solution of 144 mg (0.388 mmol) of tert-butyl 4-[2-(3-hydroxymethylphenyl)pyrimidin-4-yl]piperazine-1-carboxylate, 87 mg (0.582 mmol) of 5-methyl-3H-oxazolo-[4,5-b]pyridin-2-one and 153 mg (0.582 mmol) of triphenylphosphine in 3 ml of THF. The reaction mixture is stirred at room temperature for 18 hours. The mixture is evaporated, and the residue is chromatographed on a silica-gel column with dichloromethane/methanol as eluent; ESI 503 (M+H).

Step c:

1.3 ml of 4 N HCl in dioxane are added to a solution of 70 mg (0.14 mmol) of tert-butyl 4-{2-[3-(5-methyl-2-oxoox-azolo[4,5-b]pyridin-3-ylmethyl)phenyl]-pyrimidin-4-yl}piperazine-1-carboxylate in 1 ml of dioxane, and the mixture is left at room temperature for 18 hours. The reaction mixture is partitioned between water and ethyl acetate. The aqueous phase is adjusted to a pH of 14 using 1 N NaOH and extracted with ethyl acetate. The organic phase is dried over sodium sulfate and evaporated, giving "A146" as the hydrochloride; ESI 403 (M+H).

EXAMPLE 24

The preparation of 5-methyl-3-{3-[5-(1-methyl-1H-pyrazol-4-yl)pyrimidin-2-yl]benzyl}-3H-oxazolo[4,5-b]pyridin-2-one ("A147") is carried out analogously to the following scheme:

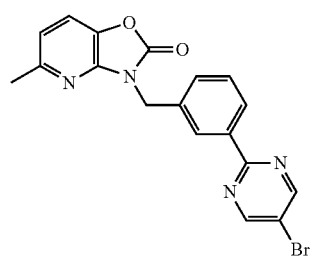
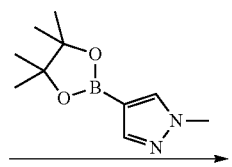

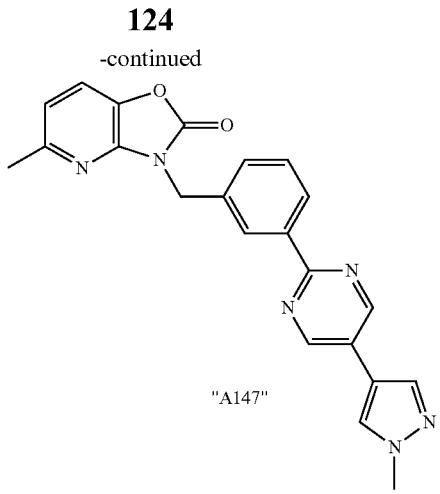

"A147"

425 mg (2.0 mmol) of tripotassium phosphate trihydrate and 56.2 mg (0.08 mmol) of bis(triphenylphosphine)palladium chloride are added to a solution, kept under nitrogen, of 397 mg (1.00 mmol) of 3-[3-(5-bromopyrimidin-2-yl)benzyl]-5-methyl-3H-oxazolo[4,5-b]pyridin-2-one and 229 mg (1.10 mmol) of 1-methyl-4-(4,4,5,5-tetramethyl-1,3,2-dioxaborolan-2-yl)-1H-pyrazole in 10 ml of 1,2-dimethoxyethane, and the mixture is stirred at 80° C. for 18 hours, during which a grey precipitate forms. The reaction mixture is diluted with water and filtered. The residue is chromatographed on a silica-gel column with dichloromethane/methanol as eluent, giving "A147", ESI; 399 (M+H).

EXAMPLE 25

The preparation of 3-{3-[5-(3-dimethylaminopropoxy)pyrimidin-2-yl]-benzyl}-5-(1-methyl-1H-pyrazol-4-yl)-3H-oxazolo[4,5-b]pyridin-2-one ("A148") is carried out analogously to the following scheme:

125
-continued

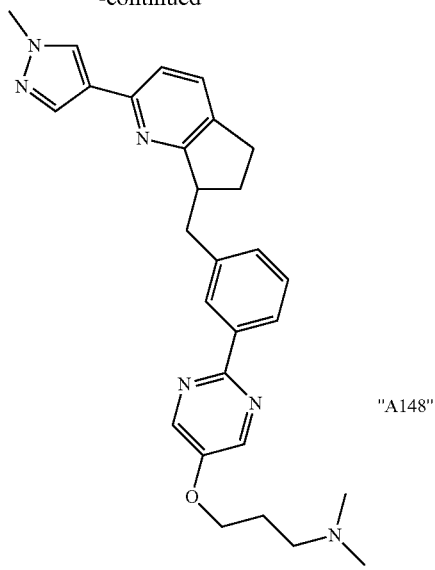

"A148"

425 mg (2.0 mmol) of tripotassium phosphate trihydrate and 56.2 mg (0.08 mmol) of bis(triphenylphosphine)palladium chloride are added to a solution, kept under nitrogen, of 484 mg (1.00 mmol) of 5-bromo-3-{3-[5-(3-dimethylaminopropoxy)pyrimidin-2-yl]benzyl}-3H-oxazolo[4,5-b]pyridin-2-one and 229 mg (1.10 mmol) of 1-methyl-4-(4,4,5,5-tetramethyl-1,3,2-dioxaborolan-2-yl)-1H-pyrazole in 10 ml of 1,2-dimethoxyethane, and the mixture is stirred at 80° C. for 18 hours. The reaction mixture is diluted with water and filtered. The residue is chromatographed on a silica-gel column with dichloromethane/methanol as eluent, giving "A148", ESI: 486 (M+H).

Pharmacological Data
Met Kinase Inhibition

TABLE 1

| Compound No. | $IC_{50}$ (cell assay) |
|---|---|
| "A1" | A |
| "A2" | A |
| "A3" | A |
| "A4" | A |
| "A5" | A |
| "A6" | A |
| "A7" | A |
| "A8" | A |
| "A9" | A |
| "A10" | A |
| "A11" | A |
| "A12" | A |
| "A13" | A |
| "A14" | A |
| "A15" | A |
| "A16" | A |
| "A17" | A |
| "A18" | A |
| "A19" | A |
| "A20" | A |
| "A21" | A |
| "A22" | A |
| "A30" | A |
| "A31" | A |
| "A32" | A |
| "A33" | A |
| "A34" | A |
| "A35" | A |

TABLE 1-continued

| Compound No. | $IC_{50}$ (cell assay) |
|---|---|
| "A36" | A |
| "A37" | A |
| "A64" | A |
| "A66" | A |
| "A67" | A |
| "A76" | A |
| "A79" | A |
| "A82" | A |
| "A87" | A |
| "A92" | B |
| "A93" | B |
| "A95" | B |
| "A96" | A |
| "A103" | B |

$IC_{50}$:
10 nM-1 μM = A
1 μM-10 μM = B
>10 mM = C

The following examples relate to medicaments:

EXAMPLE A

Injection Vials

A solution of 100 g of an active ingredient of the formula I and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of an active ingredient of the formula I with 100 g of soya lecithin and 1400 g of cocoa butter is melted, poured into moulds and allowed to cool. Each suppository contains 20 mg of active ingredient.

EXAMPLE C

Solution

A solution is prepared from 1 g of an active ingredient of the formula I, 9.38 g of $NaH_2PO_4.2H_2O$, 28.48 g of $Na_2HPO_4.12H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active ingredient of the formula I are mixed with 99.5 g of Vaseline under aseptic conditions.

EXAMPLE E

Tablets

A mixture of 1 kg of active ingredient of the formula I, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

EXAMPLE F

Dragees

Tablets are pressed analogously to Example E and subsequently coated in a conventional manner with a coating of sucrose, potato starch, talc, tragacanth and dye.

EXAMPLE C

Capsules 2 kg of active ingredient of the formula I are introduced into hard gelatine capsules in a conventional manner in such a way that each capsule contains 20 mg of the active ingredient.

EXAMPLE H

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

The invention claimed is:
1. A method for the treatment of a disease facilitated by Met kinase signal transduction in a patient, wherein the disease is a solid tumor or a tumor of the blood and/or immune system, comprising administering to the patient a compound which inhibits signal transduction by Met kinase in the patient selected from the following compounds:

| No. | Structure and/or name |
|---|---|
| "A1" | 3-(4-Methylpiperazin-1-yl)propyl [3-(5-methoxy-2-oxobenzoxazol-3-ylmethyl)phenyl]carbamate |

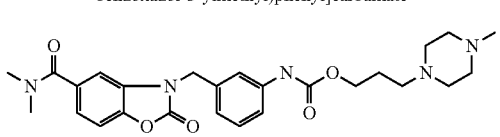

| "B1" | 3-(4-Methylpiperazin-1-yl)propyl [3-(5-methyl-2-oxooxazolo]4,5-b]pyridin-3-ylmethyl)phenyl]carbamate |
| "A2" | 3-(4-Methylpiperazin-1-yl)propyl [3-(5-chloro-2-oxobenzoxazol-3-ylmethyl)phenyl]carbamate |

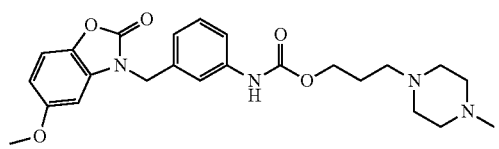

| "A3" | 3-(4-Methylpiperazin-1-yl)propyl [3-(5-dimethylcarbamoyl-2-oxobenzoxazol-3-ylmethyl)phenyl]carbamate |

| No. | Structure and/or name |
|---|---|
| "A4" | 3-Piperazin-1-ylpropyl [3-(5-dimethylcarbamoyl-2-oxobenzoxazol-3-ylmethyl)phenyl]carbamate |
| "A5" | 3-(4-Methylpiperazin-1-yl)propyl [3-(5-propylcarbamoyl-2-oxobenzoxazol-3-ylmethyl)phenyl]carbamate |
| "A6" | 3-(4-Methylpiperazin-1-yl)propyl [3-(6-chloro-2-oxobenzoxazol-3-ylmethyl)phenyl]carbamate |
| "A7" | 3-(4-Methylpiperazin-1-yl)propyl [3-(5-methyl-2-oxobenzoxazol-3-ylmethyl)phenyl]carbamate |
| "A8" | 3-(4-Methylpiperazin-1-yl)propyl [3-(5-acetyl-2-oxobenzoxazol-3-ylmethyl)phenyl]carbamate |
| "A9" | 3-(4-Methylpiperazin-1-yl)propyl {3-[6-(1-hydroxyethyl)-2-oxobenzoxazol-3-ylmethyl]phenyl}carbamate |

[Structure of A9]

| "A10" | 3-Piperazin-1-ylpropyl [3-(5-propylcarbamoyl-2-oxobenzoxazol-3-ylmethyl)phenyl]carbamate |
| "A11" | 3-Dimethylaminopropyl [3-(2-oxooxazolo [4,5-b]pyridin-3-ylmethyl)phenyl]carbamate |

[Structure of A11]

| "A12" | 3-Dimethylaminopropyl [3-(5-dimethylcarbamoyl-2-oxobenzoxazol-3-ylmethyl)phenyl]carbamate |
| "A13" | 3-Dimethylaminopropyl [3-(5-propylcarbamoyl-2-oxobenzoxazol-3-ylmethyl)phenyl]carbamate |
| "A14" | 3-Dimethylaminopropyl [3-(6-methoxycarbonyl-2-oxobenzoxazol-3-ylmethyl)phenyl]carbamate |
| "A15" | 3-Dimethylaminopropyl [3-(5-methoxycarbonyl-2-oxobenzoxazol-3-ylmethyl)phenyl]carbamate |
| "A16" | 3-Dimethylaminopropyl [3-(2-oxobenzoxazol-3-ylmethyl)phenyl]carbamate |
| "A17" | 2-(4-Methylpiperazin-1-yl)ethyl [3-(2-oxobenzoxazol-3-ylmethyl)phenyl]carbamate |

[Structure of A17]

| "A18" | 3-(4-Methylpiperazin-1-yl)propyl [3-(2-oxobenzoxazol-3-ylmethyl)phenyl]carbamate |
| "A19" | 3-(4-Methylpiperazin-1-yl)propyl [3-(5,6-difluoro-2-oxobenzoxazol-3-ylmethyl)phenyl]carbamate |
| "A20" | 3-(4-Methylpiperazin-1-yl)propyl [3-(6-methyl-2-oxobenzoxazol-3-ylmethyl)phenyl]carbamate |
| "A21" | 3-(4-Methylpiperazin-1-yl)propyl [3-(6-methyl-2-oxobenzoxazol-3-ylmethyl)phenyl]carbamate |
| "A22" | 3-(4-Methylpiperazin-1-yl)propyl [3-(6-acetyl-2-oxobenzoxazol-3-ylmethyl)phenyl]carbamate |
| "A23" | Ethyl {3-[5-(4-methylpiperazin-1-yl)-2-oxobenzoxazol-3-yl]methyl]phenyl}carbamate |
| "A24" | 3-(4-Methylpiperazin-1-yl)propyl [3-(5-cyano-2-oxobenzoxazol-3-ylmethyl)phenyl]carbamate |
| "A25" | 3-(4-Methylpiperazin-1-yl)propyl [3-(5-ethylsulfonyl-2-oxobenzoxazol-3-ylmethyl)phenyl]carbamate |

[Structure of A23]

| No. | Structure and/or name |
|---|---|
| "A26" | 3-(4-Methylpiperazin-1-yl)propyl {3-[1-(5,6-difluoro-2-oxo-benzoxazol-3-yl)ethyl]phenyl}carbamate |
| "A27" | 2-(4-Methylpiperazin-1-yl)propyl {3-[1-(5,6-difluoro-2-oxo-benzoxazol-3-yl)ethyl]phenyl}carbamate |
| "A28" | 3-(4-Methylpiperazin-1-yl)propyl {3-[5-(1-hydroxyethyl)-2-oxo-benzoxazol-3-ylmethyl]phenyl}carbamate |
| "A28a" | |
| "A28b" | |
| "A29" | Ethyl {3-[6-(2-dimethylaminoethylcarbamoyl)-2-oxobenzoxazol-3-ylmethyl]phenyl}carbamate |
| "A30" | Ethyl {3-[5-(2-dimethylaminoethylcarbamoyl)-2-oxobenzoxazol-3-ylmethyl]phenyl}carbamate |
| "A31" | Ethyl {3-[5-(3-dimethylaminopropylcarbamoyl)-2-oxobenzoxazol-3-ylmethyl]phenyl}carbamate |
| "A32" | Ethyl (3-{1-[5-(4-dimethylaminobutylcarbamoyl)-2-oxobenzoxazol-3-yl]ethyl}phenyl)carbamate |
| "A33" | Ethyl (3-{1-[5-(2-dimethylaminoethylcarbamoyl)-2-oxobenzoxazol-3-yl]ethyl}phenyl)carbamate |
| "A34" | N-(4-Dimethylaminobutyl)-2-oxo-3-(2-oxo-2,3-dihydro-1H-benzimidazol-5-ylmethyl)-2,3-dihydrobenzoxazole-5-carboxamide |
| "A35" | N-(2-Dimethylaminoethyl)-2-oxo-3-(2-oxo-2,3-dihydro-1H-benzimidazol-5-ylmethyl)-2,3-dihydrobenzoxazole-5-carboxamide |
| "A36" | Ethyl (3-{1-[5-(3-dimethylaminopropylcarbamoyl)-2-oxo benzoxazol-3-yl]ethyl}phenyl)carbamate |
| "A37" | Methyl 3-(3-ethoxycarbonylaminobenzyl)-2-oxo-2,3-dihydro-benzoxazole-6-carboxylate |
| "A38" | Ethyl {3-[6-(3-methylaminopropylcarbamoyl)-2-oxobenzoxazol-3-ylmethyl]phenyl}carbamate |
| "A39" | Ethyl {3-[6-(3-dimethylaminopropylcarbamoyl)-2-oxobenzoxazol-3-ylmethyl]phenyl}carbamate |
| "A40" | Ethyl (3-{6-[3-(tert-butoxycarbonylmethylamino)propyl-carbamoyl]-2-oxobenzoxazol-3-ylmethyl}phenyl)carbamate |
| "A41" | |
| "A42" | |
| "A43" | |

| No. | Structure and/or name |
|---|---|
| "A43a" | |
| "A44" | |
| "A45" | |
| "A46" | |
| "A47" | |
| "A48" | |
| "A49" | N-propyl-3-{3-[5-(3-dimethylaminopropoxy)pyrimidin-2-yl]-benzyl}-2-oxo-2,3-dihydrobenzoxazole-5-carboxamide |
| "A50" | |
| "A51" | |
| "A52" | |
| "A53" | |
| "A54" | N-propyl-3-{3-[6-(3-dimethylaminopropoxy)pyridazin-3-yl]-benzyl}-2-oxo-2,3-dihydrobenzoxazole-5-carboxamide |
| "A55" | |
| "A56" | |
| "A57" | |
| "A58" | |
| "A59" | |

-continued

| No. | Structure and/or name |
|---|---|
| "A60" | |
| "A61" | |
| "A62" | |
| "A63" | |
| "A64" | Methyl 3-{3-[5-(3-dimethylaminopropoxy)pyrimidin-2-yl]-benzyl}-2-oxo-2,3-dihydrobenzoxazole-5-carboxylate |
| "A65" | |
| "A66" | |
| "A67" | |
| "A68" | |

-continued

| No. | Structure and/or name |
|---|---|
| "A69" | |
| "A70" | |
| "A71" | |
| "A72" | |
| "A73" | |
| "A74" | |
| "A75" | |
| "A76" | |

| No. | Structure and/or name |
|---|---|
| "A77" | |
| "A78" | |
| "A79" | |
| "A80" | |
| "A81" | |
| "A82" | |
| "A83" | |
| "A84" | |
| "A85" | |
| "A86" | |
| "A87" | |
| "A88" | |
| "A89" | |
| "A90" | |
| "A91" | |

-continued

| No. | Structure and/or name |
|---|---|
| "A92" | (structure) |
| "A93" | (structure) |
| "A94" | (structure) |
| "A95" | (structure) |
| "A96" | (structure) |
| "A97" | (structure) |
| "A98" | (structure) |
| "A99" | (structure) |

-continued

| No. | Structure and/or name |
|---|---|
| "A100" | (structure) |
| "A101" | (structure) |
| "A102" | (structure) |
| "A103" | (structure) |
| "A104" | (structure) |
| "A105" | (structure) |
| "A106" | (structure) |
| "A107" | (structure) |

| No. | Structure and/or name |
|---|---|
| "A108" | |
| "A109" | 3-{3-[5-(2-Dimethylaminoethoxy)pyrimidin-2-yl]benzyl}-5-methyl-3H-oxazolo[4,5-b]pyridin-2-one |
| "A110" | |
| "A111" | |
| "A112" | |
| "A113" | |
| "A114" | |
| "A115" | |
| "A116" | |
| "A117" | |
| "A118" | |
| "A119" | |
| "A120" | 3-{3-[5-(2,3-Dihydroxypropoxy)pyrimidin-2-yl]benzyl}-5-methyl-3H-oxazolo[4,5-b]pyridin-2-one |
| "A121" | |
| "A122" | |
| "A123" | |
| "A124" | |

| No. | Structure and/or name |
|---|---|
| "A125" | 5-Methyl-3-{3-[5-(4-methylpiperazin-1-yl)pyrimidin-2-yl]-benzyl}-3H-oxazolo[4,5-b]pyridin-2-one |
| "A126" | 5-Methyl-3-{3-[5-(4-methylpiperazin-1-yl)pyrimidin-2-yl]-benzyl}-3H-oxazolo[4,5-b]pyridin-2-one |
| "A127" | 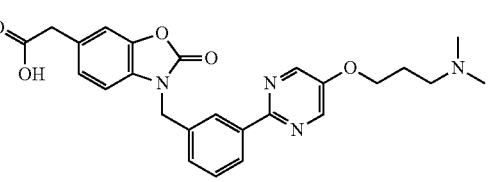 |
| "A128" | 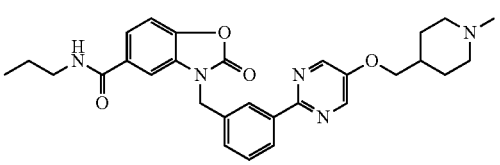 [SMILES: CCCNC(=O)c1ccc2oc(=O)n(Cc3cccc(-c4ncc(OCC5CCN(C)CC5)cn4)c3)c2c1] |
| "A129" | 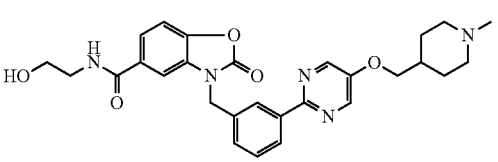 [SMILES: CN1CCC(COc2cnc(-c3cccc(Cn4c(=O)oc5ccc(C(=O)NCCO)cc54)c3)nc2)CC1] |
| "A130" | 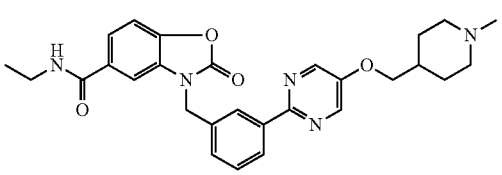 [SMILES: CCNC(=O)c1ccc2oc(=O)n(Cc3cccc(-c4ncc(OCC5CCN(C)CC5)cn4)c3)c2c1] |
| "A131" | 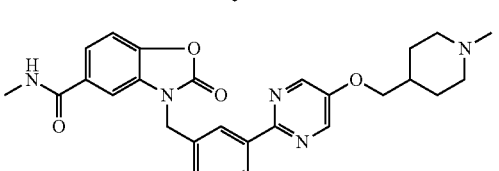 |
| "A132" | 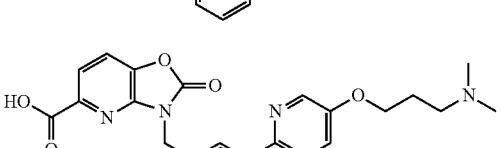 |
| "A133" | 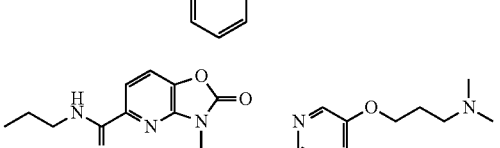 |
| "A134" | 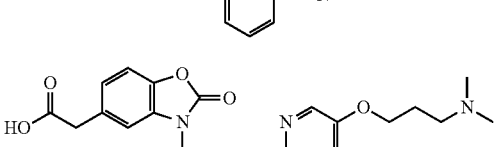 |

| No. | Structure and/or name |
|---|---|
| "A135" | 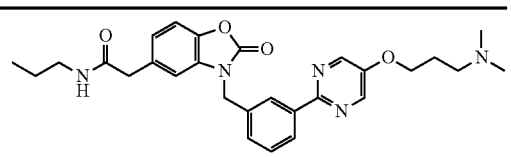 |
| "A136" | 3-{3-[5-(3-Dimethylaminopropoxy)pyrimidin-2-yl]benzyl}-6-(1-hydroxyethyl)-3H-benzoxazol-2-one |
| "A137" | 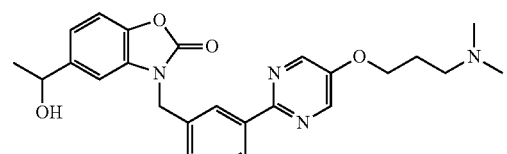 |
| "A138" | N-[3-(6-Chloro-2-oxobenzoxazol-3-ylmethyl)phenyl]acetamide |
| "A139" | 1-[3-(6-Chloro-2-oxobenzoxazol-3-ylmethyl)phenyl]-3-[3-(4-methylpiperazin-1-yl)propyl]urea |
| "A140" | 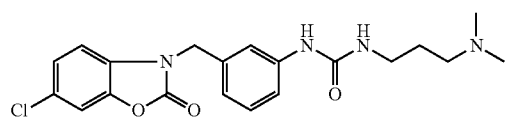 [SMILES: CN(C)CCCNC(=O)Nc1cccc(Cn2c(=O)oc3cc(Cl)ccc32)c1] |
| "A141" | N-[3-(6-Chloro-2-oxobenzoxazol-3-ylmethyl)phenyl]-N'-(2-dimethylaminoethyl)oxalamide |
| "A142" | N-(4-Dimethylaminobutyl)-2-[3-(5-methyl-2-oxooxazolo[4,5-b]pyridin-3-ylmethyl)phenyl]pyrimidine-5-carboxamide |
| "A143" | 5-Methyl-3-[3-(3-methyl-6-oxo-6H-pyridazin-1-yl)benzyl]-3H-oxazolo[4,5-b]pyridin-2-one |
| "A144" | 5-Methyl-3-[3-(5-methylpyridin-2-yl)benzyl]-3H-oxazolo[4,5-b]pyridin-2-one |
| "A145" | 5-Methyl-3-(3-pyrimidin-5-ylbenzyl)-3H-oxazolo[4,5-b]pyridin-2-one |
| "A146" | 5-Methyl-3-[3-(4-piperazin-1-ylpyrimidin-2-yl)benzyl]-3H-oxazolo[4,5-b]pyridin-2-one |
| "A147" | 5-Methyl-3-{3-[5-(1-methyl-1H-pyrazol-4-yl)pyrimidin-2-yl]-benzyl}-3H-oxazolo[4,5-b]pyridin-2-one |
| "A148" | 3-{3-[5-(3-Dimethylaminopropoxy)pyrimidin-2-yl]benzyl}-5-(1-methyl-1H-pyrazol-4-yl)-3H-oxazolo[4,5-b]pyridin-2-one | or a pharmaceutically usable salt, tautomer or stereoisomer thereof, including mixtures thereof in all ratios.

2. A method according to claim 1, where the solid tumour originates from the group of tumours of the squamous epithelium, the bladder, the stomach, the kidneys, of head and neck, the oesophagus, the cervix, the thyroid, the intestine, the liver, the brain, the prostate, the urogenital tract, the lymphatic system, the stomach, the larynx and/or the lung.

3. A method according to claim 1, where the solid tumour originates from monocytic leukaemia, lung adenocarcinoma, small-cell lung carcinomas, pancreatic cancer, glioblastomas and/or breast carcinoma.

4. A method according to claim 1, where the solid tumour originates from lung adenocarcinoma, small-cell lung carcinomas, pancreatic cancer, glioblastomas, colon carcinoma and/or breast carcinoma.

5. A method according to claim 1, where the tumour originates from acute myeloid leukaemia, chronic myeloid leukaemia, acute lymphatic leukaemia and/or chronic lymphatic leukaemia.

* * * * *

UNITED STATES PATENT AND TRADEMARK OFFICE
CERTIFICATE OF CORRECTION

PATENT NO. : 8,431,572 B2
APPLICATION NO. : 13/177261
DATED : April 30, 2013
INVENTOR(S) : Schadt et al.

Page 1 of 1

It is certified that error appears in the above-identified patent and that said Letters Patent is hereby corrected as shown below:

In the Claims:

Column 129, line 11 reads ""A27" 2-(4-Methylpiperazin-1-yl)propyl {3-[1-(5,6-difluoro-2-oxo-" should read -- "A27" 2-(4-Methylpiperazin-1-yl)ethyl {3-[1-(5,6-difluoro-2-oxo- --

Column 142, line 38 reads "benzyl}-3H-oxazolo[4,5-b]pyridine-2-one" should read -- benzyl}-3H-oxazolo[4,5-b]pyridine-2-one or --

Signed and Sealed this
Ninth Day of July, 2013

Teresa Stanek Rea
*Acting Director of the United States Patent and Trademark Office*